(12) United States Patent
Alphey et al.

(10) Patent No.: US 9,125,388 B2
(45) Date of Patent: Sep. 8, 2015

(54) BIOLOGICAL CONTROL

(71) Applicant: Isis Innovation Limited, Oxford (GB)

(72) Inventors: Luke Alphey, Abingdon (GB); Dean Thomas, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 13/942,601

(22) Filed: Jul. 15, 2013

(65) Prior Publication Data

US 2013/0298266 A1 Nov. 7, 2013

Related U.S. Application Data

(63) Continuation of application No. 11/733,737, filed on Apr. 10, 2007, which is a continuation of application No. 10/148,041, filed as application No. PCT/GB00/04541 on Nov. 29, 2000, now abandoned.

(30) Foreign Application Priority Data

Nov. 29, 1999 (GB) .................................. 9928181.8

(51) Int. Cl.

| A01K 67/00 | (2006.01) |
|---|---|
| C12N 15/00 | (2006.01) |
| A01K 67/033 | (2006.01) |
| C12N 15/82 | (2006.01) |

(52) U.S. Cl.
CPC ........... *A01K 67/0339* (2013.01); *A01K 67/033* (2013.01); *A01K 67/0333* (2013.01); *C12N 15/8238* (2013.01); *C12N 15/8285* (2013.01); *A01K 2217/05* (2013.01); *A01K 2227/706* (2013.01)

(58) Field of Classification Search
CPC ..................... A01K 2217/05; A01K 2227/706
USPC ....................................................... 800/8, 21
See application file for complete search history.

(56) References Cited

U.S. PATENT DOCUMENTS

| 5,254,801 | A |  | 10/1993 | Dotson et al. |
|---|---|---|---|---|
| 5,278,057 | A |  | 1/1994 | Jorgensen |
| 5,670,353 | A |  | 9/1997 | Ahlquist et al. |
| 5,674,747 | A | * | 10/1997 | Hammock et al. ......... 435/320.1 |
| 5,773,697 | A |  | 6/1998 | Tomes et al. |
| 5,851,796 | A |  | 12/1998 | Schatz |
| 5,977,441 | A |  | 11/1999 | Oliver et al. |
| 6,200,800 | B1 |  | 3/2001 | Choulika et al. |
| 6,338,040 | B1 |  | 1/2002 | Buman et al. |
| 6,962,810 | B2 |  | 11/2005 | Fraser et al. |
| 7,998,475 | B2 |  | 8/2011 | Alphey |
| 8,124,404 | B2 |  | 2/2012 | Alphey |
| 2003/0150007 | A1 |  | 8/2003 | Savakis et al. |
| 2004/0082032 | A1 |  | 4/2004 | Bovi et al. |
| 2005/0221430 | A1 |  | 10/2005 | Prentice |
| 2006/0212949 | A1 |  | 9/2006 | Alphey |
| 2006/0242717 | A1 |  | 10/2006 | Alphey |
| 2006/0275276 | A1 |  | 12/2006 | Alphey |
| 2007/0056051 | A1 |  | 3/2007 | Alphey |
| 2009/0170793 | A1 |  | 7/2009 | Gaur |
| 2009/0183269 | A1 |  | 7/2009 | Alphey |

FOREIGN PATENT DOCUMENTS

| EP | 0 636 310 | 2/1995 |
|---|---|---|
| EP | 0 955 364 | 11/1999 |
| GB | 2 355 459 | 4/2001 |
| WO | WO-90/08830 | 8/1990 |
| WO | WO-94/03619 | 2/1994 |
| WO | WO-96/04393 | 2/1996 |
| WO | WO-96/24605 | 8/1996 |
| WO | WO-97/30162 | 8/1997 |
| WO | WO-98/08960 | 3/1998 |
| WO | WO-99/10488 | 3/1999 |
| WO | WO-00/73510 | 12/2000 |
| WO | WO-01/39599 | 6/2001 |
| WO | WO-01/59088 | 8/2001 |
| WO | WO-01/91802 | 12/2001 |
| WO | WO-02/46444 | 6/2002 |
| WO | WO-02/101061 | 12/2002 |
| WO | WO-2004/044150 | 5/2004 |
| WO | WO-2004/098278 | 11/2004 |
| WO | WO-2005/003364 | 1/2005 |
| WO | WO-2005/012534 | 2/2005 |
| WO | WO-2007/091099 | 8/2007 |

OTHER PUBLICATIONS

Fryxell et al. (1995, Journal of Economic Entomology, vol. 88, pp. 1221-1232).*
Bello et al. (1998, Development, vol. 125, pp. 2193-2202).*
Deng et al. (Oct. 1999, J. Cell Science, vol. 112, pp. 3677-3690).*
Inoue et al. (1990, Nature, vol. 344, pp. 461-463).*
Adelman et al., "Formation and loss of large, unstable tandem arrays of the piggyBac transposable element in the yellow fever mosquito, *Aedes aegypti*," Transgenic Res (2004) 13(5):411-425.
Alphey et al., J. Econ. Entomol. (2007) 100(5):1642-1649.
Alphey et al., Molecular & Biochemical Parasitology (2002) 121:173-178.
Alphey et al., "Modeling resistance to genetic control of insects," Journal of Theoretical Biology (2011) 270:42-55.
Amendment for U.S. Appl. No. 10/562,843, filed Oct. 5, 2009, 10 pages.
Amendment for U.S. Appl. No. 10/562,843, filed Feb. 24, 2009, 13 pages.
Amendment for U.S. Appl. No. 10/562,843, filed Nov. 30, 2010, 7 pages.
Amendment for U.S. Appl. No. 10/566,448, filed Oct. 27, 2010, 20 pages.
Amendment for U.S. Appl. No. 10/566,448, filed Jul. 7, 2009, 15 pages.
Amendment for U.S. Appl No. 11/352,177, filed Dec. 10, 2009, 20 pages.
Amendment for U.S. Appl. No. 11/352,177, filed Oct. 14, 2010, 13 pages.
Arribas et al., Biochimica et Biophysica Acta (1986) 868:119-127.
Atkinson et al., "Genetic transformation systems in insects," Annu Rev Entomol (2001) 46:317-346.

(Continued)

*Primary Examiner* — Anoop Singh
*Assistant Examiner* — David A Montanari
(74) *Attorney, Agent, or Firm* — Morrison & Foerster LLP

(57) ABSTRACT

The invention relates to a non-human multicellular organism carrying a dominant lethal genetic system, the lethal effect of which is conditional, wherein the lethal effect of the lethal system occurs in the natural environment of the organism.

17 Claims, 13 Drawing Sheets

(56) References Cited

OTHER PUBLICATIONS

Figure 1:
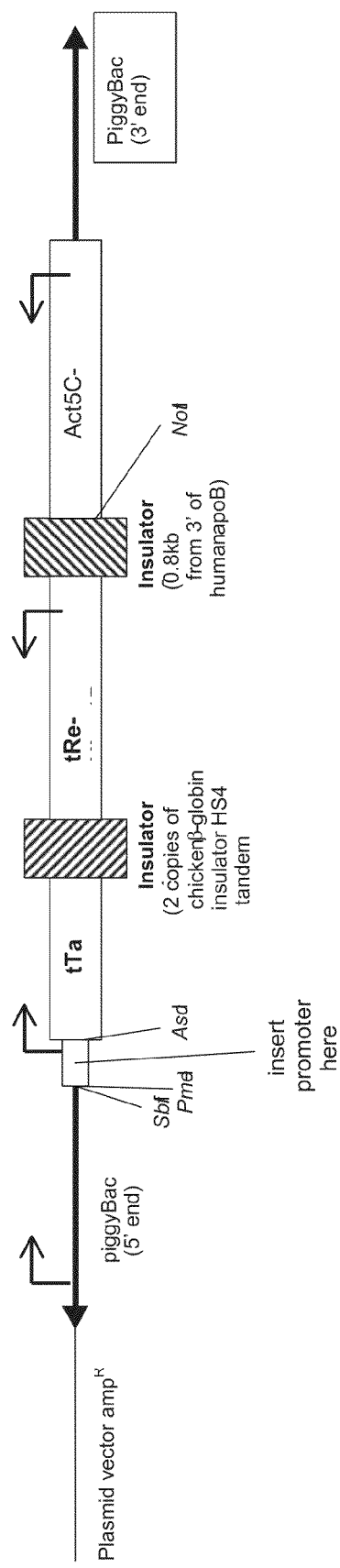

Atkinson et al. "*Hermes* and Other *hAT* Elements as Gene Vectors in Insects," In; *Insect Transgenesis: Methods and Applications*, (2000) Hadler et al. eds., Boca Raton CRC Press, pp. 219-235.

Bello et al., "Spatial and temporal targeting of gene expression in *Drosophila* by means of a tetracycline-dependent transactivator system," Development (1998) 125(12):2193-2202.

Beullens et al., "The isolation of novel inhibitory polypeptides of protein phosphatase 1 from bovine thymus nuclei," J Biol Chem (1992) 267(23):16538-16544.

Beullens et al., "Inactivation of nuclear inhibitory polypeptides of protein phosphatase-1 (NIPP-1) by protein kinase A," J Biol Chem (1993) 268(18):13172-13177.

Beullens et al., "Molecular determinants of nuclear protein phosphatase-1 regulation by NIPP-1," J Biol Chem (1999) 274(20):14053-14061.

Bieschke et al., Mol. Gen. Genet. (1998) 258:571-579.

Blitvich et al., Insect Molecular Biology (2002) 11(5):431-442.

Boudrez et al., "Identification of MYPT1 and NIPP1 as subunits of protein phosphatase 1 in rat liver cytosol," FEBS Letters 455 (1999) 175-178.

Burcin et al., "A regulatory system for target gene expression," Frontiers in Biosc. (1998) 3:c1-7.

Cabrera et al., Genesis (2002) 34:62-65.

Carriere et al., Proc. R. Soc. Lond. (2001) 268:1475-1480.

Chen et al., Food Science and Agriculture Chemistry (2000) 2(4):220-225.

Chen et al., The Journal of Biological Chemistry (1996) 271(42):25735-25737.

Communication pursuant to Article 96(2) EPC for EP 00979774.7, mailed Mar. 8, 2006, 4 pages.

Communication pursuant to Article 96(2) EPC for EP 00979774.7, mailed Aug. 2, 2005, 4 pages.

Communication pursuant to Article 96(2) EPC for EP 00979774.7, mailed Oct. 4, 2004, 4 pages.

Communication pursuant to Article 96(2) EPC for EP 00979774.7, mailed Nov. 28, 2003, 5 pages.

Communication under Rule 51(4) EPC, directed to EP 00979774.7, mailed May 9, 2007, 4 pages.

Davis et al., J. Theor. Biol. (2001) 212:83-98.

Decision on Further Processing for EP 00979774.7, mailed Jan. 29, 2007, 1 page.

Deng et al., "A targeted gene silencing technique shows that *Drosophila* myosin VI is required for egg chamber and imaginal disc morphogenesis," J Cell Science (1999) 112:3677-3690.

Devault et al., "Biotechnology and new integrated pest management approaches," Nature Biotechnology (1996) 14:46-49.

Egloff et al., "Structural basis for the recognition of regulatory subunits by the catalytic subunit of protein phosphatase 1," EMBO J (1997) 16(8):1876-1887.

Elick et al., Mol. Gen. Genet. (1997) 255:605-610.

Ernst, U. (1991) "Regulation of Sexual Differentiation in *Drosophila*: Alternative Splicing of the *Transformer* Primary Transcript Requires Masking of the Non-Specific Acceptor Site in Females," Inaugural Dissertation, Aus Frankfurt / Main, BRD.

Examination Report for EP 04743590.4, mailed Nov. 14, 2008, 4 pages.

Examination Report for NZ 519175, mailed Jul. 9, 2002, 2 pages.

Examination Report for NZ 519175, mailed Nov. 28, 2003, 1 page.

Final Rejection for U.S. Appl No. 10/562,843, mailed Feb. 3, 2010, 5 pages.

Final Rejection for U.S. Appl. No. 10/566,448, mailed Nov. 10, 2009, 18 pages.

Fryxell et al., "Autocidal biological control: a general strategy for insect control based on genetic transformation with a highly conserved gene," J Econ Entomol (1995) 88(5):1221-1232.

Fu et al., "Female-specific insect lethality engineered using alternative splicing," Nature Biotechnology (2007) 25(3):353-357.

Fu et al., PNAS (2010) 107(10):4550-4554.

Funaguma et al., Journal of Insect Science (2005) 5(17):1-6.

Fussenegger et al., Biotechnol. Prog. (1997) 13:733-740.

Gloor et al., Science (1991) 253:1110-1117.

Golovnin et al., "The su(Hw) insulator can disrupt enhancer-promoter interactions when located more than 20 kilobases away from the *Drosophila* achaete-scute complex," Mol Cell Biol (1999) 19(5):3443-3456.

Gong et al., "A dominant lethal genetic system for autocidal control of the Mediterranean fruitfly," Nat Biotechnology (2005) 23(4):453-456.

Gonzy-Treboul et al., Genes & Development (1995) 9:1137-1148.

Gossen et al. in: Tetracyclines in Biology, Chemistry and Medicine, Nelson et al. (eds.), Birkhauser Verlag, Switzerland (2001) pp. 139-157.

Handler, Insect Biochemistry and Molecular Biology (2002) 32:1211-1220.

Handler, Insect Biochemistry and Molecular Biology (2001) 31:111-128.

Harris et al., "Field performance of engineered male mosquitoes," Nature Biotechnology (2011) 29(11):1034-1039.

Heinrich et al., "A repressible female-specific lethal genetic system for making transgenic insect strains suitable for a sterile-release program," Proc Natl Acad Sci USA (2000) 97(15):8229-8232.

Heslip et al., Genetics (1994) 138:1127-1135.

Hofmann et al., PNAS USA (1996) 93:5185-5190.

Hondred et al., Plant Physiology (1999) 119:713-723.

Horn et al., Dev. Genes Evol. (2000) 210:623-629.

Horn et al., Genetics (2003) 163:647-661.

Horn et al., Insect Biochemistry and Molecular Biology (2002) 32:1221-1235.

Horn et al., Nature Biotechnology (2003) 21:64-70.

Imai, Res. Popul. Ecol. (1987) 29:129-146.

International Preliminary Report on Patentability for PCT/GB2007/000488, date of search May 5, 2008, 11 pages.

Further International Search Report for GB 9928181.8, mailed Apr. 30, 2001.

International Search Report for PCT/GB00/04541, mailed Dec. 5, 2001.

International Search Report for PCT/GB2004/003263, mailed Nov. 5, 2004, 3 pages.

International Search Report for PCT/GB2007/000488, mailed Jun. 6, 2007, 3 pages.

Jagiello et al., "NIPP-1, a nuclear inhibitory subunit of protein phosphatase-1, has RNA-binding properties," J Biol Chem (1997) 272(35):22067-22071.

Jin et al., "Mapping of the RNA-binding and endoribonuclease domains of NIPP1, a nuclear targeting subunit of protein phosphatase 1," Biochem J (1999) 342:13-19.

Johnson-Schlitz et al., Molecular and Cellular Biology (1993) 13(11):7006-7018.

Krafsur, "Bionomics of the face fly, *Musca autumnalis*," Annu Rev Entomol (1997) 42:503-523 (Abstract).

(56) References Cited

OTHER PUBLICATIONS

Lankenau et al., Molecular and Cellular Biology (1996) 16(7):3535-3544.
Louis et al., Genetics (2003) 165:1355-1384.
Loukeris et al., PNAS USA (1995) 92:9485-9489.
Munoz et al., Insect Molecular Biology (2004) 13(5):563-568.
Namciu et al., "Human matrix attachment regions insulate transgene expression from chromosomal position effects in Drosophila melanogaster," Mol Cell Biol (1998) 18(4):23822391.
Nitasaka et al., "Repressor of P elements in Drosophila melanogaster: Cytotype determination by a defective P element carrying only open reading frames 0 through 2," Proc Natl Acad Sci USA (1987) 84(21):7605-7608.
Non-Final Rejection for U.S. Appl. No 10/556,804, mailed May 12, 2010, 8 pages.
Non-Final Rejection for U.S. Appl. No. 10/562,843, mailed Jun. 9, 2009, 5 pages.
Non-Final Rejection for U.S. Appl. No. 10/562,843, mailed Jul. 30, 2010, 7 pages.
Non-Final Rejection for U.S. Appl. No. 10/562,843, mailed Nov. 12, 2008, 6 pages.
Non-Final Rejection for U.S. Appl. No. 10/566,448, mailed Jan. 7, 2009, 14 pages.
Non-Final Rejection for U.S. Appl. No. 10/566,448, mailed Apr. 27, 2010, 12 pages.
Non-Final Rejection for U.S. Appl. No. 11/352,177, mailed Apr. 14, 2010, 15 pages.
Non-Final Rejection for U.S. Appl. No. 11/352,177, mailed Jun. 10, 2009, 14 pages.
Noting of loss of rights (R. 69(1) EPC) for EP 00979774.7, mailed Jul. 17, 2004, 1 page.
O'Brochta et al., "Gene vector and transposable element behavior in mosquitos," J Exp Biol (2003) 206(Pt 21):3823-3834.
Office Action for AU 17165/01, mailed Jul. 13, 2004, 3 pages.
Office Action for CN 00818682.0, fax dated Feb. 4, 2005, 7 pages.
Office Action for IL 149885, dated Apr. 26, 2007, 4 pages.
Oxitec Nov. 2011 Newsletter, http://www.oxitec.com/our-news/newsletters/november-2011-newsletter/, downloaded Dec. 13, 2011, 6 pages.
Pane et al., Development (2002) 129:3715-3725.
Parker et al., "Functional interaction between nuclear inhibitor of protein phosphatase type 1 (NIPP1) and protein phosphatase type 1 (PP1) in Drosophila: consequences of over-expression of NIPP1 in flies and suppression by co-expression of PP1," Biochem J (2002) 368:789-797.
Phuc et al., BMC Biology (2007) 5:11.
PiggyBac website, http://piggybac.bio.nd.edu/, visited Mar. 21, 2006.
Rejection for CN 00818682.0, fax dated Jan. 26, 2006, 4 pages.
Request for Further Processing for EP 00979774.7, filed Jan. 4, 2007, 4 pages.
Request for Continued Examination for U.S. Appl. No. 10/566,448, filed Feb. 25, 2010, 18 pages.
Response to Communication pursuant to Article 96(2) EPC for EP 00979774.7, filed Feb. 13, 2006, 8 pages.
Response to Communication for EP 00979774.7, filed Apr. 14, 2005, 7 pages.
Response to Communication for EP 00979774.7, filed Sep. 20, 2004, 8 pages.
Response to Office Action for U.S. Appl. No. 10/556,804, filed Nov. 12, 2010, 12 pages.
Response to Restriction Requirement for U.S. Appl. No. 11/352,177, filed Mar. 13, 2009, 12 pages.
Response to Restriction Requirement for U.S. Appl. No. 10/566,448, filed Dec. 1, 2008, 9 pages.
Response to Restriction Requirement for U.S. Appl. No. 10/566,448, filed Feb. 8, 2008, 9 pages.
Response to Restriction Requirement for U.S. Appl. No. 10/556,804, filed Jun. 29, 2009, 2 pages.
Response to Restriction Requirement for U.S. Appl. No. 10/562,843, filed Jun. 27, 2008, 2 pages.
Response to Restriction Requirement for U.S. Appl. No. 11/352,177, filed Jun. 9, 2008, 9 pages.
Response to Restriction Requirement for U.S. Appl. No. 11/352,177, filed Nov. 3, 2008, 8 pages.
Response to Restriction Requirement for U.S. Appl. No. 12/278,849, filed Sep. 28, 2010, 13 pages.
Restriction Requirement for U.S. Appl. No. 10/556,804, mailed May 28, 2009, 5 pages.
Restriction Requirement for U.S. Appl. No. 10/562,843, mailed Jun. 12, 2008, 6 pages.
Restriction Requirement for U.S. Appl. No. 10/566,448, mailed Jan. 9, 2008, 5 pages.
Restriction Requirement for U.S. Appl. No. 10/566,448, mailed Aug. 29, 2008, 7 pages.
Restriction Requirement for U.S. Appl. No. 11/352,177, mailed Mar. 31, 2008, 8 pages.
Restriction Requirement for U.S. Appl. No. 11/352,177, mailed Sep. 2, 2008, 5 pages.
Restriction Requirement for U.S. Appl. No. 11/352,177, mailed Jan. 13, 2009, 10 pages.
Restriction Requirement for U.S. Appl. No. 12/278,849, mailed May 28, 2010, 7 pages.
Robinson, Mutation Research (2002) 511:113-132.
Ronaldson et al., "Two independent cis-acting elements regulate the sex- and tissue-specific expression of yp3 in Drosophila melanogaster," Genet Res. (1995) 66(1):9-17.
Rong et al., Genetics (2001) 157:1307-1312.
Rong et al., Science (2000) 288:2013-2018.
Russ et al., Journal of Virology (1996) 70(8):4927-4932.
Saccone et al., Genetica (2002) 116:15-23.
Saccone et al. (2000) "Sex Determination in Medfly: A Molecular Approach," In; Area-Wide Control of Fruit Flies and Other Pest Insects, Tan, K.H. ed., Penerbit USM, Penag, pp. 491-496.
Scali et al., The Journal of Experimental Biology (2005) 208:3701-3709.
Search Report for GB 0317656.7, date of search Nov. 25, 2003, 1 page.
Search Report for GB 0621234.4, dated of search Feb. 21, 2007, 1 page.
Second Office Action for AU 17165/01, mailed Mar. 21, 2006, 2 pages.
Second Office Action for CN 00818682.0, dated Jul. 28, 2006, 4 pages.
Sepp et al., Genetics (1999) 151:1093-1101.
Shelton et al., Nature Biotechnology (2000) 18:339-342.
Shockett et al., PNAS USA (1995) 92:6522-6526.
Simmons et al., "Field Performance of a Genetically Engineered Strain of Pink Bollworm," PLoS ONE (2011) 6(9):1-11.
Sondergaard et al., "Nutritional response in a Drosophila yolk protein gene promoter," Mol Gen Genet (1995) 248(1):25-32.
Spradling et al., "Transposition of cloned P elements into Drosophila germ line chromosomes," Science (1982) 218(4570):341-347.
Stadtfeld et al., "Without a trace? PiggyBac-ing toward pluripotency," Nat Methods (2009) 6(5):329-330.
Stebbins et al., PNAS (2001) 98(19):10775-10780.
Stebbins et al., Gene (2001) 270:103-111.
Steiner et al., Genetics (1995) 140:973-987.
Summary of Office Action for MX PA/a/2002/005337, mailed Jan. 3, 2007, 2 pages.
Supplemental Amendment for U.S. Appl. No. 11/352,177, filed Oct. 21, 2010, 15 pages.
Thomas et al., "Insect population control using a dominant, repressible, lethal genetic system," Science (2000) 287(5462):2474-2476.
Van Eynde et al., "Molecular cloning of NIPP-1, a nuclear inhibitor of protein phosphatase-1, reveals homology with polypeptides involved in RNA processing," J Biol Chem (1995) 270(47):28068-28074.
Van Eynde et al., "Organization and alternate splice products of the gene encoding nuclear inhibitor of protein phosphatase-1 (NIPP-1)," Eur J Biochem (1999) 261(1):291-300.

(56) References Cited

OTHER PUBLICATIONS

Vulsteke et al., "Properties and phosphorylation sites of baculovirus-expressed nuclear inhibitor of protein phosphatase-1 (NIPP-1)," J Biol Chem (1997) 272(52):32972-32978.
Weinmann et al., "A chimeric transactivator allows tetracycline-responsive gene expression in whole plants," Plant J (1994) 5(4):559-569.
Wera et al., "Inhibition of translation by mRNA encoding NIPP-1, a nuclear inhibitor of protein phosphatase-1," Eur J Biochem (1997) 247(1):411-415.
Wharton et al., "CNS midline enhancers of the *Drosophila* slit and Toll genes," Mech Dev (1993) 40(3):141-154.
Wimmer, "Eco-friendly insect management," Nat Biotechnology (2005) 23(4):432-433.
Wise De Valdez et al., "Genetic elimination of dengue vector mosquitoes," Proc Natl Acad Sci USA (2011) 108(12):4772-4775.
Wobus et al., Mol. Gen. Genet. (1990) 222:311-316.
Woltjen et al., "piggyBac transposition reprograms fibroblasts to induced pluripotent stem cells," Nature (2009) 458(7239):766-770.
Wool et al., Ent. Exp. & Appl. (1980) 183-190.
Written Opinion for PCT/GB2007/000488, mailed Jun. 6, 2007, 8 pages.
Wu et al., Journal of Biotechnology (2000) 80:75-83.
"Gene Linkage and Genetic Mapping," in Essential Genetics, Daniel L. Hartl and Elizabeth W. Jones (eds.), (1999) Jones and Bartlett Publishers, Sudbury, Massachussetts, pp. 126-127.
Guo et al., "Species-specific signals for the splicing of a short Drosophila intron in vitro," Mol Cell Biol (1993) 13(2):1104-1118.
Office Action in U.S. Appl. No. 10/556,804, mailed Feb. 1, 2011, 4 pages.
Response to Office Action for U.S. Appl. No. 10/556,804, filed Mar. 25, 2011, 9 pages.
Office Action in U.S. Appl. No. 10/562,843, mailed Feb. 16, 2011, 4 pages.
Response to Office Action in U.S. Appl. No. 10/562,843, filed Jun. 16, 2011, 9 pages.
Final Office Action in U.S. Appl. No. 10/562,843, filed Aug. 25, 2011, 5 pages.
Response to Final Office Action in U.S. Appl. No. 10/562,843, filed Nov. 21, 2011, 6 pages.
Office Action in U.S. Appl. No. 12/278,849, dated Oct. 10, 2012, 12 pages.
Response to Office Action in U.S. Appl. No. 12/278,849, dated Apr. 10, 2013, 19 pages.
Final Office Action in U.S. Appl. No. 12/278,849, dated Jun. 6, 2013, 24 pages.
Office Action in U.S. Appl. No. 12/278,849, dated Aug. 9, 2013, 22 pages.
Response to Office Action in U.S. Appl. No. 12/278,849, dated Jan. 9, 2014, 21 pages.
Office Action in U.S. Appl. No. 12/278,849 dated Mar. 17, 2014, 24 pages.
Response to Non-Final Office Action for U.S. Appl. No. 10/566,448, filed Aug. 28, 2009, 15 pages.
Final Office Action for U.S. Appl. No. 10/566,448, mailed Feb. 2, 2011, 13 pages.
Request for Continued Examination for U.S. Appl. No. 10/566,448, filed Aug. 2, 2011, 23 pages.
Non-Final Office Action for U.S. Appl. No. 10/566,448, mailed Nov. 22, 2013, 24 pages.
Response to Non-Final Office Action for U.S. Appl. No. 10/566,448, filed Apr. 22, 2014, 17 pages.
Final Office Action for U.S. Appl. No. 10/566,448, mailed Aug. 14, 2014, 24 pages.
Response to Final Office Action for U.S. Appl. No. 10/566,448, filed Dec. 15, 2014, 9 pages.
Notice of Appeal for U.S. Appl. No. 10/566,448, filed Feb. 18, 2015, 4 pages.
Notice of Allowance for U.S. Appl. No. 10/566,448, mailed Mar. 19, 2015, 10 pages.
Communication pursuant to Article 94(3) EPC for EP 07 712 717.3, mailed Jul. 11, 2014, 8 pages.
Alignment of Seq ID No. 22 of D1 (WO 2005/012534) with tTAV, Jul. 4, 2014.
Restriction Requirement for U.S. Appl. No. 10/148,041, mailed Mar. 10, 2005, 5 pages.
Response to Restriction Requirement for U.S. Appl. No. 10/148,041, filed Apr. 13, 2005, 10 pages.
Office Action for U.S. Appl. No. 10/148,041, mailed Jul. 1, 2005, 14 pages.
Response to Office Action for U.S. Appl. No. 10/148,041, filed Dec. 5, 2005, 11 pages.
Final Office Action for U.S. Appl. No. 10/148,041, mailed Mar. 7, 2006, 9 pages.
Request for Continued Examination for U.S. Appl. No. 10/148,041, filed Sep. 11, 2006, 8 pages.
Office Action for U.S. Appl. No. 10/148,041, mailed Oct. 10, 2006, 8 pages.
Office Action for U.S. Appl. No. 11/733,737, mailed Apr. 10, 2008, 8 pages.
Response to Office Action for U.S. Appl. No. 11/733,737, filed Oct. 10, 2008, 8 pages.
Restriction Requirement for U.S. Appl. No. 11/733,737, mailed Dec. 31, 2008, 9 pages.
Response to Restriction Requirement for U.S. Appl. No. 11/733,737, filed Jan. 26, 2009, 8 pages.
Final Office Action for U.S. Appl. No. 11/733,737, mailed Apr. 17, 2009, 16 pages.
Response to Final Office Action for U.S. Appl. No. 11/733,737, filed Jul. 17, 2009, 26 pages.
Advisory Action for U.S. Appl. No. 11/733,737, mailed Aug. 5, 2009, 4 pages.
Request for Continued Examination for U.S. Appl. No. 11/733,737, filed Aug. 14, 2009, 1 page.
Office Action for U.S. Appl. No. 11/733,737, mailed Oct. 1, 2009, 21 pages.
Response to Office Action for U.S. Appl. No. 11/733,737, filed Jan. 29, 2010, 23 pages.
Final Office Action for U.S. Appl. No. 11/733,737, mailed Aug. 4, 2010, 18 pages.
Response to Final Office Action for U.S. Appl. No. 11/733,737, filed Dec. 6, 2010, 26 pages.
Office Action for U.S. Appl. No. 11/733,737, mailed Feb. 8, 2011, 6 pages.
Response to Office Action for U.S. Appl. No. 11/733,737, filed Feb. 18, 2011, 11 pages.
Office Action for U.S. Appl. No. 11/733,737, mailed Jun. 28, 2011, 14 pages.
Response to Office Action for U.S. Appl. No. 11/733,737, filed Oct. 28, 2011, 27 pages.
Office Action for U.S. Appl. No. 11/733,737, mailed Mar. 27, 2012, 17 pages.
Response to Office Action for U.S. Appl. No. 11/733,737, filed Aug. 9, 2012, 24 pages.
Final Office Action for U.S. Appl. No. 11/733,737, mailed Jan. 7, 2013, 26 pages.
Response to Final Office Action for U.S. Appl. No. 11/733,737, filed Apr. 8, 2013, 25 pages.
Advisory Action for U.S. Appl. No. 11/733,737, mailed Jun. 3, 2013, 7 pages.
Notice of Appeal for U.S. Appl. No. 11/733,737, filed Jul. 3, 2013, 1 page.
Appeal Brief for U.S. Appl. No. 11/733,737, filed Feb. 3, 2014, 40 pages.
Examiner's Answer to Appeal Brief for U.S. Appl. No. 11/733,737, mailed Jul. 18, 2014, 12 pages.
Reply Brief and Request for Oral Hearing for U.S. Appl. No. 11/733,737, filed Sep. 18, 2014, 16 pages.
Notice of Appeal for U.S. Appl. No. 12/278,849, filed Jun. 17, 2014, 1 page.
Appeal Brief for U.S. Appl. No. 12/278,849, filed Oct. 16, 2014, 31 pages.

(56) References Cited

OTHER PUBLICATIONS

Office Action for U.S. Appl. No. 12/278,849, mailed Dec. 5, 2014, 15 pages.
Office Action for U.S. Appl. No. 12/278,849, mailed Mar. 10, 2015, 18 pages.
International Preliminary Examination Report for PCT/GB00/04541, mailed Apr. 4, 2002, 2 pages.
Written Opinion for PCT/GB2004/002021, received Oct. 4, 2004, 5 pages.
International Search Report for PCT/GB2004/002021, mailed Oct. 6, 2004, 3 pages.
International Preliminary Report on Patentability for PCT/GB2004/002021, issued Nov. 18, 2005, 6 pages.
International Search Report for PCT/GB2004/002869, mailed Jan. 11, 2005, 5 pages.
Written Opinion for PCT/GB2004/002869, received Jan. 12, 2005, 8 pages.
International Preliminary Report on Patentability for PCT/GB2004/002869, issued Jan. 3, 2006, 9 pages.
Written Opinion for PCT/GB2004/003263, received Nov. 5, 2004, 5 pages.
International Preliminary Report on Patentability for PCT/GB2004/003263, issued Jan. 30, 2006, 6 pages.
Supplemental Response for U.S. Appl. No. 11/352,177, filed Dec. 6, 2010, 4 pages.
Final Office Action in U.S. Appl. No. 11/352,177, mailed Mar. 16, 2011, 18 pages.
Response to Final Office Action in U.S. Appl. No. 11/352,177, filed Sep. 16, 2011, 15 pages.
Office Action in U.S. Appl. No. 11/352,177, dated Jan. 30, 2014, 17 pages.
Response to Office Action in U.S. Appl. No. 11/352,177, dated May 28, 2014, 14 pages.
Final Office Action for U.S. Appl. No. 11/352,177, mailed Oct. 14, 2014, 6 pages.
Response to Final Office Action for U.S. Appl. No. 11/352,177, filed Dec. 3, 2014, 8 pages.
Notice of Allowance for U.S. Appl. No. 11/352,177, mailed Mar. 17, 2015, 10 pages.
Request for Continued Examination for U.S. Appl. No. 11/352,177, filed Jun. 17, 2015, 3 pages.
Request for Continued Examination for U.S. Appl. No. 10/566,448, filed Jun. 18, 2015, 3 pages.
Further Search Report for GB 9928181.8, mailed Apr. 30, 2001.

* cited by examiner

SEQUENCE LISTING

<160> NUMBER OF SEQ ID NOS: 22

<210> SEQ ID NO 1
<211> LENGTH: 35
<212> TYPE: DNA
<213> ORGANISM: Artificial Sequence
<220> FEATURE:
<223> OTHER INFORMATION: Synthetically constructed oligonucleotide

<400> SEQUENCE: 1
aattgccacc atggctcata tggaattcag atctg                        35

<210> SEQ ID NO 2
<211> LENGTH: 37
<212> TYPE: DNA
<213> ORGANISM: Artificial Sequence
<220> FEATURE:
<223> OTHER INFORMATION: Synthetically constructed oligonucleotide

<400> SEQUENCE: 2
ggccgcagat ctgaattcca tatgagccat ggtgggc                      37

<210> SEQ ID NO 3
<211> LENGTH: 36
<212> TYPE: DNA
<213> ORGANISM: Artificial Sequence
<220> FEATURE:
<223> OTHER INFORMATION: Synthetically constructed oligonucleotide

<400> SEQUENCE: 3
aattgccacc atggctcata tggaattcag atctgc                       36

<210> SEQ ID NO 4
<211> LENGTH: 36
<212> TYPE: DNA
<213> ORGANISM: Artificial Sequence
<220> FEATURE:
<223> OTHER INFORMATION: Synthetically constructed oligonucleotide

<400> SEQUENCE: 4
ggccgcagat ctgaattcca tatgagccat ggtggc                       36

<210> SEQ ID NO 5
<211> LENGTH: 20
<212> TYPE: DNA
<213> ORGANISM: Artificial Sequence
<220> FEATURE:
<223> OTHER INFORMATION: Synthetically constructed oligonucleotide

<400> SEQUENCE: 5
taggagtaaa ggagaagaac                                         20

<210> SEQ ID NO 6
<211> LENGTH: 24
<212> TYPE: DNA
<213> ORGANISM: Artificial Sequence
<220> FEATURE:
<223> OTHER INFORMATION: Synthetically constructed oligonucleotide

<400> SEQUENCE: 6
aattccatat gtttgtatag ttca                                    24

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
gccgagctct tgacggttga agtacgaatg                              30

<210> SEQ ID NO 8

```
<211> LENGTH: 29
<212> TYPE: DNA
<213> ORGANISM: Artificial Sequence
<220> FEATURE:
<223> OTHER INFORMATION: Primer

<400> SEQUENCE: 8
cggccattca tatgcgtata ttcactatg                                    29

<210> SEQ ID NO 9
<211> LENGTH: 35
<212> TYPE: DNA
<213> ORGANISM: Artificial Sequence
<220> FEATURE:
<223> OTHER INFORMATION: Synthetically constructed oligonucleotide

<400> SEQUENCE: 9
aattgccacc atggctcata tggaattcag atctg                             35

<210> SEQ ID NO 10
<211> LENGTH: 36
<212> TYPE: DNA
<213> ORGANISM: Artificial Sequence
<220> FEATURE:
<223> OTHER INFORMATION: Synthetically constructed oligonucleotide

<400> SEQUENCE: 10
ggccgcagat ctgattccat atgagccatg gtgggc                            36

<210> SEQ ID NO 11
<211> LENGTH: 47
<212> TYPE: DNA
<213> ORGANISM: Artificial Sequence
<220> FEATURE:
<223> OTHER INFORMATION: Synthetically constructed oligonucleotide

<400> SEQUENCE: 11
gcggccgcac gggcccactc gagcacaagc ttcggtacca cgaattc                47

<210> SEQ ID NO 12
<211> LENGTH: 47
<212> TYPE: DNA
<213> ORGANISM: Artificial Sequence
<220> FEATURE:
<223> OTHER INFORMATION: Synthetically constructed oligonucleotide

<400> SEQUENCE: 12
gcggccgcac gggcccactc gagcacaagc ttcggtacca cgaattc                47

<210> SEQ ID NO 13
<211> LENGTH: 27
<212> TYPE: DNA
<213> ORGANISM: Artificial Sequence
<220> FEATURE:
<223> OTHER INFORMATION: Synthetically constructed oligonucleotide

<400> SEQUENCE: 13
aattgccacc atggaattca ctagtgc                                      27

<210> SEQ ID NO 14
<211> LENGTH: 27
<212> TYPE: DNA
<213> ORGANISM: Artificial Sequence
<220> FEATURE:
<223> OTHER INFORMATION: Synthetically constructed oligonucleotide

<400> SEQUENCE: 14
```
ggccgcacta gtgaattcca tggtggc        27

<210> SEQ ID NO 15
<211> LENGTH: 60
<212> TYPE: DNA
<213> ORGANISM: Artificial Sequence
<220> FEATURE:
<223> OTHER INFORMATION: Synthetically constructed oligonucleotide

<400> SEQUENCE: 15
ggccctcgag agaaggcctg cggccgctgt ggcgcgccag agtttaaaca gtcctgcagg        60

<210> SEQ ID NO 16
<211> LENGTH: 60
<212> TYPE: DNA
<213> ORGANISM: Artificial Sequence
<220> FEATURE:
<223> OTHER INFORMATION: Synthetically constructed oligonucleotide

<400> SEQUENCE: 16
gatccctgca ggactgttta aactctggcg cgccacagcg gccgcaggcc ttctctcgag        60

<210> SEQ ID NO 17
<211> LENGTH: 14
<212> TYPE: DNA
<213> ORGANISM: Artificial Sequence
<220> FEATURE:
<223> OTHER INFORMATION: Synthetically constructed oligonucleotide

<400> SEQUENCE: 17
ctagaagggc cctt        14

<210> SEQ ID NO 18
<211> LENGTH: 27
<212> TYPE: DNA
<213> ORGANISM: Artificial Sequence
<220> FEATURE:
<223> OTHER INFORMATION: Synthetically constructed oligonucleotide

<400> SEQUENCE: 18
aaacaattct gatagcgtgc gcgttac        27

<210> SEQ ID NO 19
<211> LENGTH: 34
<212> TYPE: DNA
<213> ORGANISM: Artificial Sequence
<220> FEATURE:
<223> OTHER INFORMATION: Synthetically constructed oligonucleotide

<400> SEQUENCE: 19
ggtaggcgcg cctggcgacc ggtggatccg aatg        34

<210> SEQ ID NO 20
<211> LENGTH: 24
<212> TYPE: DNA
<213> ORGANISM: Artificial Sequence
<220> FEATURE:
<223> OTHER INFORMATION: Synthetically constructed oligonucleotide

<400> SEQUENCE: 20
aaacgaattc accaccaggc agtg        24

<210> SEQ ID NO 21
<211> LENGTH: 32
<212> TYPE: DNA

<213> ORGANISM: Artificial Sequence
<220> FEATURE:
<223> OTHER INFORMATION: Synthetically constructed oligonucleotide

<400> SEQUENCE: 21
cttgtcgacg gcctatgaac tccgcgcgga gg                                    32

<210> SEQ ID NO 22
<211> LENGTH: 2412
<212> TYPE: DNA
<213> ORGANISM: Artificial Sequence
<220> FEATURE:
<223> OTHER INFORMATION: Synthetically constructed oligonucleotide

<400> SEQUENCE: 22

```
ctcgagttta ccactcccta tcagtgatag agaaaagtga agtcgagtt taccactccc      60
tatcagtgat agagaaaagt gaaagtcgag tttaccactc cctatcagtg atagagaaaa    120
gtgaaagtcg agtttaccac tccctatcag tgatagagaa aagtgaaagt cgagtttagg    180
agtccctatc agtgatagag aaaagtgaaa gtcgagttta ccactcccta tcagtgatag    240
agaaaagtga agtcgagtt taccactccc tatcagtgat agagaaaagt gaaagtcgag    300
ctcggtacgc ttaccgaagt atacacttaa attcagtgca cgtttgcttg ttgagaggaa    360
aggttgtgtg cggacgaatt ttttttttgaa acattaaccc ttacgggctg cagtaaagtg    420
caagttaaag tgaatcaatt aaaaagtaac cagcaaccaa gtaaatcaac tgcaactact    480
gaaatctgcc aagaagtaat tattgaatac aagaagagaa ctctgaatag ggaattggga    540
attgccacca tggctcatat ggaattcatg gctaacagct acgacatacc cagttgggct    600
ggaaaaccgc ccactggctt acatctggat gtgctaaagg acgacaaact agtacaaaaa    660
ctgatggtgg atgaaaaaag atgctatcta tttggtcgca acagtcaaat gaacgacttc    720
tgcatagacc atgcctcttg ttcgcgggtc cactcggcgt tgtctacca caagcacctc    780
aacatagcct acctcgtgga tctggggtcc actcatggca cctttattgg aacactcaga    840
ttggaagcgc acaagcccac acagctgcag attaatagca ccttccactt ggggcttct    900
acccggaact acatactcag ggaacgaccc tctggccacc acagcaacat catggaagac    960
ctgccgctca gtgaaaccag cgatggcgct ctcctgggcc tgcccgaaag ccaaacggag   1020
cttgataatc ttacagaata caacacggcc cacaatcggc gcatctcaat gctgggcatc   1080
gatgatgata ccaatatgcg aaagcaaaac gccttgaaac agggacggcg cactcgaaat   1140
gtcacattta cgatgagga gattgtcatc aatcctgagg atgtggatcc taatgtggga   1200
cgcttcagga acttggtaca aaccactgtg gtgcccgcca gagggctcg ctgcgacgtc    1260
aaccatatgg gcatccattc gggcaacagc agtttgtcca gtgccaatgc cgcacatgta   1320
caccaaatgt ccagcagag cctagttgac atgaagcagc agcataggga aatgcctccg   1380
cccaatgcgg tgctccactc gcctactaat tccctatatc aaggtctacc ggccgaaatg   1440
catggcaagg gtgacctaga gcccatctcc ccgctgagca ttggttccaa gttgggccta   1500
ttgctcccga atcctgcgcc tgaagtgtcg ccagtctatg acgaagctgt ggagacctcg   1560
acattggctc aaaagttggc cgtcgctaat gcaaacgttc gtcgcttcgg tgaggatccg   1620
catgactcga gtggcgaggg cgattcgctg tgcccacaga aaagaaata cgccaaggaa   1680
gcatggccag tcgcaagcc catgttgggg cagctgtaat tgcgtattaa caaaataatt   1740
aagattccac ctacgatttt ctcaagcata tgattgacaa cacactctgg agtaatattt   1800
gtttattaga cttttaacgt aaaacaaaaa aaaaaaaaa aaaaaaaaa aaaaaaaaa     1860
```

-continued

```
acgaatgctg cggccccta a ttccagctga gcgccggtcg ctaccattac cagttggtct    1920
ggtgtcgggg atccgtcgac taaggccaaa gagtctaatt tttgttcatc aatgggttat    1980
aacatatggg ttatattata agtttgtttt aagtttttga gactgataag aatgtttcga    2040
tcgaatattc catagaacaa caatagtatt acctaattac caagtcttaa tttagcaaaa    2100
atgttattgc ttatagaaaa aataaattat ttatttgaaa tttaaagtca acttgtcatt    2160
taatgtcttg tagacttttg aaagtcttac gatacattag tatctatata catggttcat    2220
tctacattct atattagtga tgatttcttt agctagtaat acattttaat tatattcggc    2280
tttgatgatt ttctgatttt ttccgaacgg attttcgtag acccttttcga tctcataatg    2340 gctcatttta ttgcgatgga cggtcaggag agctcgaatt aacggggatc cgtcgacctg    2400
cagcccaagc tt                                                        2412
```

BIOLOGICAL CONTROL

CROSS-REFERENCE TO RELATED APPLICATIONS

This application is a continuation of U.S. patent application Ser. No. 11/733,737 filed Apr. 10, 2007, which is a continuation of U.S. patent application Ser. No. 10/148,041 filed Sep. 26, 2002 which is the U.S. National Phase of PCT/GB2000/004541 filed Nov. 29, 2000, which claims priority to GB 9928181.8 filed Nov. 29, 1999. The contents of these applications are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 2003502SeqList.txt, date recorded: Jul. 12, 2013, size: 7,682 bytes).

TECHNICAL FIELD

The present invention relates to a method for controlling the population of an organism.

BACKGROUND ART

Methods of biological control are known for insects and plants. One method currently employed for the control of insect populations is termed the "sterile insect technique" (SIT), also known as the "sterile insect release method" (SIRM). In this method, sterile males are released into the environment, wherein they compete with the wild-type (fertile) males for mates. Females which mate with sterile males produce no offspring, and the release of large numbers of sterile males, therefore, leads to a decrease in the size of the next generation. In this way the size of the wild population is controlled.

SIT requires some mechanism for insect sterilisation. In addition, SIT commonly also employs separation of males from females, with the release of only one sex. This is desirable in the case of an agricultural pest, such as the medfly, where the female damages fruit, even if the female is sterile. Similarly, only the female mosquito bites humans. As such, release of the female insect is preferably avoided in these cases.

Current techniques to achieve both sterilisation and separation of the sexes all have drawbacks. In some cases it is possible to separate males and females by criteria such as pupal mass or time of eclosion, but these methods are unlikely reliably to yield a truly single-sex population. Separation of males and females often involves the use of mutant strains, which have been mutagenised to induce a visible or otherwise selectable difference between the sexes, but such mutagenesis can reduce the fitness of the resultant stock with respect to the wild type, which is undesirable.

Fitness may be further reduced in the sterilisation procedure, in which insects are given a sterilising dose of radiation (X rays or gamma rays), or are chemically sterilised. Frequently, the doses of chemicals or the dose of radiation required to induce sterilisation are very similar to that which is lethal for the organism. As such, sterile organisms are frequently impaired in their ability to mate. Furthermore, both chemical and irradiation methods utilise technologies which are not specific to the target organism, with consequent potential danger to workers. Both methods produce an environmental hazard, as the irradiation source or chemicals will need to be disposed of. In addition, there are inherent dangers and additional labour costs in the use of an irradiation source such as a strontium source.

Fryxell and Miller (Journal of Economic Entomology, Vol 88, No 5, pages 1221-1232) disclose an alternative strategy for insect control, using *Drosophila* containing a dominant conditional lethal gene which is expressed under appropriate cold conditions in the wild. However, this method can be ineffective due to varying field conditions, where the environment does not provide suitably cold conditions. Moreover, organisms that live in a range of temperature habitats may not be controlled under all conditions.

Asburner et al., (Insect Molecular Biology, 1998, 7(3), 201-213) disclose methods of transformation of insect species with foreign DNA, to produce transgenic species.

DeVault et al. (Biotechnology, Vol 14, January 1996, page 46-49) disclose a two-stage process which is a modification of the SIT procedure. Insects are initially separated by expression of a stably inserted female specific promoter linked to a lethal gene, which is expressed to kill females and to produce just one sex. The remaining males can then be sterilised by irradiation or chemical treatment and released into the environment. However, this method suffers from the drawback referred to above, in that released flies have reduced fitness due to the sterilisation treatment. Alternatively, the DeVault article discloses use of this genetic sexing step in combination with a second genetic system, which may serve to sterilise or retard the hardiness of the natural population.

There is still a need in the art for a method of biological control which avoids the problems with the above methods.

The present invention sets out to overcome such problems.

SUMMARY OF THE INVENTION

In a first aspect, the invention relates to a non-human multicellular organism carrying a dominant lethal genetic system, the lethal effect of which is conditional, wherein the lethal effect of the lethal system occurs in the natural environment of the organism.

In a related aspect, the invention relates to an organism viable in a laboratory under controlled conditions. Controlled conditions are conditions that do not occur in the natural environment of the organism. As such, the conditions are typically artificial. Removal of the controlled conditions permits expression of the lethal genetic system. The organism may be autocidal, in that it will be killed after release into the environment. Suitably the organism can transmit a lethal element to at least some of its offspring, such that at least some of these offspring are also killed.

The organism of the invention can be used in population control to pass on the lethal genetic system through mating, and also to block potentially productive mating of wild type organisms. Distribution of the organism of the present invention into the environment thus initiates a biological control system. The organism of the present invention does not need to be sterilised, thus avoiding problems with sterilisation through irradiation and loss of genetic fitness.

In a further aspect, the invention provides a method of biological control, comprising:

i breeding a stock of male and female organisms under permissive conditions, allowing the survival of males and females, to give a dual sex biological control agent;

ii releasing the dual sex biological control agent into the environment at a locus for biological control, and iii achieving biological control through expression of the genetic system in offspring resulting from interbreeding of the individuals of the biological control agent with individuals of the opposite sex of the wild population.

Preferably there is no specific sterilisation step for released organisms.

In addition, we have now discovered a new method for biological control, applicable to organisms capable of sexual reproduction, wherein only one lethal genetic system is required, the expression of which is used in both sex separation and biological control. In this case the lethal genetic system is made to be sex-specific. The lethal genetic system is preferably a conditional dominant sex-specific lethal genetic system, which is expressed in the restrictive conditions of the natural environment of an organism. However, the expression of the lethal genetic system may be controlled under permissive conditions in a laboratory, factory or other regulated system, for example, to allow growth of a normal populations, e.g. insect stock with both sexes. Prior to release of the factory or laboratory stock into the environment the conditions can be manipulated to ensure only single sex populations of the organism are distributed into the environment. No additional irradiation of the organism is required and the arrangement removes any requirement for use of two separate genetic systems (i.e. those employed by DeVault et al. for sexing and, for example, sterilisation). Only one genetic system needs to be constructed and inserted into the organism, which renders the methodology easier and quicker.

Thus, in a further embodiment of the invention, the multicellular organism carries a dominant sex-specific lethal genetic system which is conditional, and does not have a dominant sex-specific lethal genetic system which is unconditional and is expressed in every individual.

Specifically, under permissive conditions, the lethal genetic system in the organisms of this invention is not expressed, and a stock of organisms can be bred. Imposition of restrictive conditions then allows one sex (for example, females) to be killed. The remaining sex (males) can be released to the environment, and the genetic system is passed on to at least some offspring resulting from any sexual reproduction between said males and a wild-type organism of the same species. The conditional dominant lethal genetic system is selected such that expression of the lethal system occurs in the natural environment. As a result, for a female specific lethal genetic system, all females which result from the mating are then killed or rendered non viable due to the action of the genetic system, while the males survive to pass on the system to the next generation in a proportion of cases. In this way, biological control is achieved.

If desired, the stock of organisms grown under permissive conditions can be released into the environment, without imposing the restrictive conditions to kill off one sex before release. This variation permits the possibilities of using a timing mechanism, e.g. life cycle stage, in creating a biological control agent. That is, the imposition of the restrictive condition is programmed by an event other than, for example, a pre-determined change in factory/laboratory conditions prior to release into the environment. For example, release of a normal population of larvae creates a useful time-scatter or delayed release agent. By this is meant that individual larvae may proceed to maturity at different rates and therefore release of the single sex genetically engineered population could occur over a period of time and hence create a maximum probability of interaction with sexually active wild populations over that period. This aspect may have advantages over a single time point release of a single sex population of the genetically engineered adults. There are other advantages, notably that the last (biggest) generation does not have to be reared in the factory, laboratory or other regulated environment, so saving space and food and thereby giving a more economic process. Moreover, the released larvae will compete with the larvae of the wild population, increasing mortality through density-dependent mechanisms. By way of illustration, this variation might be useful with mosquitoes, where the larvae are harmless to humans, but not with medfly or codling moth, where the larvae eat fruit.

Therefore, in a further aspect the present invention provides a method of biological control for an organism, the organism having discrete sexual entities, the method comprising the steps of:

1 production of a stock of genetically engineered organism;
2 release of the genetically engineered organism into the environment either as
  a) a normal population (i.e. containing both sexes) at a certain stage of the life cycle of the organism, e.g. larvae, in the knowledge that females will die and only males will mature into adults, or
  b) a single sex population, i.e. after the sex specific dominant lethal effect has been expressed prior to release.

The invention relies on expression of a conditional dominant lethal genetic system capable of sex specific lethality, in order to eliminate one sexual entity. The conditional expression of the lethal gene is such that the lethal effect occurs in the natural environment of the organism to cause the biological control.

In a yet further aspect of the invention, the invention accordingly involves a third step;

3 allowing biological control to occur.

The invention further provides a method of biological control, comprising:

breeding a stock of males and female organisms under permissive conditions, allowing the survival of males and females, to give a dual sex biological control agent;
optionally before the next step imposing or permitting restrictive conditions to cause death of individuals of one sex and thereby providing a single sex biological control agent comprising individuals of the other sex carrying the conditional dominant lethal genetic system;
releasing the dual sex or single sex biological control agent into the environment at a locus for biological control, and
achieving biological control through expression of the genetic system in offspring resulting from interbreeding of the individuals of the biological control agent with individuals of the opposite sex of the wild population.

The invention also relates to organisms comprising a conditional dominant lethal genetic system for use in a combined method of sex separation and biological control, as herein defined.

The invention further provides a multi-phase lethal system having lethality at more than one life cycle stage. Specifically, the invention provides an organism or single sex population for use in biological control, wherein the organism or single sex population produces no viable progeny when mated with the wild-type opposite sex under restrictive conditions, e.g. in the natural environment. For example, the invention provides a male population which produces no viable male or female progeny. This contrasts with the situation in which a male only population produces no female progeny but viable male progeny.

The invention further provides a method for the sex-separation of organisms, wherein the expression of a sex specific dominant conditional lethal system is used to kill one sex to leave either an essentially pure male or female population, or a population in which organisms comprise either male or female tissues, or a population in which organisms are unable to produce functional male gametes or female gametes (or both) which they would have been able to produce but for expression of the lethal genetic system.

The invention further provides a method of biological control in which the growth of a stock of organisms under permissive conditions, once initiated, is self-sustaining and requires no additional pool of organisms for its maintenance.

The invention further provides a method of biological control in which the expression of the lethal genetic system occurs in the absence of a substance which is absent from the natural environment of the organism, thus ensuring effective biological control when the organism is released.

The invention further provides a vector for use in transformation of an organism to produce an organism according to the present invention, suitable for use in a biological control scheme.

GENERAL DESCRIPTION OF THE INVENTION

The general features of the invention are first outlined in broad terms for ease of understanding, before being specifically detailed. The invention is discussed herein with respect to both organisms for use in a method of biological control and methods of biological control. Reference to an organism thus generally is taken to include a method of biological control employing that organism, and vice versa.

The non-human organism of the present invention is suitably a recombinant organism, into which the dominant lethal genetic system has been transformed. The organism is also at least capable of sexual reproduction or attempting sexual reproduction, such that the dominant lethal genetic system can be passed into the naturally occurring population of that organism, or the organism can compete with wild type organisms in mating.

The lethal genetic system is suitably comprised of a lethal gene and controlling and/or regulatory elements. However, in one embodiment, the lethal system may be comprised simply of a lethal gene, sufficient to produce the lethal effect.

The dominant genetic system suitably includes a dominant gene whose effect is phenotypically expressed in the heterozygous state. This dominant effect ensures that, if an organism only receives one copy of the lethal genetic system, then the lethal effect of that system will nevertheless be exerted in the host in the natural environment of the organism.

The lethal genetic system may be sex-specific or non-sex specific, the former being generally preferred. In the case of a sex-specific lethal system it is possible to carry out a genetic sex-selection before release of organisms for biological control.

When a single sex biological control agent is desired, separation of the sexual entities is normally achieved in the method by removal of permissive conditions while a stock of an organism is grown up, resulting in the sex specific lethal effect of the genetic system being manifested. A single sex population remaining may then be isolated.

We prefer that the lethal effect is female specific. However, a male specific lethal effect may be required in certain situations. With reference to plants, the sexual entities need not be discrete organisms, but parts of the same organism. The present invention may thus also be applied to plants, wherein one sexual entity of a plant is killed. With a single sex biological control agent, the conditional dominant lethal genetic system is permitted to be expressed during growth cycles before release, and the plant then distributed. Alternatively, no such permissive expression might be needed before release, for instance in the case of seed distribution with the lethal effects only manifesting once the plant reaches a certain further stage in its life cycle in the environment.

With respect to insects and other animals, distributing the organism typically occurs by release of the organism into the environment. With plants, distributing typically occurs by planting of mature plants, seedlings or seeds, or any suitable form of the organism in the environment.

The conditional effect of the dominant lethal genetic system is seen except under defined permissive conditions. In the present invention the restrictive conditions occur in the natural environment of the organism, and are those conditions which allow the lethal effect of the lethal system to be expressed. The permissive conditions which allow the survival of the organism are only present when adopting permissive conditions in the regulated growing environment.

Preferably expression of the dominant lethal genetic system is conditional upon the presence of a substance or condition not found in the natural environment, such as an artificial or synthetic compound, suitably an antibiotic, antibiotic analogue or derivative. Such an artificial substance or condition is suitably always absent from the natural environment, that is, it is never or only rarely present in the natural environment in sufficient abundance or concentration to inactivate or functionally repress the lethal genetic system. Preferably absence of the substance or condition results in expression of the lethal effect of the lethal system.

The natural environment of the organism is generally the environment in which the population to be controlled is located, or may survive. Additionally, the natural environment is also an environment which provides the necessary restrictive conditions. The universal nature of the invention allows universal application of the methods used in the invention, and the natural environment may thus be any world environment in which biological control is needed, without restriction.

DETAILED DESCRIPTION OF THE INVENTION

The lethal genetic system of the present invention may be any genetic element or combination of elements which is capable of producing a lethal effect. We prefer that the lethal genetic system comprises a DNA sequence encoding a potentially lethal gene product (a lethal gene) and controlling elements such as promoters, enhancers or trans-activator components. The elements which regulate the gene may be located on the same chromosome as the lethal gene, which is preferred, or on a different chromosome. We particularly prefer that the lethal system is a lethal gene the expression of which is under the control of a repressible transactivator protein. In an alternative embodiment the lethal system may simply be the lethal gene alone, or in combination with its native promoter.

Preferably the organism of the present invention has only one lethal genetic system, the system being conditional on environmental factors. More preferably the system has only one conditional lethal gene. The use of a simple genetic system minimises the chance of genetic complication when producing or carrying out the invention. Typically the organism contains no transgenes or other non-natural gene or DNA arrangements, other than that of the lethal genetic system of the invention.

The lethal effect of the lethal system may affect the whole organism, or be targeted to specific tissues within an organism. For example, in plants the lethal effect may be targeted to only a part of the host plant, such as one of the sexual organs of the plant. As such, in the present invention, a reduction in the wild type population size is achieved without the use of applied sterilisation by externally applied agents such as irradiation or chemicals, but through the use of targeted lethality based on zygotic lethality, or male or female or total sterility.

In particular, in plants, we prefer that precursors of the male and/or female gamete-producing tissues or critical parts thereof within the plant are targeted by the lethal effect, such that these tissues die when the plant is grown in the natural environment. In this way, the plant will produce no pollen or seed, or neither pollen nor seed, unless grown under permissive conditions. Given general environmental concerns over genetically modified crops, this invention is therefore especially useful when applied to plants which are transgenic at another locus. The transgenic plant will then release no pollen or seed, and cannot cross pollinate other species or otherwise spread into the environment. This is of especial benefit where the plant has wind-blown pollen. In this way, the transgenic plant is contained, and can be grown in field studies for testing prior to commercialisation without risk to the environment.

The invention thus relates to a method for the field testing of transgenic crops, comprising the step of growing a transgenic plant comprising the conditional lethal dominant system of the invention under permissive conditions, and then distributing the plant into the environment where it is exposed to restrictive conditions. A field test is generally any test carried out on a transgenic plant to assess its characteristics, such as its commercial suitability as a crop or foodstuff, for example. The invention also extends to plants having the conditional lethal dominant system of the invention in combination with one or more transgenes.

The lethal effect may also be targeted to a specific life cycle stage of the organism. Where life cycle specificity is sought, we prefer that the lethality of the invention is embryo-specific lethality. The lethal phase suitably ends before the developmental stage at which the organisms are released, or they may lose fitness or die following release. In the case of insects, embryonic lethality ensures that no larvae emerge to damage crops or animals. Whilst this is less important in the case of disease vectors such as mosquitoes, where only the adult stages transmit the disease, it is important in the case of many crop pests where it is the larvae that cause economic damage. Embryo-specific lethality allows the last and biggest mass-reared generation to be reared on food lacking the repressor, reducing costs. Embryo-specific lethality can also be combined with later sex-specific lethality, e.g. female-specific lethality. In this case we demonstrate that this allows the construction of a strain in which both sex-separation and "sterilisation" are automatic consequences of the withdrawal of permissive conditions from the last generation prior to release.

Also preferred, in certain circumstances, is late-acting lethality, which takes advantage of the feature of density-dependent negative selection, in which the chances of an individual surviving to reproduce is negatively dependent of the total number on individuals in the population of which it is a part. The mechanism for this is typically competition between individuals for limited resources, such as food. By way of example, in the case of mosquitoes, this competition might act on larvae competing for food. If the lethal phase is later than this larval competition stage, then the individuals (e.g. female larvae) who will be killed by the lethal system will nonetheless compete for resources during their larval stage and so indirectly reduce the numbers of their conspecifics, even those that do not carry the lethal system at all.

Therefore, preferred is a lethal system which is lethal at a life cycle stage which allows competition between organisms of the invention and wild type organisms to occur.

Preferably the lethal expression is such that individuals die before they cause the damage which it is intended to prevent. By way of example, in the case of mosquitoes it is desirable to reduce disease transmission. The earliest that a female mosquito can transmit disease is the second blood meal (having picked up the parasite/virus in the first blood meal and so become infectious). Therefore, the mosquito can be killed as late as shortly after the first blood meal. In addition, mosquito feeding is also undesirable, and preferably killing is effected shortly before or just after the first blood meal.

The lethal gene of the lethal genetic system may be any genetic element which is capable of causing the death of, or leading to the fatality of, the host. In particular, the term covers gene fragments capable of exerting a lethal effect, and is not limited to full length genes. Any element capable of exerting a lethal effect which may be conditionally controlled is covered by this term.

The choice of dominant lethal gene is not critical to the invention. There is a wide range of suitable gene products, with varying toxicities. For example, dominant mutant forms of cell-signalling or cell-cycle genes are appropriate for use in the present invention. Constructs which result in overexpression of such genes may also be lethal. Similarly constructs which result in inadequate expression of any essential gene would also be lethal. This might be achieved by expression of an inhibitory sequence, for example antisense RNA, sense RNA (acting by gene silencing), double stranded RNA ("inhibitory RNA" or RNAI) or other inhibitory RNA molecule. Overexpression of protein inhibitors of essential functions could also perform this lethal function. Other suitable targets for engineering constructs include genes which disrupt metabolism or regulation of the cell to a fatal extent, such as disruption or overexpression of extracellular signalling factors such as functional homologues of Wnt, Shh or TGFβ. Preferred lethal genes are those described in the Examples herein, the hid gene [see Heinrich and Scott, P.N.A.S Jul. 18, 2000, volume 97, 15, 8229-8232], and the Nipp1Dm gene, a *Drosophila* homologue of mammalian NIPP1 (see Example 7). Other possibilities for lethal genes include sex-determination genes which may act to transform the sex of the organism. In this case, transformation of females to sterile males would also enable biological control to be achieved, and the lethal gene is lethal to the population as such and not specifically to the organism. Where highly toxic gene products are used, such as diphtheria toxin and ricin A, we prefer that the genes are only expressed at levels sufficient to kill the organism, but with minimum environmental impact.

A preferred lethal gene for use in the invention has a threshold of toxicity—below a certain level it is harmless while above it is lethal. Additionally, to reduce the possibility of resistance, the lethal gene preferably has multiple essential targets. Nipp1Dm generally fulfils these criteria. It encodes a highly conserved protein present in all cells at a significant level. Modest over-expression is therefore unlikely to have any adverse consequences. It is a potent inhibitor of three essential genes in *Drosophila*, each of which have highly pleiotropic effects. Accordingly, because of the high level of conservation of this protein between *C. elegans, D. melanogaster* and mammals, Nipp1Dm is a preferred lethal gene for use in the present invention.

The conditional nature of the lethal system allows recombinant organisms to be bred under conditions permissive for organism survival, for example in a factory or laboratory, and then released into the natural environment. The lethal effect of the lethal system is controlled such that the released organisms are able to breed, and sexual reproduction allows the lethal system to be passed into the wild type population, killing all or a defined group of these organisms. We prefer that the lethal effect results in killing of greater than 90% of the target class of the progeny of matings between released organisms and the wild population. The target class may be, for example, females, i.e. 50% of the progeny. More preferably the lethal effect results in killing of greater than 95% of the target class, still more preferably 99% and most preferably 100% of the target organisms in the environment.

The conditional nature of the lethal system may be conditional on any suitable factor, such as temperature, diurnal cycle (with light duration and/or intensity being factors) or pheromones, for example. In this case, the recombinant stock could be reared at the permissive temperature, and released into an environment having a restrictive temperature. Suitably the lethal effect occurs at a temperature which is at least 5° C., more preferably 10° C., more preferably 20° C., within the extremes of the temperature range known to occur in the environment of the organism across the world, such that there is always expression of the lethal effect in the environment.

Preferably the lethal effect of the lethal system is inherently insensitive to temperature variations or fluctuations which occur in the natural environment of the organism.

Where the expression of the lethal system is not conditional on temperature but is temperature sensitive to any extent, we prefer that greater than 90% of the organisms are killed in the natural environment, more preferably at least 95%, preferably at least 98%, preferably at least 99% or more.

The lethal genetic systems of the present invention are generally not susceptible to temperature to any significant extent, so that for example, the difference in lethal effect at 18° C. and 29° C. is less than 5%, preferably less than 1%. The preferred lethal genetic systems of the invention are suitably functional across a broad temperature range, such as may occur naturally within the environment where the organism is found. Examples of typical temperature ranges are 0° C. to 50° C., more usually 10° C. to 45° C., such as 15° C., 20° C. or 25° C. to 30° C., 35° C. or 40° C. Preferably the lethal effect is exhibited in at least 95% of organisms across this whole temperature range, in that 95% of organisms are killed at any given temperature in the range, more preferably 98%, 99% or even more. More generally, the highest survival rate at any temperature is preferably less than 10%, suitably 5%, 2%, 1% or less.

The lethal effect of the lethal system is preferably expressed in the natural environment when the organism is distributed into its natural environment or any naturally occurring environment, irrespective of the natural conditions which can occur or which prevail in that environment.

We prefer that the lethal effect of the lethal system is conditional upon a dietary additive, such as a food or water additive, which is not a normal food component for the target species. This allows the recombinant stock to be grown on food or water containing the additive, which prevents the lethal effect. On release into the wild, the organism has no exposure to the additive, and the lethal effect of the lethal system is expressed in the progeny of a mating with the recombinant organism of the invention. It may also be expressed in the parent organism under certain circumstances, although the released organism must survive long enough to mate.

Preferred factors on which the expression of the lethal system can be made conditional include antibiotics such as tetracycline and non-antibiotic tetracycline analogues and derivatives thereof, which function with the preferred tetracycline repressible system of the present invention. Non-antibiotic compounds are especially preferred to avoid potential problems with antibiotic accumulation in the environment. Suitable analogues include epioxytetracycline and anhydrotetracycline, although other suitable analogues may also be employed, as appropriate.

Where the lethal effect is conditional upon a dietary additive, it may be that the progeny will survive without themselves ingesting or absorbing the dietary additive. For example, the progeny might retain sufficient of the additive from their parents or from an earlier life cycle stage without feeding, or at the least the additive may be slowly lost from the progeny. This effect might pass through one or more generations before the lethal effect is fully expressed under restrictive conditions.

We prefer that the recombinant multicellular organism of the present invention contains a dominant lethal system the lethal effect of which is conditionally suppressible. In this way, the lethal effect is suppressed under controlled conditions, but not suppressed in the natural environment of the organism. However, there may be other ways to attain conditional expression (for example, conditional activation), any of which may be used in the present invention.

We particularly prefer that the repressible expression system is a tetracycline repressible system in which tetracycline, or an analogue or derivative thereof, is used to inhibit expression of the lethal system. One suitable system is described in detail in the examples herein, in insects. This tetracycline system has also been shown to work in plants (see Zuo and Chua, 2000, Curr. Opin. Biotech. 11:146 and references therein).

The repressible lac repressor system is less preferred, as the inducer (IPTG) is less diffusible and more toxic than tetracycline.

By way of contrast, an inducible system may be based upon the constitutive expression of a toxin and inducible expression of a repressor of the toxin. One such example described in Zuo and Chua (supra) in relation to plants is based on expression of a chimeric transcription factor which is normally inactive (sequestered by binding to Hsp90). In the presence of the inducer (a steroid hormone or analogue, e.g. dexamethasone), the transcription factor is released from Hsp90 and can drive gene expression.

The components of this system are
i Promoter—toxin ORF
ii Promoter-transcription factor ORF
iii Transcription factor-responsive promoter—antidote ORF Suitably, the tapetum-specific A9 promoter may be used. The tapetum is a tissue required for production of functional pollen. The system is then 'off' in all tissues except the tapetum. In the tapetum, the toxin and the transcription factor are both expressed. In presence of the inducer (here dexamethasone), the antidote is also expressed. So plants treated with dexamethasone are normal, but those not treated with dexamethasone produce no pollen.

Suitably barnase and barstar (Hartley, R W, 1988, J. Mol. Biol. 202:913, Hartley, R W, T.I.B.S. 14: 450-454, 1989) may be used as toxin and antidote, respectively. However, while Barnase and Barstar are suitable examples of a toxin/repressor pair, the invention is not so limited, and a suitable repressor could act at a transcriptional (or other) level, and the toxin itself does not have to be a protein.

It is the lethal effect of the lethal system which is conditional, and not solely the expression of the lethal gene. Therefore, the invention includes the possibility of conditional control both at the level of lethal gene expression, and by control of the activity of the lethal gene product. As such, the invention includes the case in which the lethal gene product is being produced but the effect of which is masked in some way.

We prefer that the method of the invention uses only organisms with a single conditional dominant lethal genetic system. In addition, we prefer that this system is the only recombinant element present in the organism. We particularly prefer that the organism contains only one type of lethal gene, but it is possible to envisage multiple lethal genes under the same regulatory control, giving the integrated genetic construct concept but a more efficient lethality of the system. This single lethal gene may be under the control of just one promoter in the genetic system, or more than one promoter.

The organism of the invention is preferably recombinant, which refers generally to any organism whose genetic material has been altered by genetic manipulation. We prefer that the organism is modified by insertion of a gene, gene fragment or genetic element (such as a promoter or enhancer) from another species, to produce a transgenic organism. The transgenic component is generally the lethal system which produces a conditional lethal effect. However, a conditional lethal effect may also be generated using genetic components derived from the same (host) species. For example, a promoter derived from a different gene in the same species, when placed in front of a gene which is only normally expressed at low levels, may result in a lethal effect. The recombinant organism is thus either a transgenic organism or one in which the host genetic material has been modified to produce a lethal system.

The multicellular organism may be any organism, such as a plant or animal. Indeed, the invention is generally only limited to those organisms having a sexual component in their life cycle, which enables the lethal system to be transferred from one organism to another. For example, the invention is also applicable to fish, such as the sea lamprey, against which sterile male release techniques have been employed. We particularly prefer that the multicellular organism of the invention is an insect, with insect pests being particularly preferred. An insect pest may be either a direct or an indirect pest. Direct pests are those insects which cause damage at one or more stage of their life cycle by, for example, eating crops or damaging animals. The New World screw-worm fly *Cochliomyia hominivorax*, for example, is a direct pest of cattle. Indirect pests are those insects which are vectors of human diseases, such as mosquitoes which carry malaria. Indirect pests of organisms other than humans, such as livestock or plants are also known.

Preferred insect targets for the present invention include Crop (arable and forestry) pests animal pests and disease vectors. Examples of specific organisms which potentially may be used in the present invention include, but are not limited to: Australian sheep blowfly (*Lucilia cuprina*, Asian tiger mosquito (*Aedes albopictus*); Japanese beetle (*Popilla japonica*), White-fringed beetle (*Graphognatus* spp.), Citrus blackfly (*Aleurocanthus woglumi*), Oriental fruit fly (*Dacus dorsalis*), Olive fruit fly (*Dacus oleae*), tropical fruit fly (*Dacus cucurbitae, Dacus zonatus*), Mediterranean fruit fly (*Ceratitis capitata*), Natal fruit fly (*Ceratitis rosa*), Chemy fruit fly (*Rhagoletis cerasi*), Queensland fruit fly (*Bactrocera tryoni*), Caribbean fruit fly (*Anastrepha suspensa*), imported fire ants (*Solenopis richteri, Solenopis invicta*), Gypsy moth (*Lymantria dispar*), Codling moth (*Cydia pomonella*), Brown tail moth (*Euproctis chrysorrhoea*), yellow fever mosquito (*Aedes aegypti*), malaria mosquitoes (*Anopheles gambiae, Anopheles stephansi*), New world screwworm (*Cochliomyia hominivorax*), Old World Screwworm (*Chrysomya bezziana*), Tsetse fly (*Glossina* spp), Boll weevil (*Anthonomous grandis*), Damsel fly (*Enallagma hageni*), Dragonfly (*Libellula luctuosa*), and rice stem borer (*Tryporyza incertulas*). Reviews discussing the suitability of many of the above are: C. Boake et al., (1996) Annu. Rev. Entomol. 41: 211-219, J. Meyers et al., (1998) Annu. Rev. Entomol. 43: 471-491, C. Calkins et al., (1994) Fruit flies and the sterile insect technique. CRC Press. ISBN 0849348544, E. Krafsur et al., (1997) Annu. Rev. Entomol. 42: 503-523 and R. de Shazo et al., (1994) J. Allergy Clin. Immunol. 93(5): 847-850. It will be understood that the present invention is generally applicable to all multicellular organisms capable of sexual reproduction, such as plants and animals.

For all animals, the transgenic stock is released into the environment at appropriate sites and times. For plants, where the adults are not mobile, the procedure is slightly different. Either the gametes themselves are released, e.g. as pollen, or plants are dispersed, e.g. at field margins, to pollinate wild weeds and so reduce their reproductive potential. The present invention is of particular use in the control of those weeds, such as rye grass, which are not well controlled by current herbicides, or against weed types which have developed herbicide tolerance.

Not all of the terms which are used to describe, for example, plants are applicable to animals or vice versa. However, the principles of the invention as laid out in relation to one species may readily be applied to other species by a person skilled in the art. For example, where the terms 'female' and 'male' are used in relation to insects, these may also refer to plants having only viable female or male tissues respectively, where appropriate. The term 'sex separation' also may refer to plants which have been separated on the basis of their viable sex tissues from other plants.

The invention is preferably such that expression of the lethal genetic system will always occur in the environment in which the organism is released for biological control, and is unaffected by natural variation in environmental factors. In this way, biological control is always achievable using the present invention, irrespective of the site of release, time of release, or any other environmental conditions. Where the factor controlling conditional expression is artificial, then it is immediately clear such a factor cannot, by definition occur in the natural environment. The present invention is essentially pandemic, in the sense that it may be universally applied over the whole of a country or the world environment.

Essentially any natural environment itself provides the restrictive conditions for the organism, resulting in the biological control. As such the restrictive conditions are guaranteed to occur upon organism release, and there is no concern that local environmental conditions will affect the action of the lethal system. Preferably the natural environment of the organism provides the absence of a controlling factor or condition, which then results in expression of the lethal genetic system in the environment.

The multicellular organism of the present invention preferably has a lethal system homozygous at one or more loci. In the situation where there is one homozygous copy of the lethal system, then at least one copy of the system will be passed to any offspring during sexual reproduction. Therefore, the dominant lethal effect will be exerted, except in permissive conditions. The present invention may be carried out using a heterozygote for the dominant lethal system. However, in this case, not all the offspring will have a copy of the lethal system, and the effect on the population is reduced.

It is preferred that all the elements of the genetic system are present on the same chromosome, in close proximity. In this way, it is likely that all elements of the lethal system are passed on to subsequent generations. However, the lethal system can also function when controlling elements are present at different genetic loci to the lethal gene, if controlling effects of these elements are exerted in trans, for example. In that event, the genetic system is still effective if the controlling and lethal elements are also homozygous, and at least one copy of each is transferred to the offspring.

In one aspect the invention relates to a non sex-specific system, in which both males and females are killed by the lethal genetic system. Such an approach is preferred in certain organisms. In such a case, one advantage of the invention lies in the avoidance of sterilisation by irradiation. By way of example, mixed sex releases are preferred in pink bollworm (a lepidopteran pest of cotton), but irradiated moths are estimated to suffer at least a 10 fold reduction in effectiveness as a consequence of the irradiation due to loss of vigour and reduced life span. Similar advantages are predicted in other organisms. In medfly, irradiated males are about 50% less effective than the non-irradiated equivalent in competitive mating tests and they live 3-5 days instead of the non-irradiated 10-15. This gives a composite 4-10 fold potential performance improvement by avoiding irradiation.

The method of the invention alternatively uses a sex-specific lethal system to achieve sex separation before or after release of organisms into the environment. In a preferred embodiment, the multicellular organism is an insect containing a homozygous dominant lethal system, the lethal effect of which is lethal only to females. In this embodiment males released into the natural environment will not be killed. After mating with females, female offspring will contain at least one copy of the dominant system and be killed. However, male offspring, 50% of which contain the dominant system, are viable and may mate with further females. In this way, the dominant system may be transmitted to subsequent generations, although without further artificial introductions the system will eventually be lost from the gene pool.

In the case in which a male contains a lethal genetic system with a female specific lethal effect, then males released into the environment will not be killed. However, the lethal effect of the lethal system is still manifested in the natural environment—even if this effect is limited to females.

Sex-specific lethality may be achieved in a number of different ways. For example, it is possible to use a sex-specific lethal gene as part of the lethal system, whose gene product is toxic only in one sex. This approach will allow killing of a single sex even if expression of the lethal gene of gene product is not sex specific. Candidates for female sex-specific lethal genes include genes from the sex determination pathway, for example normally active only in males and toxic in females, or genes derived from sexual differentiation or gametogenesis systems.

Alternatively, expression of the lethal gene or gene product may be controlled so that it is expressed or produced only in one sex (or in only one gamete or sexual organ of a hermaphrodite). For example, sex-specific promoters or enhancers may be used, either in combination with sex-specific lethal genes or non-specific lethal genes. Sex-specific splicing provides another mode for sex-specific gene expression. All possible combinations of non-specific lethal genes, sex-specific lethal genes, non-specific promoters and sex-specific promoters are envisaged by the present invention. In addition, other sex-specific factors which control the lethal effect of the lethal gene are included in the present invention.

The present invention also includes a method of biological control in which the lethal effect may be sex-specific at one stage of the life cycle, but be lethal to both sexes at another stage. For example, the lethal system may be female specific in an adult organism, but be lethal to both males and females in the larval stage. In such a case, one sex may be killed by expression of the lethal system in the adult form. When the organism then breeds in the wild, passing on the genetic construct, then both males and females can be killed. Such an effect can be achieved by a promoter which is sex specific at one life cycle stage, but not at another, or by placing the lethal gene under control of two different promoters, for example. Multiple lethal systems might also be employed.

For example, a lethal effect manifested at an embryonic or larval stage will not affect adult organisms, if they are grown under permissive conditions through this stage. As such, organisms may be distributed into the environment after the lethal life cycle stage, allowing the lethal system to be passed into the wild-type population through sexual reproduction. Other life cycle stages, such as the adult stage, may also be targeted by selection of genes or promoters expressed at specific life cycle stages, if appropriate.

We prefer that the multicellular organism of the present invention has a copy of the lethal genetic system at more than one locus. Preferably, the lethal system is homozygous at more than one locus.

Multiple copies of the lethal system are useful to enhance the effect of the invention. For example, if the organism is homozygous at one locus for a female specific lethal system, any females that result from mating of the organism with wild type females will be killed. Male offspring will survive, and carry one copy of the system. Only 50% of the next (second) generation of male offspring will carry the lethal system.

The approach will clearly be more effective if more than 50% of this next (second) generation of male offspring were to inherit the lethal genetic system. There are several ways of achieving this. For example, if the lethal genetic system is homozygous at more than one, not tightly linked locus, e.g. on more than one chromosome, then the proportion of these males carrying the lethal genetic system will increase. Specifically, with the lethal genetic system homozygous at two unlinked loci, the first generation males will be heterozygous at both loci, 75% of the second generation males will carry at least one copy of the lethal genetic system. Correspondingly, under restrictive conditions all of the first generation and 75% of the second generation females will die.

Another way of achieving this effect is to use a segregation distortion/meiotic drive system. In the *Drosophila* SD system, the SD chromosome is preferentially inherited from males heterozygous for SD and a normal (+) SD-sensitive chromosome. SD/+ males transmit SD-bearing, to the virtual exclusion of +-bearing, homologues; as many as 99% of the functional sperm may carry SD. Segregation distortion/meiotic drive systems are known in a wide range of insect and non-insect species.

A third way of ensuring >50% inheritance of the lethal genetic system in the second generation is to link the lethal genetic system to insecticide resistance and use the insecticide to eliminate some or all of the second (and subsequent) generation progeny which do not carry the lethal genetic system and hence do not carry the linked resistance gene.

The lethal system may be located on any chromosome, either an autosome or sex chromosome. In species where sex is determined by the X or Y chromosome content and where elimination of the transgene from the gene pool is desired, then we prefer that the lethal system is located on the X chromosome. Consider the case in which the lethal system is specific for females. A male organism (XY) having the lethal system on the X chromosome mates in the wild with a female wild type organism (XX). The male offspring must derive their Y chromosome from the recombinant male and their X chromosome from their mother. These males are viable and have no lethal gene. Female offspring must derive one X chromosome from the recombinant male and, thus, contain the lethal genetic system—they are killed. As such, the lethal system is eliminated from the gene pool, which may be preferable if this element is a transgene.

The present technology also provides a method for the selection of males or females per se, comprising producing a organism as described herein containing a conditional dominant lethal system, wherein the lethal effect of the lethal system is sex-specific. Sex selection is achieved by allowing expression of the lethal effect of the lethal system, to eliminate one sex. The individual male or female population may then be used for any desired purpose, not being limited to biological control.

The present invention also relates to a method of producing a recombinant multicellular organism for use in the present invention, wherein the organism is transformed with a vector or vectors containing a dominant lethal system, or a suitable sequence for site specific mutation.

The present invention further relates to a vector or vectors comprising a dominant lethal system as described herein.

We prefer that all the required elements to control the expression of the dominant lethal gene are present on a single transformation construct (vector). In this way, only a single transformation step, and single transformation marker, are required. In addition, use of a single transformation construct helps prevent recombination of separate elements of the lethal genetic system. Therefore, preferred is a single vector comprising any conditional dominant lethal genetic system of the invention.

Further preferred are vectors comprising the conditional dominant lethal genetic system of the invention, wherein the components of the vector (such as the genes or regulatory elements, in particular the lethal gene) are genetically insulated from one another. Preferably there is no cis cross-talk between the different elements of the lethal genetic system of the vector. Preferred are vectors in which the components of the lethal genetic system are separated from one another by insulator sequences derived from vertebrate DNA which prevent such cross-talk. Such insulators have been reported to work in Drosophila, for example [Namciu, S. J., et al., (1998) Mol. Cell. Biol. 18: 2382-91 and Chung, J H., et al., (1993) Cell 74:505-514], and by extension are likely to be effective in other insect species at least.

In a preferred embodiment, the vector of the invention comprises a tetracycline repressible system. Preferably a lethal gene is located on the same DNA sequence or vector as this system, optionally with a reporter gene. A suitable tetracycline based lethal system comprises two key components, a lethal gene and a tTA gene which activates expression of the lethal gene. Tetracycline, or analogue thereof, then blocks activation of the lethal gene by the tTA. In this case, we prefer that enhancer-blocking insulators are used to isolate one component from the next, namely the lethal gene from the tTa, the lethal gene from the reporter and the tTa from the reporter gene.

A particularly preferred vector in which the genetic elements are separated and modular is presented in the Example 7 herein. This vector comprises a dominant lethal tetracycline-repressible genetic system, wherein at least some of the genetic components of the system are separated by genetic insulator sequences. The lethal gene is the Nipp gene from Drosophila.

This modular vector may be adapted by replacing the BmA$^3$ promoter with any suitable promoter to allow the construct to be used in any organism of interest. As such the invention provides a modular template vector as described herein, where the BmA$^3$ promoter module may be replaced by any promoter, for use in any suitable organism.

The invention also extends to variants of this specific modular vector, in which the functional elements have been replaced with other elements which perform equivalent functions, such as other insulators or lethal genes, and to DNA encoding such variants.

The invention also relates to a method of constructing a vector appropriate for imparting a dominant lethal genetic system to an organism, comprising the steps of:
 i providing at least one conditional lethal genetic system;
 ii choosing a promoter appropriate for expression of the system in the organism; and
 iii ligating the promoter and conditional lethal genetic system, optionally with other components, to produce a functional vector suitable for transformation;
  wherein transformation of the vector into the organism produces an organism for biological control according to the invention.

Preferably the lethal genetic system of the vector is modular in that there are components which can be individually replaced by functionally equivalent genetic components, appropriate for the lethal system to function in an organism of interest. For example, such a modular vector allows the lethal gene or promoter sequences to be replaced, for example, without the need to generate an entirely new vector. Suitably the individual genetic components may be separated by insulator sequences and still function together to cause a lethal effect. Preferably the vector comprises at least one insulator sequence, preferably two such sequences.

The invention also relates to vectors obtained and obtainable by the above method.

The present invention also extends to polynucleotide sequences encoding a conditional dominant lethal genetic system according to the present invention, preferably being a DNA sequence. In particular the invention relates to DNA encoding the lethal genetic system of the Examples, in particular the modular transformation vector of Example 7 herein, and to mutants and variants of such DNA having minor changes such as substitutions, deletions or additions, but wherein the function of the vector or lethal genetic system are not substantially affected, and the vector is able to cause the lethal effect of the invention as required.

Alternatively, multiple vectors may be used to transform the organism with the necessary elements of the lethal system, if necessary. It is also possible that control elements and enhancers used to control, for example, a transcription factor which acts on the lethal gene, may also interfere with the lethal gene expression itself. It may, therefore, be necessary to separate the components using silencer elements, or other genetic insulating elements to avoid unwanted gene expression problems.

The effect of a promoter or enhancer upon a gene normally requires the elements to be present on the same stretch of DNA. However, the effect of a transcription factor may be exerted in trans, and may be located on, for example, a different chromosome. The invention is not limited to integration of the controlling elements on the same chromosome.

The construction of a recombinant multicellular organism may require use of a transformation system for the target species (the species which is to be controlled). The specific nature of the transformation system is not a critical feature of the invention, and transformation protocols for a number of, for example, insects are already known.

Vectors may be constructed using standard molecular biology techniques in bacteria such as E. coli. We prefer that the vector used for transformation contains a selectable marker, such as genes producing G418 resistance or hygromycin resistance. Alternative genes other than those related to antibiotic resistance characteristics, such as green fluorescent protein (GFP) may also be used. Expressed under the control of a suitable promoter, this protein can be visualised simply by illuminating with a suitable excitatory wavelength (e.g. blue) and observing the fluorescence. Such a marker would also allow easy identification of trapped insects in release-and-recapture experiments.

Other suitable markers for transformation are well known to the person skilled in the art.

The invention also extends to cells, such as bacterial cells, transformed with a vector of the invention. Suitable cell lines for maintenance and/or propagation of such vectors, for example, are well known to the person skilled in the art.

We prefer that deletion of all or part of the lethal genetic system of the present invention from an organism gives no selective advantage over an organism containing the system in permissive conditions. The use of a lethal genetic system as described herein has significant advantages with respect to strain stability. In general, cross-mobilisation between related transposons and/or other unknown mechanisms can mean that transposon insertions may not be as stable as "real" genes. When reared at a level of billions/week, as may be required for biological control, even extremely rare events will happen repeatedly. This is a major issue with the current medfly sexing strains where the chromosome translocations on which they depend break down (at a low frequency). Unfortunately, the resulting flies have significantly higher fitness than the rest of the stock and so their numbers tend to increase rapidly. However, in the present system the breakdown product (deletion of all or part of the transposon) has no great advantage over the intended stock, when reared on media containing Tc. Moreover, where there are multiple insertions, it would take several independent events (i.e. loss of each insertion), to make the stock completely ineffective.

If necessary, the lethal genetic complex may be further stabilised. Suitable methods include deleting one end of the transposon after integration or secondary mobilisation of the system out of the transposon into another site, using a site-specific recombination system such as FRT/Flp or cre/lox. Both of these systems are known to work in *Drosophila*.

Figure 2A:
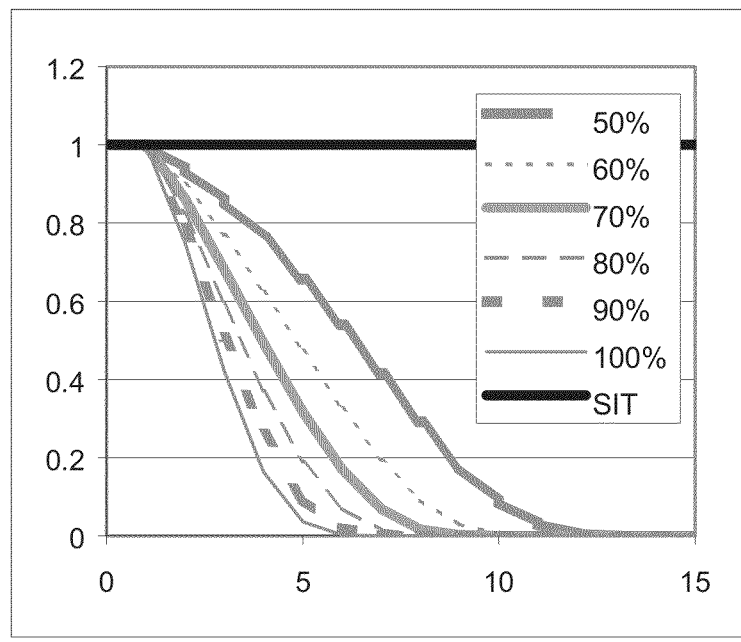
Figure 2B:
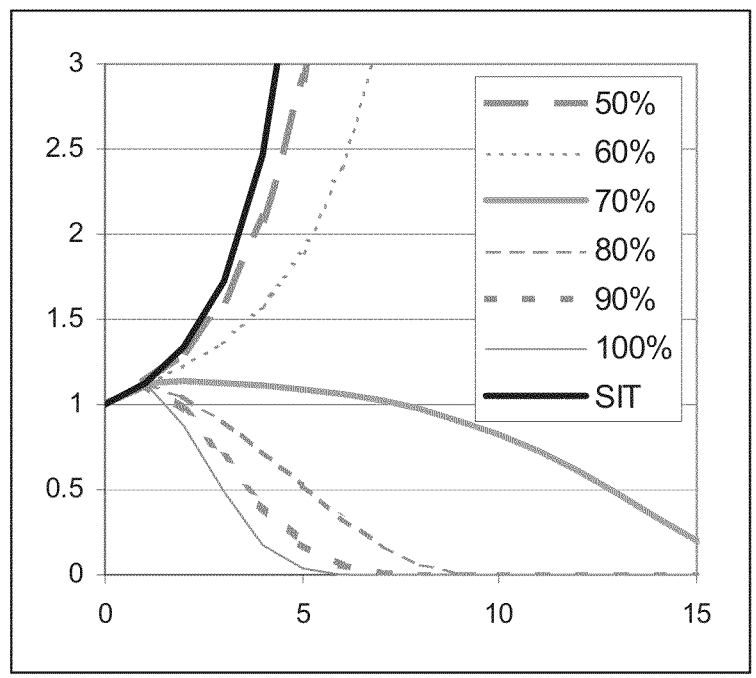
Figure 3A:
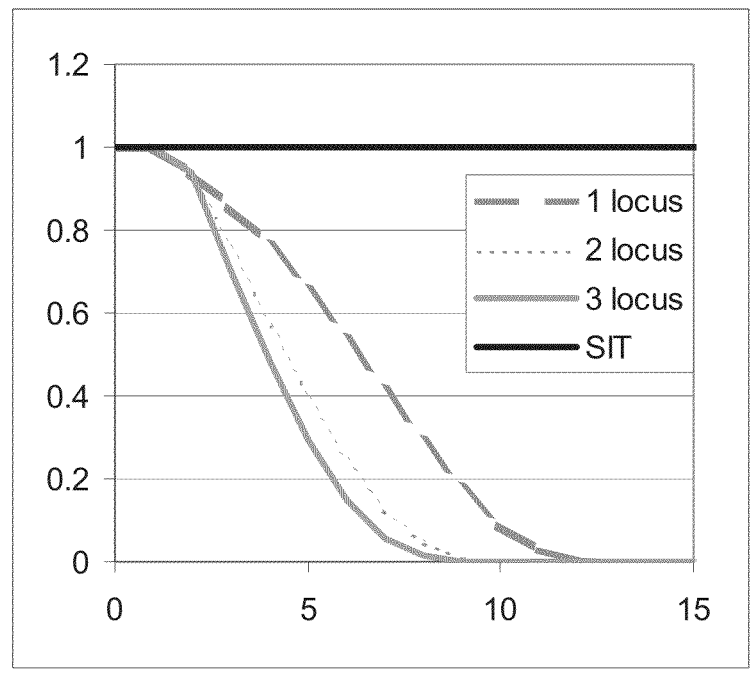
Figure 3B:
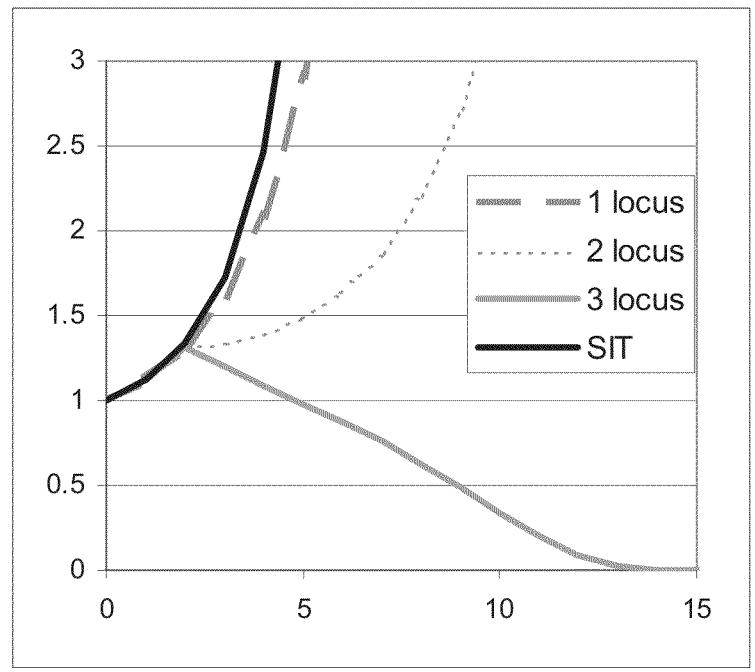
Figure 4A:
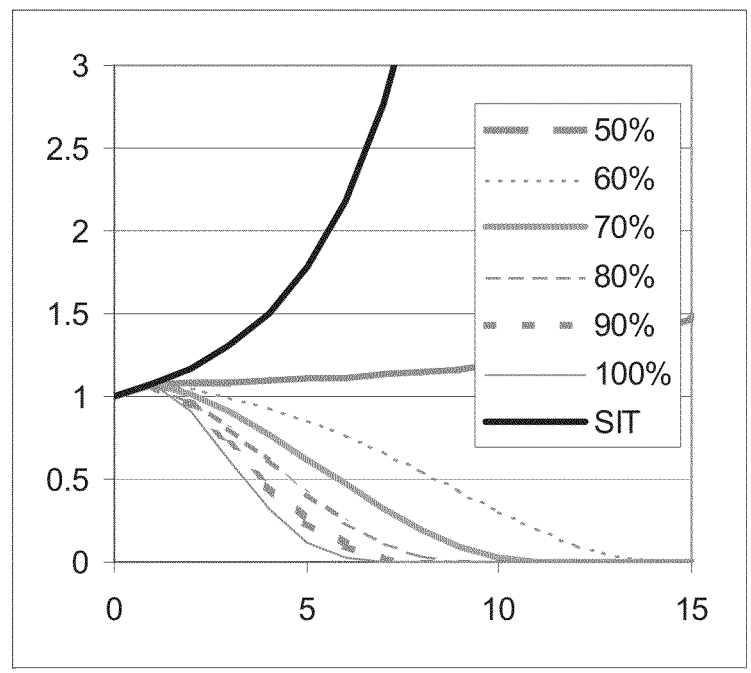
Figure 4B:
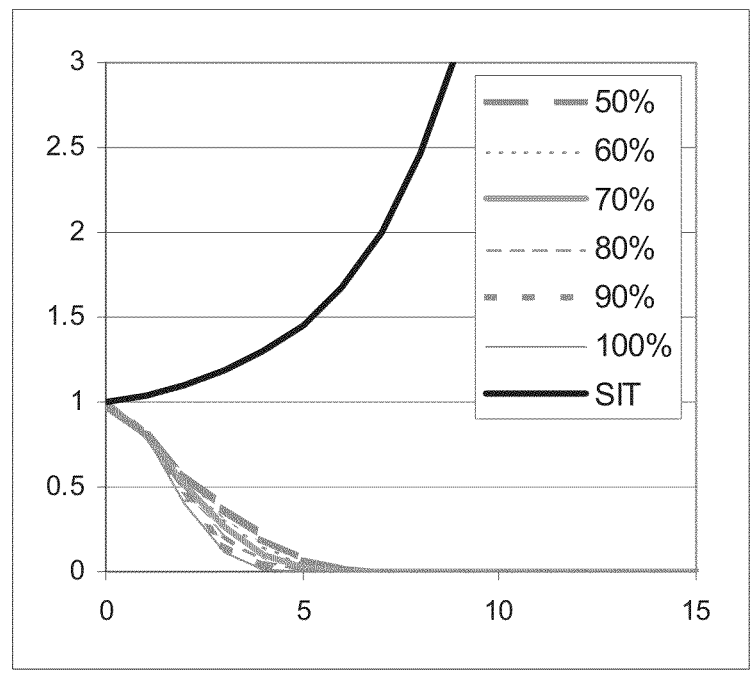
Figure 5A:
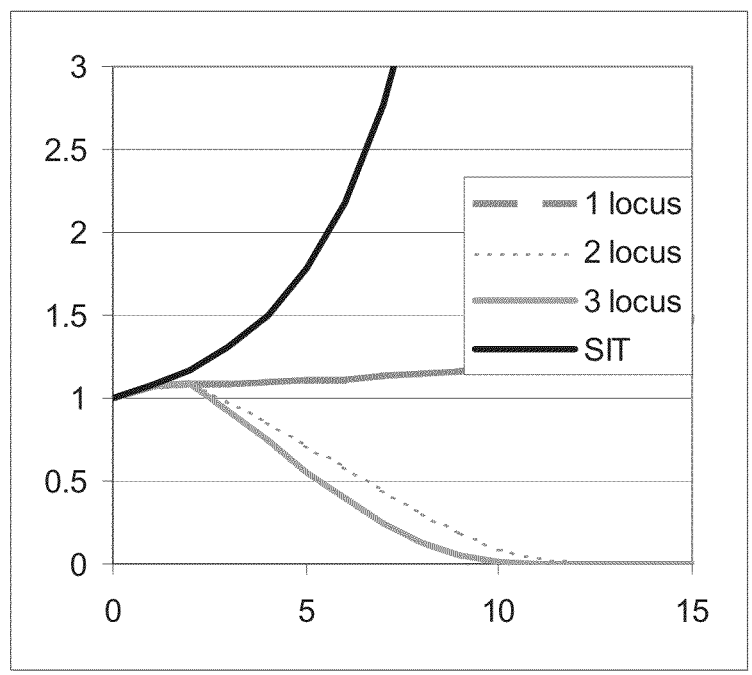
Figure 5B:
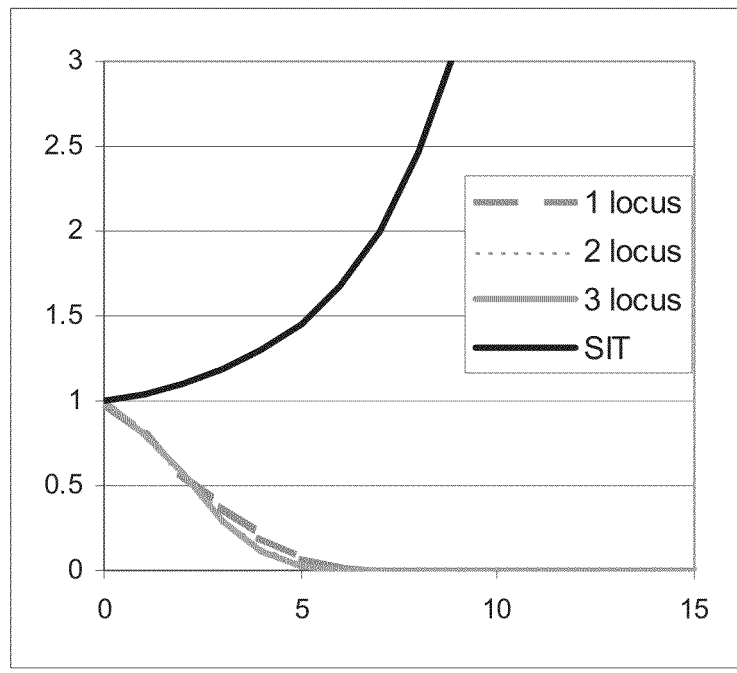
Figure 6A:
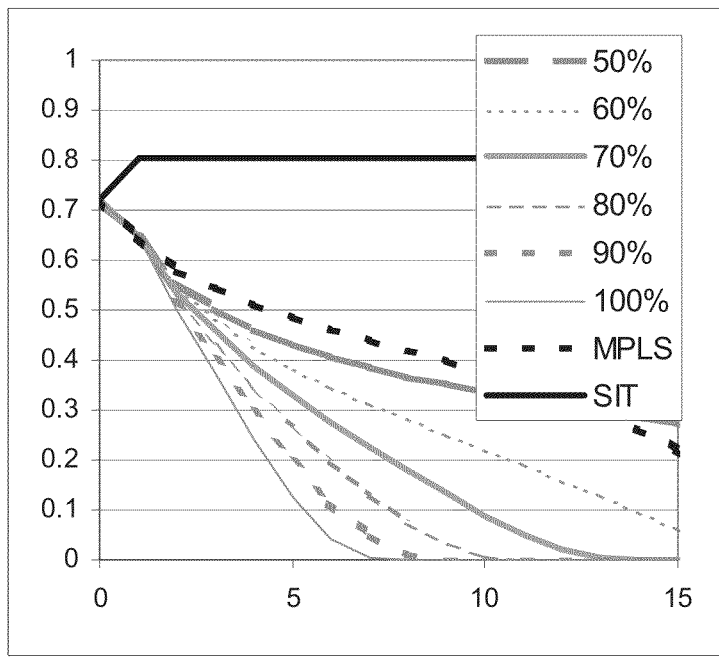
Figure 6B:
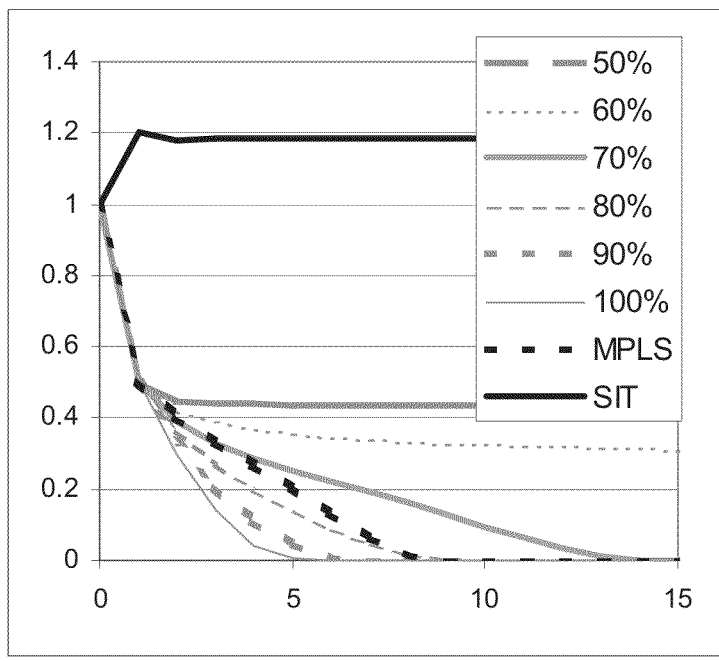
Figure 6C:
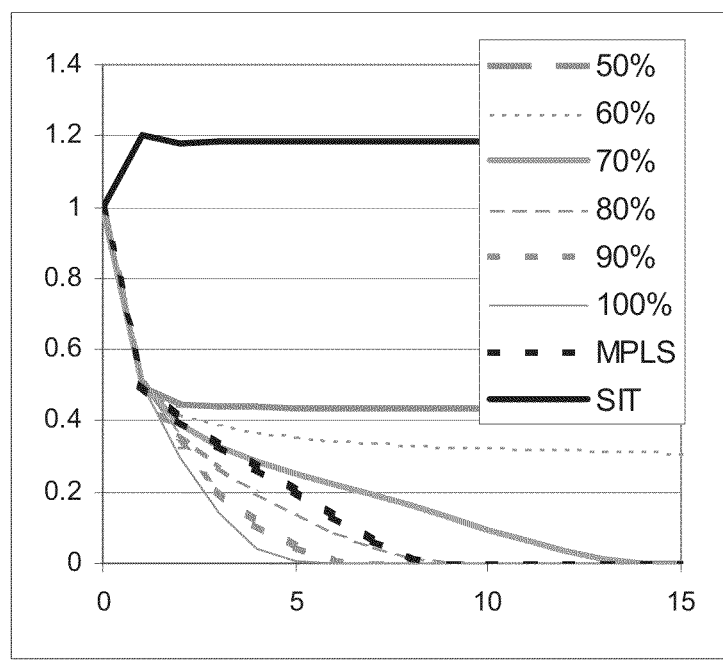
Figure 7A:
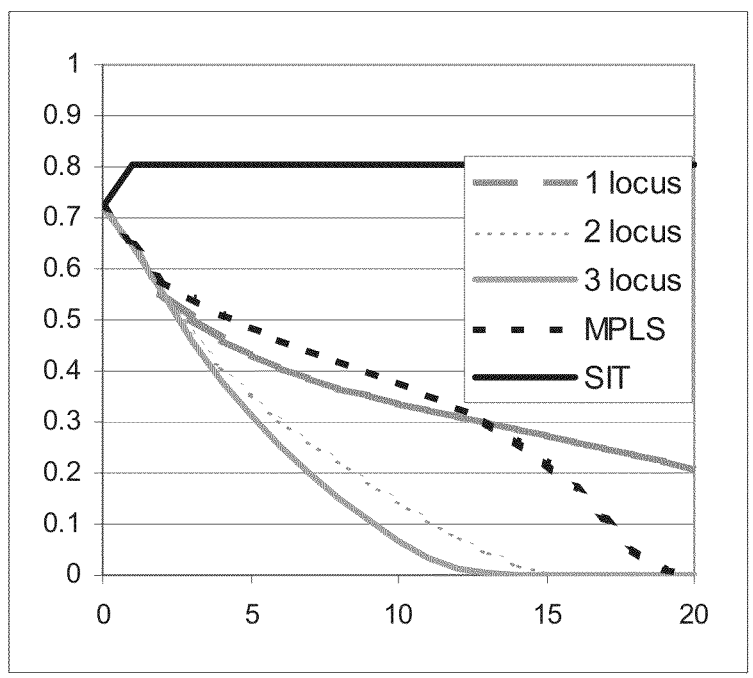
Figure 7B:
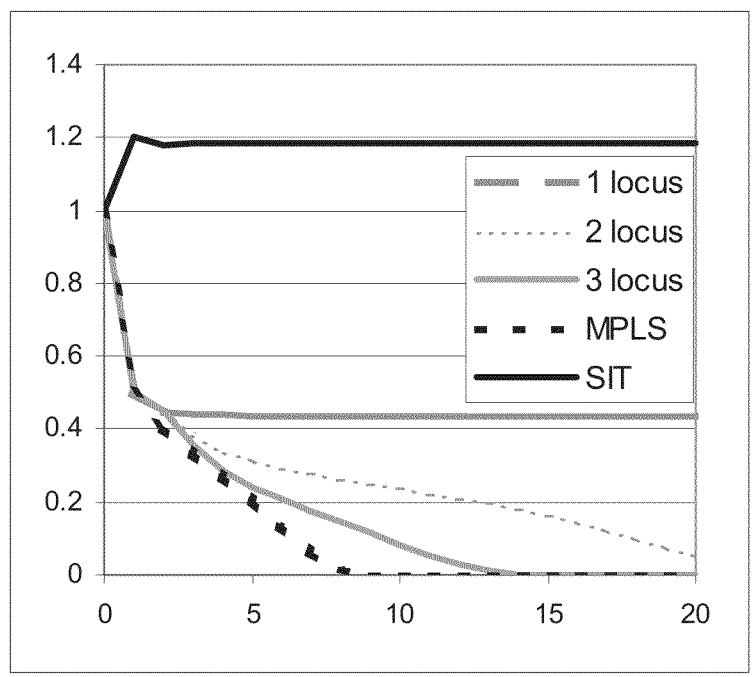
Figure 7C:
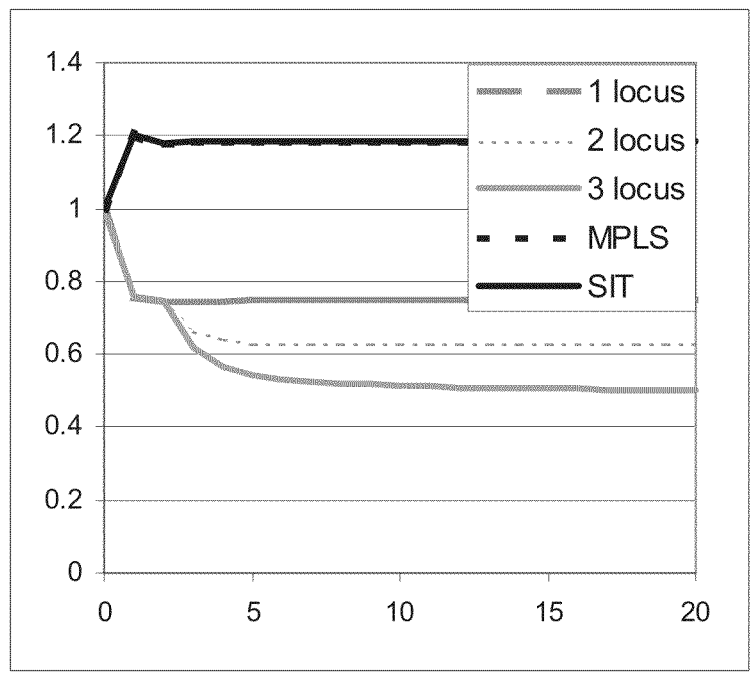
Figure 8A:
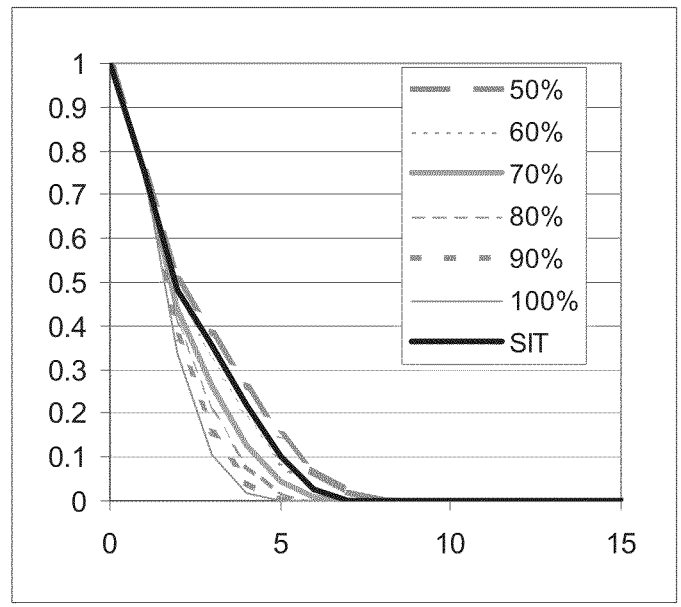
Figure 8B:
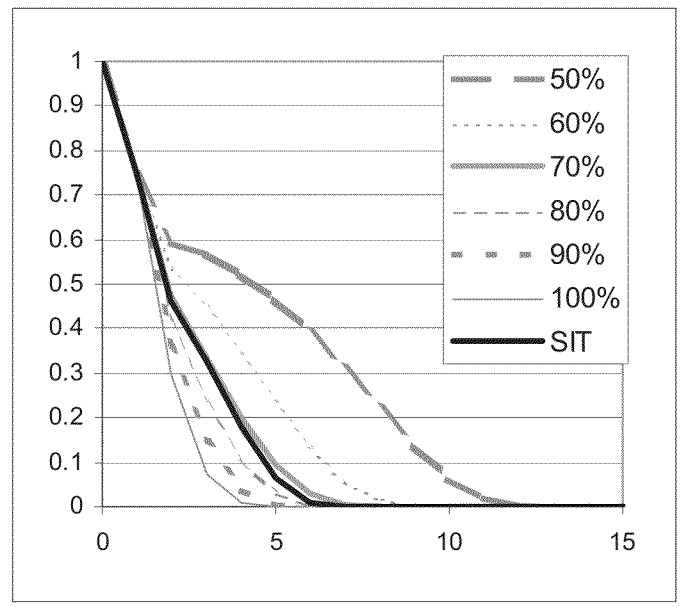
Figure 8C:
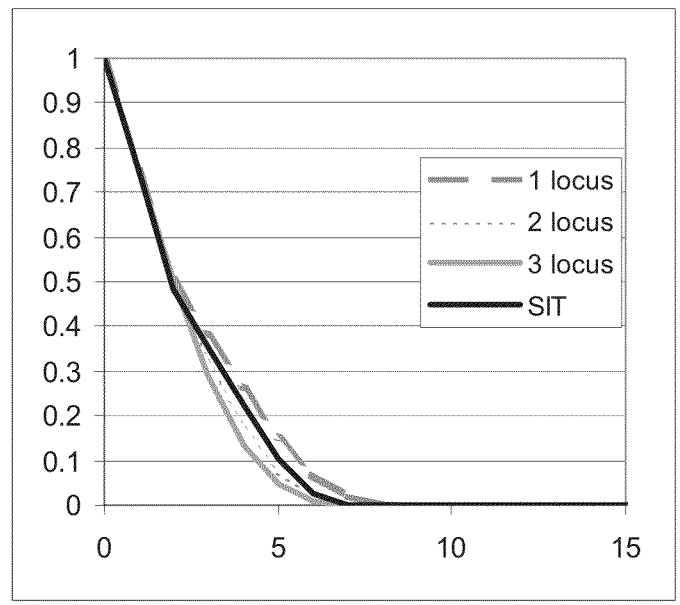
Figure 8D:
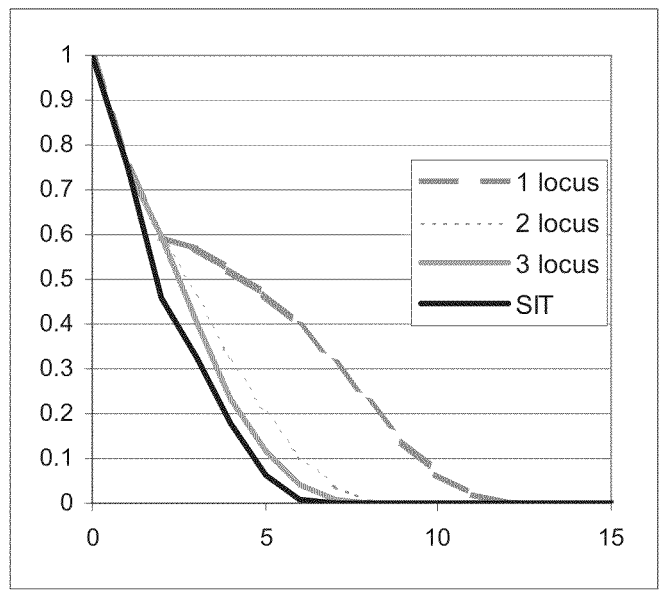
Figure 8E:
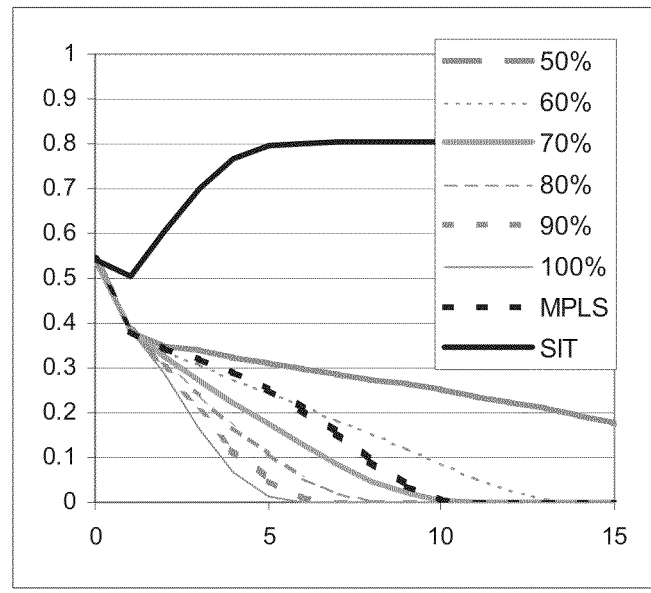
Figure 8F:
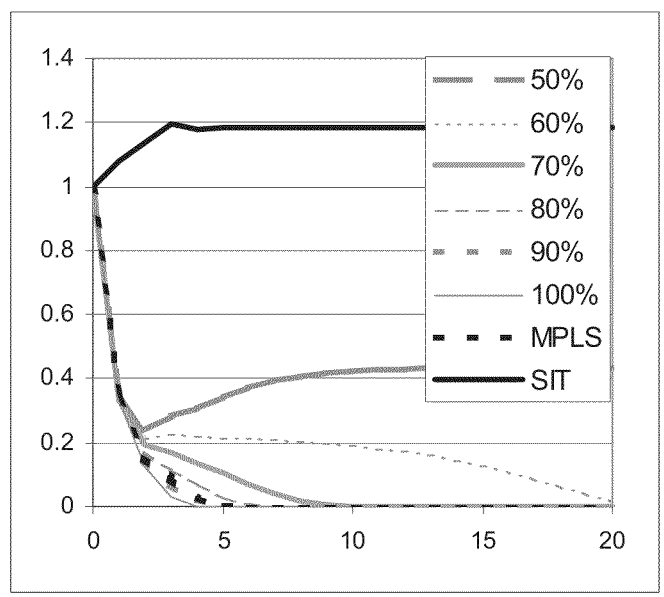
Figure 8G:
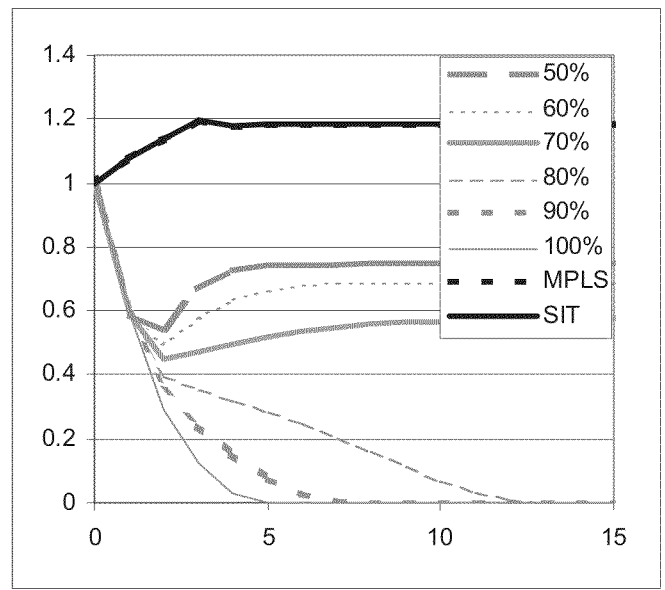
Figure 8H:
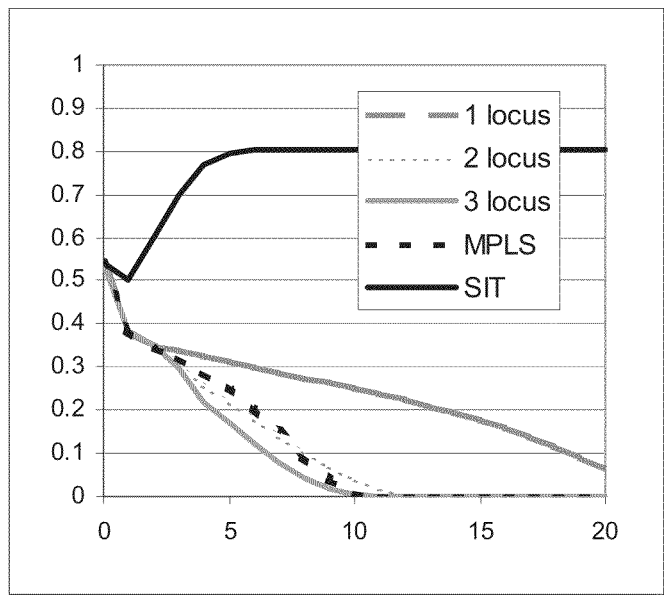
Figure 8I:
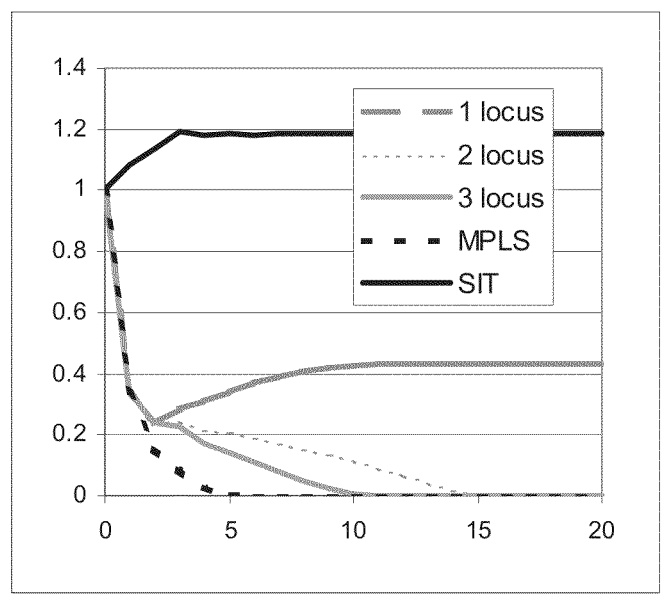
Figure 8J:
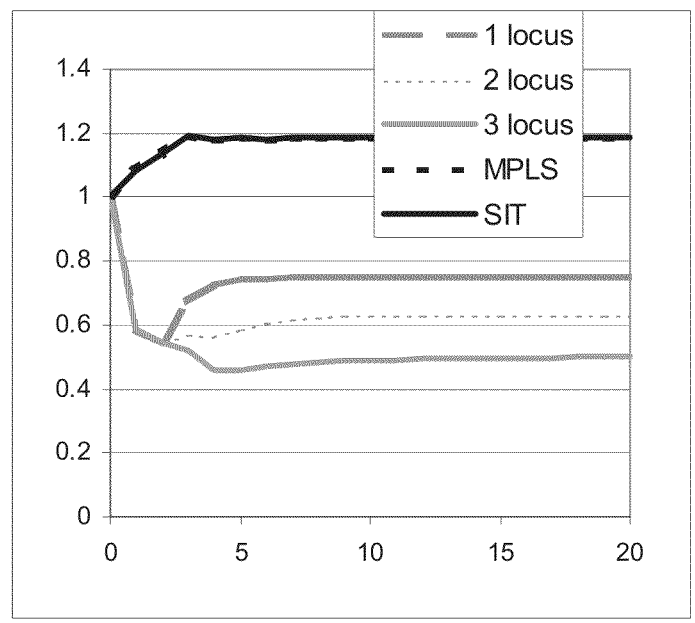

The present invention will now be illustrated with respect to the following Examples, which are for illustrative purposes only and are not limiting upon the present invention, wherein:

FIG. 1 illustrates a modular vector for organism transformation;

FIG. 2a-b illustrates a model of a meiotic drive system of the present invention;

FIG. 3a-b illustrates a model of population control using multiple unlinked loci;

FIG. 4a-b illustrates a model of a meiotic drive system according to the present invention;

FIG. 5a-b illustrates a model of population control using multiple unlinked loci;

FIG. 6a-c illustrates a further model of a meiotic drive system of the present invention;

FIG. 7a-c illustrates model of population control using multiple unlinked loci; and FIG. 8a-j illustrates models of population control using the parameters of FIGS. 2, 6 and 7, but wherein the first two releases are doubled in size.

EXAMPLES

Biological Control in a Drosophila Model

Introduction

In one specific embodiment, a two-part system may be used to produce a conditional lethal effect. This system is based upon the repressor (tetR) of the transposon-1-derived tetracycline (Tc) resistance operon of *E. coli*. The use of this repressor for repressible gene expression in eukaryotes has been developed by Manfred Gossen and Hermann Bujard (reviewed in Gossen, et al., TIBS 18 471-475 1993). In this system, the tetR gene product is fused to the acidic domain of VP16, to create a highly efficient Tc-repressible transactivator (tTA).

The first part of the system is the tTA expressed under the control of a suitable promoter, and the second part is a dominant lethal gene expressed under the control of the tTA. Overall, this gives expression of the dominant lethal in a Tc-repressible fashion. When tetracycline is not available, the tTA activates the lethal gene. When tetracycline is present, it binds to the tTA and prevents activation of the lethal gene by tTA. This lethal system is under the control of a promoter of choice. One further level of control can be exerted by the choice of which Tc-analogue to use for repression: different analogues will have different half-lives in the insect leading to induction of the killer gene more or less promptly after the repressor is withdrawn from the diet.

We prefer that a non-bactericidal analogue should be used, so as not to encourage tetracycline resistance in environmental micro-organisms. Use of a non-bactericidal analogue is in any case essential for species such as tsetse fly, which have symbiotic bacteria essential for reproduction of the fly which are killed by antibiotics.

Even this one system may be varied to provide a flexible tool for population control. Greater flexibility may be achieved by combining two or more promoters or enhancers. For example, medfly control might use expression in the adult female (to prevent release of egg-laying females), and in early embryonic development (to prevent larval growth within the fruit). Since this means expression before the embryo starts to feed for itself, it would be important for growing the stock that a relatively stable Tc analogue is used, so that the embryos survive because of the maternal contribution of Tc. Larval expression could be also used as an alternative, but with greater damage to the fruit.

Use of the above system to control the lethal effect of the lethal gene is only one example of how an effect could be achieved, and there are numerous promoters, transactivators and lethal genes, for example, which could be used to achieve the desired effect.

In the above scenario expression at more than one stage may be required. This could be achieved by using two separate tTA constructs, or by combining stage-specific enhancers into a single construct. Appropriate promoters for stage-specific expression may be identified by subtractive hybridisation or other known methods.

Insertion of the lethal gene or system into the chromosome of the transgenic organism may be at any suitable point. It is not necessary to determine the location of the lethal gene on the chromosome. Even though inserted elements may respond to control elements in adjacent chromatin, this not an issue for the tRE-killer lines, where lines giving inappropriate expression will probably not survive.

The present invention has been exemplified in the model insect species *Drosophila melanogaster*. Though *D. melanogaster* is not an economically important pest, it is experimentally tractable. The tTA system in general has been demonstrated in *Drosophila* (Bello, B., et al., 1998, Development 125:2193-2202). The Hsp26-tTA and tRE-lacZ used below, and some vectors [described below], came from this paper.
Components:
Transactivator Component (Promoter—tTA)
Hsp26-tTA: Heat shock protein 26-tTA. Low basal level, heat-shock inducible to higher level, not sex-specific.
Obtained from Bruno Bello (NIMR, London). As detailed in Bello et al. (1998) Development 125, 2193-2202. Hsp26 promoter region with a portion of the translated region (sequences from −1917 to +490) was fused to a tTa coding region isolated as an EcoRI/BamHI fragment from pUHD 15-1.neo followed by the transcription termination sequence of the Hsp70 gene.
Act5C-tTA: Actin 5C-tTA. Strong, constitutive, ubiquitous promoter, not sex-specific.
The tTA coding region was excised as an EcoRI/PvuII fragment then end filled using T4 DNA polymerase. The p CaSpeR {Actin5C GFP} (Reichhart and Ferrandon, (1998), D. I. S. 81: 201-202) was digested with XbaI/BamHI to remove the GFP fragment then end filled using T4 polymerase. These two fragments were then ligated. The resulting clones were screened using a SmaI/EcoRV digest to select a clone of the correct orientation, placing the tTa coding region under the control of the Actin 5C promoter.
Stwl-tTA: Stonewall-tTa. Female-specific in embryos, but expressed later in both sexes.
The tTa coding region was excised from the plasmid pUHD 15-1.neo by digestion with EcoRI and PvuII. This fragment was then ligated into the vector pstwE$^{+mCa}$ (Clark, K. A. and McKearin D. M. (1996), Development 122 (3): 937-950) digested with EcoRI/PvuII such that tTa was placed under the transcriptional control of 1.7 kb of stwl promoter genomic DNA.

Sxl$^{pe}$-tTA: Sex lethal-tTA. Early promoter (PE) from Sxl. Thought to be expressed in early female embryos only.
The tTa coding region was excised from the plasmid pUHD 15-1.neo (Gossen M. and Bujard H. (1992); PNAS, 89, 5547-51) by digestion with EcoRI/PvuII. This fragment was then ligated into the 5-1 sxl$^{pe}$: bluescript (containing Sxl$^{pe}$ sequences (Keyes L N, et al. (1992) Cell. 6; 68(5): 933-43) digested with EcoRI and EcoRV to create sxlpe tTa bluescript. A KpnI/NotI fragment containing the tTa coding region and sxlpe promoter was subcloned into the P element transformation vector pP {W8} (Klemenz et al., (1987) Nucleic Acids Res. 15: 3947-3959) digested with KpnI/NotI to create p(sxl$^{pe}$ tTa).

Yp3-tTA: Yolk protein 3-tTA. Female fat body enhancer (FBE) from yolk protein 3, with hsp70 minimal promoter. Expressed in female fat body in larvae and adults.
The tTa coding region was excised from the plasmid pUHD 15-1.neo by digestion with EcoRI and PvuII. This fragment was then cloned between the EcoRI/PvuII sites of the yp 3 expression construct pFBE (Bownes M, personal communication) such that it was under the transcriptional control of the Female Fat Body Enhancer (FBE) (Ronaldson E, et al. Genet Res. 1995 August; 66(1): 9-17.) and a minimal viral promoter.
tRE—Responsive Gene
tRE-lacZ: *E. coli* lacZ gene, encoding β-galactosidase. Used as reporter. Obtained from Bruno Bello (NIMR, London). As detailed in Bello et al. (1998) Development 125, 2193-2202. The heptameric repeat of the tet operator was isolated as a EcoRI/KpnI fragment from pUHC 13-3 (Gossen M. and Bujard H. (1992); PNAS, 89, 5547-51) and cloned upstream of the P-lacZ fusion of the enhancer-test vector CPLZ (Wharton K A and Crews S T. (1994) Development. 120(12): 3563-9.). CPLZ contains the P element transposase promoter (up to −42 from cap site) and the N-terminal transposase sequence fused in-frame with lacZ and the polyadenylation signal of SV40.

WTP-2 (White-tetO-P Promoter—Vector Containing tRe Sequences)
Obtained from Bruno Bello (NIMR, London). As detailed in Bello et al. (1998) Development 125, 2193-2202. This P-element vector was constructed to express any gene under the control of a tetracycline-responsive promoter. It contains the vector backbone of CPLZ, the heptameric repeat of the tet operator, the P-element promoter and leader sequences from Carnegie 4 (Rubin G M and Spradling A C (1983) Nucleic Acids Res September 24; 11(18): 6341-51) and the polyadenylation signal of SV40.

WTP-3 (Modified WTP-2)
The WTP-2 vector was modified by the addition of two complimentary short oligos 5' UAS ATG+ (AATTGCCAC-CATGGCTCATATGGAATTCAGATCTG) (SEQ ID NO:1) and 3' UAS ATG− (GGCCGCAGATCTGAATTCCATAT-GAGCCATGGTGGGC) (SEQ ID NO:2) into the WTP-2 MCS. The oligos were allowed to anneal and ligated to WTP-2 digested with EcoRI/NotI. These oligos introduced a consensus translation start and several additional cloning sites into the WTP-2 multiple cloning site (MCS).

tRe-EGFP. Encodes a mutant version of Green Fluorescent Protein (GFP), a jellyfish (*Aequoria*) gene encoding a fluorescent protein. The EGFP mutant has two amino acid changes, giving a brighter, more soluble protein. Used as a reporter. The enhanced green fluorescent protein (EGFP, a F64L, S65T mutant derivative of GFP) coding region (Craven et al. (1998) Gene 9; 221(1): 59-68) was isolated as a NcoI/EcoRI fragment from the pP{UAS-EGFP} vector, then end filled with T4 polymerase. pP{UAS-EGFP}. pP{UAS-EGFP} was constructed as follows.
The single NdeI site of pP{UAST} was eliminated by digestion, end-filling and re-ligation, in order to be able to use NdeI in the multiple cloning sites. We then used two oligonucleotides (UAS-ATG+=5' AATTGCCACCATGGCT-CATATGGAATTCAGATCTGC (SEQ ID NO:3) and UAS-ATG-=5' GGCCGCAGATCTGAATTCCATATGAGC-CATGGTGGC) (SEQ ID NO:4), allowed them to anneal and ligated them to EcoRI-NotI digested pP{UAST} (from which the NdeI site had been removed) to make pP{UAS-LP}. We amplified inserts from pGEM-T-EGFP [Craven, 1998, supra] using Pfu polymerase and the oligonucleotides 5' TAGGAG-TAAAGGAGAAGAAC (SEQ ID NO:5) and 5' AATTC-CATATGTTTGTATAGTTCA (SEQ ID NO:6). Each PCR product was gel-purified then incubated with T4 DNA polymerase in the presence of dGTP and dCTP but not dATP or dTTP. This created an NdeI-compatible cohesive end at one end of the fragment and an EcoRI-compatible cohesive end at the other end. These fragments were then subcloned into NdeI-EcoRI digested pP{UAS-LP} pP{UAS-EGFP}.

The WTP-3 vector was then digested with EcoRI and end filled with T4 polymerase and the fragments ligated together. A diagnostic digest using PvuII/BamHI, was then used to select a clone of the correct orientation.

tRe-Ras64B$^{V12}$. Mutant version of *Drosophila melanogaster* Ras64B, involved in cell signalling. Mutant is constitutively active, making it toxic to the cell if expressed at a high enough level. Toxicity is not sex-specific. The Ras64B$^{V12}$ cDNA was cloned as an EcoRI/NotI fragment from the p {sevRas64B$^{V12}$} (Matsuo et al., (1997), Development 124 (14): 2671-2680), into WTP-2 digested with EcoRI/NotI.

tRe-Msl-1$^{Mpu}$. Mutant version of *Drosophila melanogaster* Msl-1. Msl-1 is a component of the sex determination pathway that is usually expressed only in males, being repressed in females by a product of the Sex lethal gene. Activity of mutant is independent of Sex lethal, making it toxic to females if expressed at a high enough level. Toxicity is therefore sex-specific. The msl-1$^{MPU}$ cDNA was cloned as an EcoRI fragment from M1-ECTOPIC (Chang and Kuroda, (1998) Genetics 150(2): 699-709) into the WTP-2 vector digested with EcoRI. A diagnostic digest using HindIII/NotI, was then used to select a clone of the correct orientation, placing the msl-1$^{MPU}$ cDNA under the control of the tRe sequences.

tRe-Msl-2$^{Nopu}$. Mutant version of *Drosophila melanogaster* Msl-2. Msl-2 is another component of the sex determination pathway that is usually expressed only in males, being repressed in females by a product of the Sex lethal gene. Activity of mutant is independent of Sex lethal, making it toxic to females if expressed at a high enough level. Toxicity is therefore sex-specific. The msl-2 cDNA was cloned as a NotI/XbaI fragment from pM2 NOPU (Kelley et al., (1995), Cell 81; 867-877) and cloned into WTP-2 digested with NotI/XbaI.

Example 1

Single Chromosome Crosses

In "single chromosome crosses" at 25° C., ten to fifteen virgin females homozygous for the tTA construct and five to ten young males homozygous for the tRe construct were placed on food containing or lacking a tetracycline supplement. Their progeny were allowed to develop on this food. SXL$^{PE}$

| Tetracycline conc. μg/ml | Female | Total | Male | Total |
|---|---|---|---|---|
| 0 | 0$^A$, 0$^B$, 0$^C$, 0$^F$, 0, 0, 0, 0 | 0 | 58, 47, 60, 51, 46, 60, 52, 54 | 428 |
| 0.1 | 46, 49, 50, 51, 52, 50, 41, 40 | 379 | 56, 42, 72, 41, 56, 72, 61, 34 | 434 |
| 1 | 52, 40, 60, 0, 60, 72, 50, 52 | 386 | 50, 51, 55, 3, 63, 54, 57, 56 | 389 |
| 5 | 41, 55, 49, 52, 48, 47, 40, 51 | 383 | 36, 47, 42, 55, 36, 55, 52, 52 | 375 |

Sxlpe tTa$^{(A, B, C, F)}$ x tRe Ras64B$^{V12(B, C)}$

Format for data: the 8 numbers are the results from crosses using independent insertions of each element (to control for position effect). Here, 4 insertions of Sxl$^{pe}$-tTA (A, B, C, and F) were used and two of tRE-Ras64B$^{V12}$ (B and C). The order of the data are: Sxl$^{pe}$-tTA$^{(A)}$ females with tRe-Ras64B$^{V12\ (B)}$ males, then SxlBxRasB, SxlCxRasB, SxlFxRasB, SxlAxRasC, SxlBxRasC, SxlCxRasC and finally SxlFxRasC. Data are presented in a similar fashion in the other tables

| Tetracycline conc. μg/ml | Female | Total | Male | Total |
|---|---|---|---|---|
| 0 | 0, 0, 0, 0, 0, 0, 0, 0 | 0 | 59, 57, 62, 51, 73, 69, 57, 55 | 483 |
| 0.1 | 61, 52, 47, 46, 22, 31, 36, 15 | 296 | 60, 62, 56, 71, 69, 75, 55, 72 | 520 |
| 1 | 59, 57, 63, 59, 31, 21, 15, 21 | 326 | 47, 56, 49, 62, 63, 67, 71, 58 | 473 |
| 5 | 61, 47, 52, 56, 38, 22, 16, 12 | 304 | 68, 72, 67, 92, 58, 54, 61, 63 | 535 |

Sxlpe tTa$^{(A, B, C, F)}$ x tRe Msl-1$^{Mpu(A, B)}$

| Tetracycline conc. μg/ml | Female | Total | Male | Total |
|---|---|---|---|---|
| 0 | 0, 0, 0, 0, 0, 0, 0, 0, 0, 0, 0, 0 | 0 | 56, 72, 81, 69, 62, 63, 56, 47, 82, 57, 55, 61 | 761 |
| 0.1 | 79, 56, 47, 42, 51, 61, 52, 52, 49, 51, 53, 54 | 647 | 58, 41, 40, 35, 50, 67, 71, 39, 52, 62, 40, 70 | 562 |
| 1 | 42, 45, 56, 48, 52, 61, 57, 54, 55, 56, 57, 61 | 644 | 60, 39, 61, 60, 69, 49, 59, 38, 64, 69, 71, 35 | 674 |
| 5 | 58, 61, 52, 53, 54, 61, 29, 31, 55, 50, 49, 62 | 615 | 61, 59, 57, 56, 55, 48, 91, 63, 54, 50, 81, 67 | 742 |

Sxlpe tTa$^{(A, B, C, F)}$ x tRe Msl-2$^{Nopu(B, C, D)}$

Stwl

| Tetracycline conc. μg/ml | Female | Total | Male | Total |
|---|---|---|---|---|
| 0 | 0, 0, 0, 0, 0, 0 | 0 | 0, 0, 0, 0, 0, 0 | 0 |
| 0.1 | 36, 62, 71, 41, 49, 58 | 317 | 43, 442, 63, 35, 68 | 315 |
| 1 | 58, 37, 58,41, 55, 58 | 307 | 47, 70, 51, 51, 39, 70 | 328 |
| 5 | 36, 38, 56, 43, 34, 64 | 271 | 57, 71, 68, 53, 44, 42 | 335 |

Stwl tTa$^{(A, B, C)}$ x tRe Ras64B$^{V12(B, C)}$

| Tetracycline conc. μg/ml | Female | Total | Male | Total |
|---|---|---|---|---|
| 0 | 0, 0, 0, 0, 0, 0 | 0 | 50, 44, 45, 56, 40, 67 | 302 |
| 0.1 | 67, 56, 37, 23, 16, 12 | 211 | 56, 53, 50, 61, 42, 74 | 336 |
| 1 | 69, 64, 41, 13, 31, 18 | 236 | 33, 70, 39, 45, 40, 70 | 257 |
| 5 | 52, 42, 49, 19, 20, 41 | 223 | 37, 80, 41, 48, 80 | 291 |

Stwl tTa$^{(A, B, C)}$ x tRe Msl-1$^{Mpu(A, B)}$

| Tetracycline conc. μg/ml | Female | Total | Male | Total |
|---|---|---|---|---|
| 0 | 0, 0, 0, 0, 0, 0, 0, 0, 0 | 0 | 38, 53, 47, 68, 38, 70, 52, 60, 55 | 481 |
| 0.1 | 54, 57, 41, 64, 40, 63, 39, 42, 36 | 436 | 59, 58, 49, 73, 48, 69, 45, 47, 43 | 491 |
| 1 | 46, 34, 35, 63, 47, 70, 64, 39, 41 | 439 | 55, 40, 40, 71, 50, 72, 74, 46, 42 | 490 |
| 5 | 52, 70, 37, 34, 35, 57, 49, 50, 50 | 434 | 54, 71, 41, 42, 41, 66, 56, 55, 55 | 481 |

Stwl tTa$^{(A, B, C)}$ x tRe Msl-2$^{Nopu(B, C, D)}$

Actin5C

| Tetracycline conc. µg/ml | Female | Total | Male | Total |
|---|---|---|---|---|
| 0 | 0, 0, 0, 0, 0, 0 | 0 | 0, 0, 0, 0, 0, 0 | 377 |
| 0.1 | 77, 57, 69, 50, 45, 63 | 361 | 50, 70, 71, 67, 53, 61 | 372 |
| 1 | 86, 59, 60, 80, 70, 72 | 427 | 46, 89, 72, 45, 76, 55 | 383 |
| 5 | 46, 49, 87, 63, 59, 71 | 375 | 75, 83, 58, 83, 72, 82 | 400 |

Actin5C tTa$^{(B, C, E)}$ × tRe Ras64B$^{V12(B, C)}$

| Tetracycline conc. µg/ml | Female | Total | Male | Total |
|---|---|---|---|---|
| 0 | 0, 0, 0, 0, 0, 0 | 0 | 83, 73, 65, 69, 53, 80 | 423 |
| 0.1 | 72, 74, 80, 68, 72, 46 | 412 | 82, 52, 57, 66, 86, 59 | 402 |
| 1 | 61, 83, 48, 66, 65, 57 | 321 | 74, 69, 85, 58, 48, 61 | 351 |
| 5 | 70, 57, 50, 62, 61, p86 | 386 | 48, 68, 52, 62, 84, 87 | 401 |

Actin5C tTa$^{(B, C, E)}$ × tRe Msl-1$^{MPu(A, B)}$

| Tetracycline conc. µg/ml | Female | Total | Male | Total |
|---|---|---|---|---|
| 0 | 0, 0, 0, 0, 0, 0, 0, 0 | 0 | 63, 52, 67, 71, 88, 55, 46, 86, 75 | 603 |
| 0.1 | 84, 85, 83, 73, 48, 48, 46, 71, 58 | 548 | 62, 54, 48, 81, 85, 74, 78, 77, 78 | 637 |
| 1 | 70, 70, 66, 81, 50, 52, 69, 81, 51 | 590 | 69, 87, 47, 64, 66, 59, 58, 47, 52 | 549 |
| 5 | 67, 70, 87, 61, 54, 54, 67, 74, 81 | 615 | 71, 61, 57, 53, 51, 65, 45, 68, 51 | 522 |

Actin5C tTa$^{(B, C, E)}$ × tRe Msl-2$^{Nopu (B, C, D)}$

Hsp26

| Tetracycline conc. µg/ml | Female | Total | Male | Total |
|---|---|---|---|---|
| 0 | 0, 0, 0 | 0 | 0, 0, 0, 0 | 0 |
| 0.1 | 47, 56, 71, 61 | 235 | 46, 52, 53, 59 | 210 |
| 1 | 60, 46, 52, 41 | 199 | 79, 71, 68, 56 | 274 |
| 5 | 2, 51, 71, 32 | 156 | 0, 49, 62, 43 | 154 |

Hsp26 tTa$^{(A)}$ × tRe Ras64B$^{V12(B, C)}$

| Tetracycline conc. µg/ml | Female | Total | Male | Total |
|---|---|---|---|---|
| 0 | 0, 0, 0, 0, 0, 0 | 0 | 64, 58, 33, 66, 55, 42 | 318 |
| 0.1 | 45, 44, 72, 56, 62, 49 | 328 | 53, 54, 80, 57, 66, 58 | 368 |
| 1 | 70, 35, 61, 50, 57, 37 | 310 | 78, 36, 70, 56, 61, 42 | 343 |
| 5 | 44, 58, 58, 59, 42, 52 | 313 | 46, 68, 66, 64, 48, 55 | 347 |

Hsp26 tTa$^{(A)}$ × tRe MSl-1$^{Mpu(A, B)}$

| Tetracycline conc. µg/ml | Female | Total | Male | Total |
|---|---|---|---|---|
| 0 | 0, 0, 0 | 0 | 56, 47, 56 | 159 |
| 0.1 | 48, 49, 62 | 159 | 56, 68, 49 | 159 |
| 1 | 43, 45, 51 | 135 | 36, 39, 47 | 122 |
| 5 | 55, 3, 66 | 124 | 61, 5, 54 | 120 |

Hsp26 tTa$^{(A)}$ × tRe Msl-2$^{Nopu(A, B)}$

Yp3

| Tetracycline conc. µg/ml | Female | Total | Male | Total |
|---|---|---|---|---|
| 0 | 0, 0, 0, 0, 0, 0 | 0 | 65, 70, 61, 65, 47, 42 | 350 |
| 0.1 | 33, 54, 50, 72, 63, 50 | 322 | 42, 64, 52, 74, 67, 54 | 352 |
| 1 | 56, 56, 61, 69, 57, 43 | 342 | 59, 64, 65, 75, 64, 49 | 376 |
| 5 | 46, 51, 73, 65, 42, 39 | 316 | 44, 56, 79, 74, 52, 49 | 354 |

Yp3 tTa$^{(A)}$ × tRe Ras64B$^{V12(B, C)}$

| Tetracycline conc. µg/ml | Female | Total | Male | Total |
|---|---|---|---|---|
| 0 | 0, 0, 2, 0, 0, 0 | 2 | 49, 58, 39, 65, 35, 51 | 297 |
| 0.1 | 36, 65, 71, 37, 59, 68 | 336 | 46, 73, 77, 46, 66, 71 | 379 |
| 1 | 42, 65, 67, 57, 35, 53 | 319 | 49, 72, 68, 59, 41, 58 | 347 |
| 5 | 55, 55, 43, 58, 36, 60 | 307 | 63, 64, 49, 63, 45, 64 | 348 |

Yp3 tTa$^{(A)}$ × tRe Msl-1$^{Mpu(A, B)}$

| Tetracycline conc. µg/ml | Female | Total | Male | Total |
|---|---|---|---|---|
| 0 | 0, 0, 0, 0, 0, 0 | 0 | 35, 35, 72, 52, 45, 37 | 276 |
| 0.1 | 34, 68, 42, 51, 33, 40 | 268 | 35, 72, 45, 56, 36, 44 | 248 |
| 1 | 41, 39, 42, 60, 70, 72 | 324 | 51, 49, 46, 61, 78, 77 | 362 |
| 5 | 70, 55, 56, 65, 43, 61 | 349 | 74, 58, 64, 73, 51, 66 | 386 |

Yp3 tTa$^{(A)}$ × tRe Msl-2$^{Nopu(A, B)}$

Conclusion

These data show that one or both sexes can be efficiently eliminated, while good repression of this lethality can be achieved by the addition of modest concentrations of tetracycline to the food. This repression is effective over a wide range of tetracycline concentrations.

Example 2

Reporter Crosses

In "reporter crosses" at 25° C., females homozygous carrying an insertion of Sxlp$^e$ tTa on their X chromosome (Sxlp$^e$ tTa$^{(A)}$) were crossed to males carrying various reporter constructs. As with "single chromosome crosses", ten to fifteen virgin females homozygous for the tTA construct and five to ten young males homozygous for the tRe construct were placed on food containing or lacking a tetracycline supplement. Their progeny were allowed to develop on this food.

lacZ

Embryos were stained for lacZ using a standard histochemical method.

| Tetracycline conc. µg/ml | LacZ positive | Total | LacZ negative | Total |
|---|---|---|---|---|
| 0 | 60, 85, 99, 60 | 304 | 78, 89, 85, 93 | 345 |
| 0.1 | 0, 0, 0, 0 | 0 | 176, 174, 178, 181 | 709 |
| 1 | 0, 0, 0, 0 | 0 | 188, 190, 181, 180 | 739 |
| 5 | 0, 0, 0, 0 | 0 | 156, 151, 159, 185 | 651 |

(Female) $Sxlp^e\ tTa^{(A)}$ × tRe $lacZ^{(III)}$ (Male)

| Tetracycline conc. µg/ml | LacZ positive | Total | LacZ negative | Total |
|---|---|---|---|---|
| 0 | 57, 82, 97, 45 | 281 | 61, 74, 59, 82 | 276 |
| 0.1 | 0, 0, 0, 0 | 0 | 131, 165, 132, 90 | 518 |
| 1 | 0, 0, 0, 0 | 0 | 170, 161, 181, 195 | 707 |
| 5 | 0, 0, 0, 0 | 0 | 126, 190, 190, 196 | 702 |

(Male) $Sxlp^e\ tTa^{(A)}$ × tRe $lacZ^{(III)}$ (Female)

| Tetracycline conc. µg/ml | LacZ positive | Total | LacZ negative | Total |
|---|---|---|---|---|
| 0 | 0, 0, 0, 0 | 0 | 189, 200, 153, 169 | 711 |
| 0.1 | 0, 0, 0, 0 | 0 | 164, 175, 190, 179 | 708 |
| 1 | 0, 0, 0, 0 | 0 | 182, 190, 195, 167 | 737 |
| 5 | 0, 0, 0, 0 | 0 | 199, 151, 169, 164 | 683 |

(Male) $Sxlp^e\ tTa^{(A)}$ tRe $lacZ^{(I)}$ × C(1)DX (Female)

EGFP

Embryos were scored for fluorescence. In the case of embryos on tetracycline-free media, these were separated, allowed to develop on tetracycline-free media and the sex of the emerging adults was scored.

| Tetracycline conc. µg/ml | Fluorescent | female | male | Non-Fluorescent | female | male |
|---|---|---|---|---|---|---|
| 0 | 89, 100, 53, 55 | 200 | 0 | 99, 86, 46, 51 | 0 | 232 |
| 0.1 | 0, 0, 0, 0 | — | — | 199, 182, 188, 153 | — | — |
| 1 | 0, 0, 0, 0 | — | — | 170, 135, 163, 196 | — | — |
| 5 | 0, 0, 0, 0 | — | — | 186, 159, 127, 200 | — | — |

(Female) $Sxlp^e\ tTa^{(A)}$ × tRe $EGFP^{(II)}$ (Male)

| Tetracycline conc. µg/ml | Fluorescent | female | male | Non-Fluorescent | female | male |
|---|---|---|---|---|---|---|
| 0 | 60, 91, 62, 83 | 243 | 0 | 102, 56, 79, 72 | 1 | 256 |
| 0.1 | 0, 0, 0, 0 | — | — | 196, 170, 165, 162 | — | — |
| 1 | 0, 0, 0, 0 | — | — | 182, 200, 197, 161 | — | — |
| 5 | 0, 0, 0, 0 | — | — | 182, 161, 188, 182 | — | — |

(Male) $Sxlp^e\ tTa^{(A)}$ × tRe $EGFP^{(II)}$ (Female)

| Tetracycline conc. µg/ml | Fluorescent | male | female | Non-Fluorescent | male | female |
|---|---|---|---|---|---|---|
| 0 | 0, 0, 0, 0 | — | — | 196, 179, 165, 164 | — | — |
| 0.1 | 0, 0, 0, 0 | — | — | 179, 197, 198, 188 | — | — |
| 1 | 0, 0, 0, 0 | — | — | 198, 187, 190, 164 | — | — |
| 5 | 0, 0, 0, 0 | — | — | 170, 177, 199, 165 | — | — |

(Male) $Sxlp^e\ tTa^{(A)}$; tRe $EGFP^{(II)}$ × C(1)DX (Female)

C(1)DX is a compound X chromosome; effectively two X chromosomes joined together. The X chromosome from males crossed to C(1)DX females is therefore inherited by the sons, rather than the daughters.

Conclusions

The data demonstrate that, as expected, reporter gene expression is turned off in the presence of tetracycline over a range of concentrations.

Example 3

Recombinant Chromosome Experiments 40-45 young females and 20-25 young males raised at 25° C. upon food with the indicated tetracycline supplement were allowed to mate, then transferred to normal (tetracycline-free) food after 3-4 days. These flies were transferred to fresh vials of normal food every day for 12 days, then removed on the 13th day. All the vials were incubated at 25° C. while the progeny developed. The numbers of male and female progeny emerging as adults in each vial were recorded.

Tetracycline Concentration
$Sxl^{pe}$

| Tet. Conc. µg/ml | Day 1 Male | Day 1 Female | Day 2 Male | Day 2 Female | Day 3 Male | Day 3 Female | Day 4 Male | Day 4 Female | Day 5 Male | Day 5 Female | Day 6 Male | Day 6 Female | Day 7 Male | Day 7 Female |
|---|---|---|---|---|---|---|---|---|---|---|---|---|---|---|
| 0.1 | 103 | 0 | 98 | 0 | 89 | 0 | 92 | 0 | 105 | 0 | 95 | 0 | 110 | 0 |
| 1 | 128 | 0 | 137 | 0 | 150 | 0 | 136 | 0 | 111 | 0 | 87 | 0 | 100 | 0 |
| 5 | 110 | 0 | 111 | 0 | 95 | 0 | 90 | 0 | 144 | 0 | 93 | 0 | 138 | 0 |
| 20 | 131 | 0 | 126 | 0 | 133 | 0 | 120 | 0 | 93 | 0 | 99 | 0 | 111 | 0 |
| 100 | 139 | 0 | 127 | 0 | 145 | 0 | 110 | 0 | 149 | 0 | 128 | 0 | 94 | 0 |
| 500 | 95 | 11 | 133 | 12 | 145 | 1 | 137 | 1 | 86 | 0 | 112 | 0 | 128 | 0 |

-continued

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| µg/ml | Male | Female | Male | Female | Male | Female | Male | Female | Male | Female | Male | Female | Male | Female |
| 1000 | 140 | 12 | 133 | 24 | 119 | 8 | 94 | 2 | 92 | 1 | 137 | 1 | 129 | 1 |
| 2000 | 110 | 35 | 97 | 25 | 94 | 16 | 138 | 12 | 115 | 2 | 126 | 1 | 145 | 1 |

| Tet. Conc. | Day 8 | | Day 9 | | Day 10 | | Day 11 | | Day 12 | | Total | |
|---|---|---|---|---|---|---|---|---|---|---|---|---|
| µg/ml | Male | Female | Male | Female | Male | Female | Male | Female | Male | Female | Male | Female |
| 0.1 | 106 | 0 | 131 | 0 | 148 | 0 | 86 | 0 | 99 | 0 | 1262 | 0 |
| 1 | 106 | 0 | 109 | 0 | 97 | 0 | 124 | 0 | 114 | 0 | 1399 | 0 |
| 5 | 106 | 0 | 89 | 0 | 148 | 0 | 148 | 0 | 87 | 0 | 1359 | 0 |
| 20 | 87 | 0 | 149 | 0 | 104 | 0 | 113 | 0 | 132 | 0 | 1398 | 0 |
| 100 | 93 | 0 | 125 | 0 | 99 | 0 | 121 | 0 | 139 | 0 | 1469 | 0 |
| 500 | 142 | 0 | 129 | 0 | 114 | 0 | 131 | 0 | 126 | 0 | 1478 | 25 |
| 1000 | 89 | 0 | 94 | 0 | 97 | 0 | 138 | 0 | 87 | 0 | 1349 | 49 |
| 2000 | 94 | 0 | 137 | 0 | 99 | 0 | 141 | 0 | 143 | 0 | 1439 | 92 |

$Sxl^{pe}$-tTA, tRE-Ras64B$^{V12}$ on the X chromosome.

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| µg/ml | Male | Female | Male | Female | Male | Female | Male | Female | Male | Female | Male | Female | Male | Female |
| 0.1 | 103 | 0 | 98 | 0 | 149 | 0 | 121 | 0 | 134 | 0 | 150 | 0 | 117 | 0 |
| 1 | 149 | 0 | 86 | 0 | 111 | 0 | 112 | 0 | 126 | 0 | 148 | 0 | 136 | 0 |
| 5 | 104 | 0 | 99 | 0 | 148 | 0 | 128 | 0 | 142 | 0 | 134 | 0 | 93 | 0 |
| 20 | 121 | 0 | 106 | 0 | 97 | 0 | 127 | 0 | 142 | 0 | 131 | 0 | 107 | 0 |
| 100 | 94 | 0 | 142 | 0 | 115 | 0 | 131 | 0 | 114 | 0 | 103 | 0 | 131 | 0 |
| 500 | 140 | 34 | 148 | 23 | 100 | 14 | 95 | 1 | 122 | 0 | 120 | 0 | 115 | 0 |
| 1000 | 110 | 29 | 87 | 12 | 138 | 22 | 145 | 17 | 91 | 5 | 106 | 1 | 102 | 1 |
| 2000 | 123 | 42 | 145 | 37 | 131 | 43 | 139 | 15 | 126 | 12 | 118 | 7 | 100 | 4 |

| Tet. Conc. | Day 8 | | Day 9 | | Day 10 | | Day 11 | | Day 12 | | Total | |
|---|---|---|---|---|---|---|---|---|---|---|---|---|
| µg/ml | Male | Female | Male | Female | Male | Female | Male | Female | Male | Female | Male | Female |
| 0.1 | 138 | 0 | 142 | 0 | 147 | 0 | 130 | 0 | 112 | 0 | 1541 | 0 |
| 1 | 129 | 0 | 123 | 0 | 91 | 0 | 99 | 0 | 131 | 0 | 1441 | 0 |
| 5 | 99 | 0 | 106 | 0 | 95 | 0 | 144 | 0 | 129 | 0 | 1421 | 0 |
| 20 | 149 | 0 | 150 | 0 | 89 | 0 | 128 | 0 | 140 | 0 | 1487 | 0 |
| 100 | 93 | 0 | 119 | 0 | 143 | 0 | 87 | 0 | 144 | 0 | 1416 | 0 |
| 500 | 98 | 0 | 129 | 0 | 90 | 0 | 124 | 0 | 107 | 0 | 1388 | 72 |
| 1000 | 92 | 0 | 150 | 0 | 145 | 0 | 107 | 0 | 143 | 0 | 1416 | 87 |
| 2000 | 92 | 1 | 120 | 0 | 89 | 0 | 106 | 0 | 149 | 0 | 1438 | 161 |

$Sxl^{pe}$-tTA, tRE-Ras64B$^{V12}$ on the third chromosome.

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| µg/ml | Male | Female | Male | Female | Male | Female | Male | Female | Male | Female | Male | Female | Male | Female |
| 0.1 | 97 | 0 | 136 | 0 | 152 | 0 | 130 | 0 | 108 | 0 | 114 | 0 | 88 | 0 |
| 1 | 102 | 0 | 99 | 0 | 134 | 0 | 171 | 0 | 171 | 0 | 118 | 0 | 91 | 0 |
| 5 | 130 | 0 | 159 | 0 | 156 | 0 | 91 | 0 | 84 | 0 | 127 | 0 | 110 | 0 |
| 20 | 76 | 0 | 129 | 0 | 126 | 0 | 79 | 0 | 89 | 0 | 98 | 0 | 94 | 0 |
| 100 | 112 | 0 | 145 | 0 | 130 | 0 | 124 | 0 | 79 | 0 | 109 | 0 | 134 | 0 |
| 500 | 136 | 2 | 79 | 0 | 161 | 0 | 102 | 0 | 171 | 0 | 151 | 0 | 161 | 0 |
| 1000 | 92 | 15 | 83 | 9 | 150 | 3 | 149 | 2 | 146 | 0 | 92 | 0 | 115 | 0 |
| 2000 | 127 | 21 | 95 | 14 | 153 | 3 | 164 | 4 | 135 | 1 | 97 | 1 | 144 | 0 |

| Tet. Conc. | Day 8 | | Day 9 | | Day 10 | | Day 11 | | Day 12 | | Total | |
|---|---|---|---|---|---|---|---|---|---|---|---|---|
| µg/ml | Male | Female | Male | Female | Male | Female | Male | Female | Male | Female | Male | Female |
| 0.1 | 140 | 0 | 104 | 0 | 141 | 0 | 173 | 0 | 81 | 0 | 1464 | 0 |
| 1 | 104 | 0 | 120 | 0 | 171 | 0 | 102 | 0 | 144 | 0 | 1527 | 0 |
| 5 | 116 | 0 | 123 | 0 | 155 | 0 | 163 | 0 | 121 | 0 | 1535 | 0 |
| 20 | 122 | 0 | 103 | 0 | 126 | 0 | 123 | 0 | 78 | 0 | 1243 | 0 |
| 100 | 127 | 0 | 133 | 0 | 79 | 0 | 157 | 0 | 154 | 0 | 1483 | 0 |
| 500 | 164 | 0 | 95 | 0 | 160 | 0 | 154 | 0 | 91 | 0 | 1625 | 2 |
| 1000 | 168 | 0 | 153 | 0 | 80 | 0 | 95 | 0 | 79 | 0 | 1402 | 29 |
| 2000 | 158 | 0 | 103 | 0 | 129 | 0 | 141 | 0 | 97 | 0 | 1543 | 44 |

$Sxl^{pe}$-tTA, tRE-Msl-2$^{Nopu}$ on the X chromosome.

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| µg/ml | Male | Female | Male | Female | Male | Female | Male | Female | Male | Female | Male | Female | Male | Female |
| 0.1 | 111 | 0 | 108 | 0 | 130 | 0 | 69 | 0 | 101 | 0 | 110 | 0 | 130 | 0 |
| 1 | 89 | 0 | 106 | 0 | 119 | 0 | 70 | 0 | 87 | 0 | 117 | 0 | 138 | 0 |
| 5 | 112 | 0 | 80 | 0 | 68 | 0 | 130 | 0 | 78 | 0 | 93 | 0 | 78 | 0 |
| 20 | 92 | 0 | 83 | 0 | 129 | 0 | 127 | 0 | 66 | 0 | 69 | 0 | 95 | 0 |
| 100 | 72 | 0 | 90 | 0 | 72 | 0 | 66 | 0 | 106 | 0 | 122 | 0 | 100 | 0 |
| 500 | 78 | 0 | 118 | 0 | 69 | 0 | 67 | 0 | 88 | 0 | 83 | 0 | 135 | 0 |
| 1000 | 122 | 2 | 107 | 1 | 133 | 0 | 116 | 0 | 115 | 0 | 107 | 0 | 119 | 0 |
| 2000 | 134 | 12 | 79 | 14 | 123 | 5 | 130 | 1 | 102 | 0 | 114 | 0 | 83 | 0 |

| Tet. Conc. | Day 8 | | Day 9 | | Day 10 | | Day 11 | | Day 12 | | Total | |
|---|---|---|---|---|---|---|---|---|---|---|---|---|
| µg/ml | Male | Female | Male | Female | Male | Female | Male | Female | Male | Female | Male | Female |
| 0.1 | 127 | 0 | 92 | 0 | 79 | 0 | 77 | 0 | 133 | 0 | 1267 | 0 |
| 1 | 71 | 0 | 104 | 0 | 81 | 0 | 124 | 0 | 65 | 0 | 1171 | 0 |
| 5 | 106 | 0 | 84 | 0 | 135 | 0 | 119 | 0 | 82 | 0 | 1165 | 0 |
| 20 | 101 | 0 | 71 | 0 | 108 | 0 | 74 | 0 | 112 | 0 | 1127 | 0 |
| 100 | 136 | 0 | 104 | 0 | 116 | 0 | 77 | 0 | 107 | 0 | 1168 | 0 |
| 500 | 128 | 0 | 104 | 0 | 73 | 0 | 106 | 0 | 88 | 0 | 1137 | 0 |
| 1000 | 101 | 0 | 115 | 0 | 86 | 0 | 96 | 0 | 92 | 0 | 1309 | 3 |
| 2000 | 130 | 0 | 105 | 0 | 120 | 0 | 104 | 0 | 101 | 0 | 1325 | 32 |

$Sxl^{pe}$-tTA, tRE-Msl-$2^{Nopu}$ on the third chromosome.

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| µg/ml | Male | Female | Male | Female | Male | Female | Male | Female | Male | Female | Male | Female | Male | Female |
| 0.1 | 93 | 0 | 137 | 0 | 84 | 0 | 66 | 0 | 114 | 0 | 107 | 0 | 114 | 0 |
| 1 | 73 | 0 | 90 | 0 | 99 | 0 | 120 | 0 | 118 | 0 | 85 | 0 | 85 | 0 |
| 5 | 84 | 0 | 122 | 0 | 131 | 0 | 93 | 0 | 104 | 0 | 90 | 0 | 133 | 0 |
| 20 | 127 | 0 | 128 | 0 | 80 | 0 | 105 | 0 | 81 | 0 | 122 | 0 | 108 | 0 |
| 100 | 72 | 0 | 80 | 0 | 87 | 0 | 128 | 0 | 78 | 0 | 92 | 0 | 86 | 0 |
| 500 | 98 | 0 | 78 | 0 | 94 | 1 | 105 | 0 | 138 | 0 | 77 | 0 | 92 | 0 |
| 1000 | 117 | 1 | 105 | 2 | 130 | 1 | 130 | 1 | 82 | 0 | 88 | 0 | 113 | 0 |
| 2000 | 91 | 16 | 70 | 11 | 69 | 13 | 70 | 4 | 108 | 1 | 90 | 0 | 115 | 0 |

| Tet. Conc. | Day 8 | | Day 9 | | Day 10 | | Day 11 | | Day 12 | | Total | |
|---|---|---|---|---|---|---|---|---|---|---|---|---|
| µg/ml | Male | Female | Male | Female | Male | Female | Male | Female | Male | Female | Male | Female |
| 0.1 | 117 | 0 | 78 | 0 | 123 | 0 | 125 | 0 | 121 | 0 | 1279 | 0 |
| 1 | 91 | 0 | 90 | 0 | 68 | 0 | 88 | 0 | 82 | 0 | 1089 | 0 |
| 5 | 89 | 0 | 70 | 0 | 138 | 0 | 85 | 0 | 100 | 0 | 1239 | 0 |
| 20 | 95 | 0 | 118 | 0 | 70 | 0 | 114 | 0 | 114 | 0 | 1262 | 0 |
| 100 | 66 | 0 | 137 | 0 | 85 | 0 | 109 | 0 | 93 | 0 | 1113 | 0 |
| 500 | 68 | 0 | 70 | 0 | 109 | 0 | 86 | 0 | 136 | 0 | 1151 | 1 |
| 1000 | 95 | 0 | 137 | 0 | 99 | 0 | 120 | 0 | 66 | 0 | 1282 | 5 |
| 2000 | 84 | 0 | 98 | 0 | 83 | 0 | 128 | 0 | 131 | 0 | 1137 | 45 |

$Sxl^{pe}$-tTA, tRE-Msl-$1^{Mpu}$ on the X chromosome.

Hsp26

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| µg/ml | Male | Female | Male | Female | Male | Female | Male | Female | Male | Female | Male | Female | Male | Female |
| 0.1 | 153 | 0 | 154 | 0 | 127 | 0 | 130 | 0 | 81 | 0 | 151 | 0 | 147 | 0 |
| 1 | 138 | 0 | 98 | 0 | 74 | 0 | 88 | 0 | 150 | 0 | 123 | 0 | 115 | 0 |
| 5 | 140 | 0 | 132 | 0 | 119 | 0 | 129 | 0 | 87 | 0 | 156 | 0 | 157 | 0 |
| 20 | 115 | 0 | 113 | 0 | 92 | 0 | 92 | 0 | 129 | 0 | 77 | 0 | 119 | 0 |
| 100 | 150 | 0 | 127 | 0 | 126 | 0 | 114 | 0 | 78 | 0 | 93 | 0 | 98 | 0 |
| 500 | 119 | 1 | 146 | 0 | 154 | 0 | 132 | 0 | 112 | 0 | 97 | 0 | 80 | 0 |

| Tet. Conc. | | | | | | | | | | | | |
|---|---|---|---|---|---|---|---|---|---|---|---|---|
| µg/ml | | | | | | | | | | | | |
| 1000 | 77 | 5 | 109 | 2 | 105 | 2 | 85 | 0 | 84 | 0 | 127 | 0 | 91 | 0 |
| 2000 | 156 | 18 | 101 | 6 | 149 | 3 | 115 | 1 | 134 | 0 | 139 | 0 | 151 | 0 |

| Tet. Conc. | Day 8 | | Day 9 | | Day 10 | | Day 11 | | Day 12 | | Total | |
|---|---|---|---|---|---|---|---|---|---|---|---|---|
| µg/ml | Male | Female | Male | Female | Male | Female | Male | Female | Male | Female | Male | Female |
| 0.1 | 117 | 0 | 81 | 0 | 106 | 0 | 135 | 0 | 141 | 0 | 1523 | 0 |
| 1 | 152 | 0 | 89 | 0 | 105 | 0 | 146 | 0 | 89 | 0 | 1367 | 0 |
| 5 | 79 | 0 | 148 | 0 | 120 | 0 | 92 | 0 | 119 | 0 | 1478 | 0 |
| 20 | 69 | 0 | 78 | 0 | 149 | 0 | 72 | 0 | 116 | 0 | 1221 | 0 |
| 100 | 121 | 0 | 126 | 0 | 157 | 0 | 141 | 0 | 143 | 0 | 1474 | 0 |
| 500 | 142 | 0 | 103 | 0 | 104 | 0 | 144 | 0 | 129 | 0 | 1462 | 1 |
| 1000 | 75 | 0 | 147 | 0 | 105 | 0 | 97 | 0 | 123 | 0 | 1225 | 9 |
| 2000 | 86 | 0 | 97 | 0 | 98 | 0 | 131 | 0 | 76 | 0 | 1433 | 28 |

Hsp26-tTA, tRE-Msl-2$^{Nopu}$ on the second chromosome.

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| µg/ml | Male | Female | Male | Female | Male | Female | Male | Female | Male | Female | Male | Female | Male | Female |
| 0.1 | 120 | 0 | 87 | 0 | 127 | 0 | 115 | 0 | 121 | 0 | 80 | 0 | 100 | 0 |
| 1 | 84 | 0 | 153 | 0 | 100 | 0 | 88 | 0 | 93 | 0 | 71 | 0 | 126 | 0 |
| 5 | 134 | 0 | 95 | 0 | 122 | 0 | 141 | 0 | 80 | 0 | 77 | 0 | 106 | 0 |
| 20 | 135 | 0 | 137 | 0 | 140 | 0 | 135 | 0 | 107 | 0 | 141 | 0 | 89 | 0 |
| 100 | 146 | 1 | 146 | 0 | 82 | 0 | 106 | 0 | 118 | 0 | 118 | 0 | 82 | 0 |
| 500 | 124 | 12 | 144 | 8 | 99 | 2 | 154 | 1 | 137 | 0 | 96 | 1 | 75 | 0 |
| 1000 | 72 | 27 | 85 | 17 | 76 | 15 | 87 | 12 | 102 | 5 | 93 | 5 | 69 | 3 |
| 2000 | 132 | 67 | 96 | 45 | 119 | 38 | 135 | 35 | 104 | 22 | 90 | 17 | 149 | 12 |

| Tet. Conc. | Day 8 | | Day 9 | | Day 10 | | Day 11 | | Day 12 | | Total | |
|---|---|---|---|---|---|---|---|---|---|---|---|---|
| µg/ml | Male | Female | Male | Female | Male | Female | Male | Female | Male | Female | Male | Female |
| 0.1 | 151 | 0 | 79 | 0 | 108 | 0 | 69 | 0 | 107 | 0 | 1264 | 0 |
| 1 | 78 | 0 | 95 | 0 | 105 | 0 | 112 | 0 | 154 | 0 | 1259 | 0 |
| 5 | 135 | 0 | 84 | 0 | 152 | 0 | 145 | 0 | 142 | 0 | 1413 | 0 |
| 20 | 79 | 0 | 157 | 0 | 92 | 0 | 73 | 0 | 139 | 0 | 1424 | 0 |
| 100 | 96 | 0 | 135 | 0 | 86 | 0 | 106 | 0 | 157 | 0 | 1378 | 1 |
| 500 | 139 | 0 | 142 | 0 | 145 | 0 | 84 | 0 | 136 | 0 | 1475 | 24 |
| 1000 | 114 | 1 | 145 | 0 | 130 | 0 | 136 | 0 | 152 | 0 | 1261 | 85 |
| 2000 | 149 | 2 | 81 | 0 | 127 | 0 | 146 | 0 | 88 | 0 | 1416 | 238 |

Hsp26-tTA, tRE-Msl-1$^{Mpu}$ on the second chromosome.

Yp3

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| µg/ml | Male | Female | Male | Female | Male | Female | Male | Female | Male | Female | Male | Female | Male | Female |
| 0.1 | 93 | 0 | 119 | 0 | 112 | 0 | 141 | 0 | 100 | 0 | 126 | 0 | 89 | 0 |
| 1 | 117 | 0 | 135 | 0 | 122 | 0 | 121 | 0 | 127 | 0 | 101 | 0 | 136 | 0 |
| 5 | 112 | 0 | 116 | 0 | 128 | 0 | 111 | 0 | 136 | 0 | 113 | 0 | 130 | 0 |
| 20 | 89 | 0 | 107 | 0 | 107 | 0 | 98 | 0 | 88 | 0 | 102 | 0 | 107 | 0 |
| 100 | 129 | 0 | 136 | 0 | 128 | 0 | 127 | 0 | 135 | 0 | 144 | 0 | 107 | 0 |
| 500 | 136 | 2 | 88 | 0 | 113 | 0 | 113 | 0 | 87 | 0 | 94 | 0 | 109 | 0 |
| 1000 | 107 | 13 | 140 | 5 | 110 | 0 | 141 | 0 | 98 | 0 | 129 | 0 | 88 | 0 |
| 2000 | 119 | 32 | 102 | 15 | 107 | 12 | 109 | 9 | 109 | 8 | 140 | 2 | 127 | 0 |

| Tet. Conc. | Day 8 | | Day 9 | | Day 10 | | Day 11 | | Day 12 | | Total | |
|---|---|---|---|---|---|---|---|---|---|---|---|---|
| µg/ml | Male | Female | Male | Female | Male | Female | Male | Female | Male | Female | Male | Female |
| 0.1 | 105 | 0 | 133 | 0 | 93 | 0 | 131 | 0 | 121 | 0 | 1363 | 0 |
| 1 | 90 | 0 | 119 | 0 | 94 | 0 | 98 | 0 | 100 | 0 | 1360 | 0 |
| 5 | 119 | 0 | 96 | 0 | 88 | 0 | 144 | 0 | 91 | 0 | 1384 | 0 |
| 20 | 135 | 0 | 126 | 0 | 143 | 0 | 123 | 0 | 141 | 0 | 1366 | 0 |
| 100 | 96 | 0 | 92 | 0 | 104 | 0 | 94 | 0 | 115 | 0 | 1407 | 0 |
| 500 | 141 | 0 | 144 | 0 | 123 | 0 | 104 | 0 | 124 | 0 | 1376 | 2 |
| 1000 | 138 | 0 | 105 | 0 | 124 | 0 | 115 | 0 | 114 | 0 | 1409 | 18 |
| 2000 | 114 | 0 | 123 | 0 | 132 | 0 | 115 | 0 | 107 | 0 | 1404 | 78 |

Yp3-tTA, tRE-Ras64B$^{V12}$ on the second chromosome.

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| μg/ml | Male | Female | Male | Female | Male | Female | Male | Female | Male | Female | Male | Female | Male | Female |
| 0.1 | 121 | 0 | 94 | 0 | 103 | 0 | 93 | 0 | 96 | 0 | 119 | 0 | 119 | 0 |
| 1 | 95 | 0 | 123 | 0 | 79 | 0 | 78 | 0 | 130 | 0 | 103 | 0 | 112 | 0 |
| 5 | 109 | 0 | 110 | 0 | 118 | 0 | 124 | 0 | 86 | 0 | 122 | 0 | 90 | 0 |
| 20 | 81 | 0 | 89 | 0 | 127 | 0 | 82 | 0 | 81 | 0 | 79 | 0 | 128 | 0 |
| 100 | 112 | 0 | 87 | 1 | 87 | 1 | 113 | 0 | 95 | 1 | 91 | 1 | 84 | 1 |
| 500 | 84 | 21 | 96 | 16 | 86 | 15 | 124 | 9 | 123 | 5 | 86 | 3 | 106 | 1 |
| 1000 | 100 | 47 | 110 | 12 | 109 | 8 | 103 | 13 | 102 | 9 | 97 | 2 | 82 | 6 |
| 2000 | 127 | 63 | 130 | 54 | 128 | 34 | 117 | 21 | 89 | 12 | 87 | 11 | 90 | 4 |

| Tet. Conc. | Day 8 | | Day 9 | | Day 10 | | Day 11 | | Day 12 | | Total | |
|---|---|---|---|---|---|---|---|---|---|---|---|---|
| μg/ml | Male | Female | Male | Female | Male | Female | Male | Female | Male | Female | Male | Female |
| 0.1 | 84 | 0 | 127 | 0 | 104 | 0 | 76 | 0 | 95 | 0 | 1231 | 0 |
| 1 | 94 | 0 | 106 | 0 | 83 | 0 | 93 | 0 | 113 | 0 | 1209 | 0 |
| 5 | 132 | 0 | 126 | 0 | 76 | 0 | 128 | 0 | 102 | 0 | 1323 | 0 |
| 20 | 119 | 0 | 99 | 0 | 90 | 0 | 106 | 0 | 87 | 0 | 1168 | 0 |
| 100 | 85 | 1 | 122 | 0 | 114 | 0 | 90 | 0 | 126 | 0 | 1206 | 6 |
| 500 | 85 | 1 | 93 | 0 | 111 | 0 | 111 | 0 | 104 | 0 | 1209 | 71 |
| 1000 | 95 | 0 | 113 | 0 | 110 | 0 | 85 | 0 | 87 | 0 | 1193 | 97 |
| 2000 | 131 | 1 | 128 | 0 | 91 | 0 | 95 | 0 | 82 | 0 | 1295 | 200 |

Yp3-tTA, tRE-Msl-2$^{Nopu}$ on the second chromosome.

| Tet. Conc. | Day 1 | | Day 2 | | Day 3 | | Day 4 | | Day 5 | | Day 6 | | Day 7 | |
|---|---|---|---|---|---|---|---|---|---|---|---|---|---|---|
| μg/ml | Male | Female | Male | Female | Male | Female | Male | Female | Male | Female | Male | Female | Male | Female |
| 0.1 | 91 | 0 | 84 | 0 | 107 | 0 | 80 | 0 | 88 | 0 | 92 | 0 | 99 | 0 |
| 1 | 117 | 0 | 92 | 0 | 128 | 0 | 80 | 0 | 104 | 0 | 116 | 2 | 8 | 0 |
| 5 | 82 | 0 | 123 | 0 | 116 | 0 | 120 | 2 | 89 | 0 | 90 | 0 | 95 | 0 |
| 20 | 92 | 1 | 101 | 0 | 87 | 0 | 109 | 0 | 81 | 0 | 121 | 0 | 83 | 1 |
| 100 | 108 | 13 | 130 | 9 | 131 | 5 | 99 | 7 | 109 | 3 | 123 | 1 | 107 | 1 |
| 500 | 78 | 22 | 85 | 16 | 80 | 12 | 106 | 15 | 130 | 11 | 91 | 10 | 118 | 7 |
| 1000 | 130 | 35 | 86 | 42 | 78 | 26 | 116 | 14 | 80 | 12 | 82 | 17 | 77 | 15 |
| 2000 | 116 | 79 | 130 | 72 | 78 | 44 | 101 | 29 | 132 | 32 | 94 | 22 | 89 | 16 |

| Tet. Conc. | Day 8 | | Day 9 | | Day 10 | | Day 11 | | Day 12 | | Total | |
|---|---|---|---|---|---|---|---|---|---|---|---|---|
| μg/ml | Male | Female | Male | Female | Male | Female | Male | Female | Male | Female | Male | Female |
| 0.1 | 88 | 1 | 135 | 0 | 123 | 0 | 128 | 0 | 114 | 0 | 1229 | 1 |
| 1 | 101 | 0 | 127 | 2 | 84 | 0 | 101 | 0 | 79 | 0 | 1137 | 4 |
| 5 | 80 | 0 | 94 | 0 | 127 | 0 | 128 | 3 | 86 | 0 | 1230 | 5 |
| 20 | 132 | 0 | 81 | 0 | 88 | 0 | 112 | 0 | 127 | 0 | 1214 | 2 |
| 100 | 106 | 1 | 132 | 0 | 81 | 0 | 115 | 0 | 107 | 0 | 1348 | 40 |
| 500 | 115 | 2 | 98 | 0 | 86 | 0 | 82 | 4 | 115 | 0 | 1184 | 99 |
| 1000 | 131 | 3 | 104 | 1 | 99 | 0 | 125 | 0 | 108 | 0 | 1216 | 165 |
| 2000 | 91 | 8 | 88 | 2 | 85 | 5 | 114 | 0 | 80 | 0 | 1198 | 309 |

Yp3-tTA, tRE-Msl-1$^{Mpu}$ on the second chromosome.

Conclusions

These data show that feeding the mothers high concentrations of tetracycline has some protective effect, but that all these recombinant chromosomes work extremely efficiently over a wide range of (parental) tetracycline concentrations, with the sole exception of "Yp3 tTa, tRe Msl-1$^{Mpu}$ on the 2$^{nd}$ chromosome", which has some (<1%) escapers even at low tetracycline concentrations. Since there is no meiotic recombination in Drosophila melanogaster males, any of these recombinant chromosomes could be used in a genetic sexing or insect control program, if required. In practice, Drosophila melanogaster is not an agricultural pest or disease vector, but these data demonstrate that the effective elimination of one sex can be achieved by this method.

Example 4

Use of Non-Antibiotic Tetracycline Analogues

Recombinant chromosome stocks can readily be maintained at 25° C. on epioxytetracycline concentrations of 1 μg/ml or anhydrotetracycline concentrations of 0.1 μg/ml, showing that these non-antibiotic tetracycline analogues are effective in repressing tTA responsive gene expression.

Epioxytetracycline

A standard range of additive concentrations were used in the following experiments (0.05-20 μg/ml). We were unable to maintain stock at two lowest concentrations, so marked n.d. (="not done")

| Epioxytetracycline Conc. μg/ml | Female | Male |
|---|---|---|
| 0.05 | n.d. | n.d. |
| 0.1 | n.d. | n.d. |
| 1 | 0 | 1306 |
| 5 | 0 | 1581 |
| 20 | 0 | 1495 |

Sxlp$^e$ tTa, tRe Ras64B$^{V12}$ on the X chromosome

| Epioxytetracycline Conc. μg/ml | Female | Male |
|---|---|---|
| 0.05 | n.d. | n.d. |
| 0.1 | n.d. | n.d. |
| 1 | 0 | 1165 |
| 5 | 0 | 1279 |
| 20 | 0 | 1257 |

Sxlp$^e$ tTa, tRe Ras64B$^{V12}$ on the 3$^{rd}$ chromosome

| Epioxytetracycline Conc. μg/ml | Female | Male |
|---|---|---|
| 0.05 | n.d. | n.d. |
| 0.1 | n.d. | n.d. |
| 1 | 0 | 1076 |
| 5 | 0 | 1119 |
| 20 | 0 | 1159 |

Sxlp$^e$ tTa, tRe Msl-2$^{Nopu}$ on the X chromosome

| Epioxytetracycline Conc. μg/ml | Female | Male |
|---|---|---|
| 0.05 | n.d. | n.d. |
| 0.1 | n.d. | n.d. |
| 1 | 0 | 1250 |
| 5 | 0 | 1300 |
| 20 | 0 | 1364 |

Sxlp$^e$ tTa, tRe Msl-2$^{Nopu}$ on the 3$^{rd}$ chromosome

| Epioxytetracycline Conc. μg/ml | Female | Male |
|---|---|---|
| 0.05 | n.d. | n.d. |
| 0.1 | n.d. | n.d. |
| 1 | 0 | 1483 |
| 5 | 0 | 1585 |
| 20 | 0 | 1565 |

Sxlp$^e$ tTa, tRe Msl-1$^{Mpu}$ on the X chromosome

| Epioxytetracycline Conc. μg/ml | Female | Male |
|---|---|---|
| 0.05 | n.d. | n.d. |
| 0.1 | n.d. | n.d. |
| 1 | 0 | 1362 |
| 5 | 0 | 1181 |
| 20 | 0 | 1403 |

Hsp26 tTa, tRe Msl-2$^{Nopu}$ on the 2$^{nd}$ chromosome

| Epioxytetracycline Conc. μg/ml | Female | Male |
|---|---|---|
| 0.05 | n.d. | n.d. |
| 0.1 | n.d. | n.d. |
| 1 | 0 | 1243 |
| 5 | 0 | 1409 |
| 20 | 0 | 1373 |

Hsp26 tTa, tRe Msl-1$^{Mpu}$ on the 2$^{nd}$ chromosome

| Epioxytetracycline Conc. μg/ml | Female | Male |
|---|---|---|
| 0.05 | n.d. | n.d. |
| 0.1 | n.d. | n.d. |
| 1 | 0 | 1431 |
| 5 | 0 | 1424 |
| 20 | 0 | 1387 |

Yp3 tTa, tRe Ras64B$^{V12}$ on the 2$^{nd}$ chromosome

| Epioxytetracycline Conc. μg/ml | Female | Male |
|---|---|---|
| 0.05 | n.d. | n.d. |
| 0.1 | n.d. | n.d. |
| 1 | 0 | 1350 |
| 5 | 0 | 1308 |
| 20 | 0 | 1343 |

Yp3 tTa, tRe Msl-1$^{Mpu}$ on the X chromosome

Anhydrotetracycline

| Anhydrotetracycline Conc. μg/ml | Female | Male |
|---|---|---|
| 0.05 | 0 | 1452 |
| 0.1 | 0 | 1528 |
| 1 | 0 | 1614 |
| 5 | 0 | 1448 |
| 20 | 5 | 1592 |

Sxlp$^e$ tTa, tRe Ras64B$^{V12}$ on the X chromosome

| Anhydrotetracycline Conc. μg/ml | Female | Male |
|---|---|---|
| 0.05 | 0 | 1381 |
| 0.1 | 0 | 1304 |
| 1 | 0 | 1121 |
| 5 | 0 | 1269 |
| 20 | 1 | 1247 |

Sxlp$^e$ tTa, tRe Ras64B$^{V12}$ on the 3$^{rd}$ chromosome

| Anhydrotetracycline Conc. μg/ml | Female | Male |
|---|---|---|
| 0.05 | 0 | 1114 |
| 0.1 | 0 | 1120 |
| 1 | 0 | 1130 |
| 5 | 0 | 1148 |
| 20 | 0 | 1128 |

Sxlp$^e$ tTa, tRe Msl-2$^{Nopu}$ on the X chromosome

| Anhydrotetracycline Conc. µg/ml | Female | Male |
|---|---|---|
| 0.05 | 0 | 1331 |
| 0.1 | 0 | 1431 |
| 1 | 0 | 1309 |
| 5 | 0 | 1359 |
| 20 | 1 | 1362 |

Sxlp$^e$ tTa, tRe Msl-2$^{Nopu}$ on the 3$^{rd}$ chromosome

| Anhydrotetracycline Conc. µg/ml | Female | Male |
|---|---|---|
| 0.05 | 0 | 1582 |
| 0.1 | 0 | 1499 |
| 1 | 0 | 1474 |
| 5 | 0 | 1619 |
| 20 | 5 | 1533 |

Sxlp$^e$ tTa, tRe Msl-1$^{Mpu}$ on the X chromosome

| Anhydrotetracycline Conc. µg/ml | Female | Male |
|---|---|---|
| 0.05 | 0 | 707 |
| 0.1 | 0 | 1457 |
| 1 | 0 | 1437 |
| 5 | 0 | 773 |
| 20 | 5 | 1447 |

Hsp26 tTa, tRe Msl-2$^{Nopu}$ on the 2$^{nd}$ chromosome

| Anhydrotetracycline Conc. µg/ml | Female | Male |
|---|---|---|
| 0.05 | 0 | 1492 |
| 0.1 | 0 | 1426 |
| 1 | 0 | 1418 |
| 5 | 0 | 1457 |
| 20 | 8 | 1499 |

Hsp26 tTa, tRe Msl-1$^{Mpu}$ on the 2$^{nd}$ chromosome

| Anhydrotetracycline Conc. µg/ml | Female | Male |
|---|---|---|
| 0.05 | 0 | 1449 |
| 0.1 | 0 | 1411 |
| 1 | 0 | 1397 |
| 5 | 0 | 1430 |
| 20 | 2 | 1428 |

Yp3 tTa, tRe Ras64B$^{V12}$ on the 2$^{nd}$ chromosome

| Anhydrotetracycline Conc. µg/ml | Female | Male |
|---|---|---|
| 0.05 | 0 | 1339 |
| 0.1 | 0 | 1263 |
| 1 | 0 | 1265 |
| 5 | 0 | 1284 |
| 20 | 0 | 1297 |

Yp3 tTa, tRe Msl-1$^{Mpu}$ on the X chromosome

| Anhydrotetracycline Conc. µg/ml | Female | Male |
|---|---|---|
| 0.05 | 0 | 1316 |
| 0.1 | 0 | 1358 |
| 1 | 0 | 1354 |
| 5 | 0 | 1344 |
| 20 | 1 | 1312 |

Yp3 tTa, tRe Msl-2$^{Nopu}$ on the 2$^{nd}$ chromosome

Conclusions

These data show that non-antibiotic analogues of tetracycline analogues can be used in place of tetracycline. In the case of epioxytetracycline, slightly higher concentrations are required to repress gene expression. Neither has parental transmission characteristics substantially different from tetracycline, allowing for the different effective concentrations.

Example 5

Effect of Temperature

All the preceding experiments were performed at 25° C., the standard temperature for *Drosophila* culture. However, the insects in the wild would clearly be exposed to varying temperatures, so we investigated the extent to which the efficiency of the system is affected by temperature. As with the recombinant chromosome experiments, 40-45 young virgin females and 20-25 young males raised at 25° C. upon food with the indicated tetracycline supplement were allowed to mate, then transferred to normal (tetracycline-free) food after 3-4 days. These flies were transferred to fresh vials of normal food every day. The numbers of male and female progeny emerging as adults in each vial were recorded. These experiments were performed at either 18° C. or 29° C.

18° C.

| Tetracycline Conc. µg/ml | Female | Male |
|---|---|---|
| 0.1 | 8 | 982 |
| 1 | 10 | 912 |
| 5 | 7 | 871 |

Sxlp$^e$ tTa, tRe Ras64B$^{V12}$ on the X chromosome

| Tetracycline Conc. µg/ml | Female | Male |
|---|---|---|
| 0.1 | 6 | 1065 |
| 1 | 9 | 1124 |
| 5 | 7 | 989 |

Sxlp$^e$ tTa, tRe Ras64B$^{V12}$ on the 3$^{rd}$ chromosome

| Tetracycline Conc. µg/ml | Female | Male |
|---|---|---|
| 0.1 | 6 | 695 |
| 1 | 8 | 816 |
| 5 | 8 | 785 |

Sxlp$^e$ tTa, tRe Msl-2$^{Nopu}$ on the X chromosome

| Tetracycline Conc. µg/ml | Female | Male |
|---|---|---|
| 0.1 | 2 | 973 |
| 1 | 9 | 985 |
| 5 | 5 | 983 |

Sxlp$^e$ tTa, tRe Msl-2$^{Nopu}$ on the 3$^{rd}$ chromosome

| Tetracycline Conc. µg/ml | Female | Male |
|---|---|---|
| 0.1 | 8 | 840 |
| 1 | 5 | 927 |
| 5 | 8 | 837 |

Sxlp$^e$ tTa, tRe Msl-1$^{Mpu}$ on the X chromosome

| Tetracycline Conc. µg/ml | Female | Male |
|---|---|---|
| 0.1 | 8 | 832 |
| 1 | 7 | 879 |
| 5 | 4 | 818 |

Hsp26 tTa, tRe Msl-2$^{Nopu}$ on the 2$^{nd}$ chromosome

| Tetracycline Conc. µg/ml | Female | Male |
|---|---|---|
| 0.1 | 6 | 628 |
| 1 | 3 | 614 |
| 5 | 5 | 712 |

Hsp26 tTa, tRe Msl-1$^{Mpu}$ on the 2$^{nd}$ chromosome

| Tetracycline Conc. µg/ml | Female | Male |
|---|---|---|
| 0.1 | 8 | 1152 |
| 1 | 12 | 1122 |
| 5 | 3 | 1225 |

Yp3 tTa, tRe Msl-2$^{Nopu}$ on the 2$^{nd}$ chromosome

| Tetracycline Conc. µg/ml | Female | Male |
|---|---|---|
| 0.1 | 5 | 1303 |
| 1 | 14 | 1218 |
| 5 | 7 | 1386 |

Yp3 tTa, tRe Msl-1$^{Mpu}$ on the X chromosome

| Tetracycline Conc. µg/ml | Female | Male |
|---|---|---|
| 0.1 | 2 | 1190 |
| 1 | 4 | 1213 |
| 5 | 0 | 1058 |

Yp3 tTa, tRe Ras64B$^{V12}$ on the 2$^{nd}$ chromosome

29° C.

| Tetracycline Conc. µg/ml | Female | Male |
|---|---|---|
| 0.1 | 0 | 716 |
| 1 | 0 | 711 |
| 5 | 0 | 715 |

Sxlp$^e$ tTa, tRe Ras64B$^{V12}$ on the X chromosome

Sxlp$^e$ tTa, tRe Ras64B$^{V12}$ on the 3$^{rd}$ chromosome

| Tetracycline Conc. µg/ml | Female | Male |
|---|---|---|
| 0.1 | 0 | 781 |
| 1 | 0 | 749 |
| 5 | 0 | 741 |

Sxlp$^e$ tTa, tRe Msl-2$^{Nopu}$ on the X chromosome

| Tetracycline Conc. µg/ml | Female | Male |
|---|---|---|
| 0.1 | 0 | 682 |
| 1 | 0 | 804 |
| 5 | 0 | 648 |

Sxlp$^e$ tTa, tRe Msl-1$^{Mpu}$ on the X chromosome

| Tetracycline Conc. µg/ml | Female | Male |
|---|---|---|
| 0.1 | 0 | 732 |
| 1 | 0 | 771 |
| 5 | 0 | 816 |

Sxlp$^e$ tTa, tRe Msl-2$^{Nopu}$ on the 3$^{rd}$ chromosome

| Tetracycline Conc. µg/ml | Female | Male |
|---|---|---|
| 0.1 | 0 | 749 |
| 1 | 0 | 737 |
| 5 | 0 | 718 |

Hsp26 tTa, tRe Msl-2$^{Nopu}$ on the 2$^{nd}$ chromosome

| Tetracycline Conc. µg/ml | Female | Male |
|---|---|---|
| 0.1 | 0 | 696 |
| 1 | 0 | 658 |
| 5 | 0 | 711 |

| Hsp26 tTa, tRe Msl-1$^{Mpu}$ on the 2$^{nd}$ chromosome | | |
|---|---|---|
| Tetracycline Conc. μg/ml | Female | Male |
| 0.1 | 0 | 733 |
| 1 | 0 | 776 |
| 5 | 0 | 728 |

| Yp3 tTa, tRe Msl-2$^{Nopu}$ on the 2$^{nd}$ chromosome | | |
|---|---|---|
| Tetracycline Conc. μg/ml | Female | Male |
| 0.1 | 0 | 765 |
| 1 | 0 | 702 |
| 5 | 0 | 773 |

| Yp3 tTa, tRe Msl-1$^{Mpu}$ on the X chromosome | | |
|---|---|---|
| Tetracycline Conc. μg/ml | Female | Male |
| 0.1 | 0 | 799 |
| 1 | 0 | 749 |
| 5 | 0 | 744 |

| Yp3 tTa, tRe Ras64B$^{V12}$ on the 2$^{nd}$ chromosome | | |
|---|---|---|
| Tetracycline Conc. μg/ml | Female | Male |
| 0.1 | 0 | 718 |
| 1 | 0 | 753 |
| 5 | 0 | 757 |

Conclusions

At low temperature there is a slight leakiness, but only at a level of <1% escapers. All versions are extremely effective at 29° C. This is important as many of the most important target species for control are tropical and are grown in culture at around 28° C., e.g. *Ceratitis capitata, Anopheles gambiae, Aedes aegypti*.

Example 6

The example illustrates maternal transmission of Tc and TC-repressible lethality using an embryo specific promoter.

Materials and Methods

Plasmid Construction

A bnk promoter fragment of approximately 2 kb was amplified from plasmid pW$^+$2.8 kb bnk rescue fragment (Schejter and Wieschaus, (1993), Cell 75, 373-385) using oligonucleotide primers 5'-GCCGAGCTCTTGACGGT-TGAAGTACGAATG-3' (SEQ ID NO:7) and 5'-CGGCCAT-TCATATGCGTATATTCACTATG-3' (SEQ ID NO:8). This fragment was digested with and subcloned as a SacI-XhoI fragment into pUHD15-1 (Gossen and Bujard, (1992), Proc Natl Acad Sci USA 89, 5547-51). A XhoI-HpaI fragment containing bnk-tTa was subcloned from this into pW8 (Klemenz et al., (1987), Nucl. Acids Res. 15, 3947-59) digested with XhoI and HpaI to create pP{bnk-tTa}.

W.T.P-2 (Bello et al., (1998), Development 125, 2193-2202) was modified by the addition of two complementary oligonucleotides (5'-AATTGCCACCATGGCTCATATG-GAATTCAGATCTG-3' (SEQ ID NO:9) and 5'-GGCCGCA-GATCTGATTCCATATGAGCCATGGTGGGC-3'(SEQ ID NO:10)) between the EcoRI and NotI sites to provide a consensus translation start sequence (Kozak, (1987), Nucleic Acids Res 15, 8125-48). A cDNA containing the entire coding region of a *Drosophila* homologue of Nipp1 (Van Eynde et al., (1995), J Biol Chem 270, 28068-74) in pNB40 (Brown and Kafatos, (1988), J. Mol. Biol. 203, 425-437) was isolated using the method of (Alphey, (1997), BioTech. 22, 481-486) based on a partial sequence obtained by a two-hybrid screen for *Drosophila* PP1c-binding proteins (Alphey et al., (1997), J. Cell Biol. 138, 395-409). The entire coding region and 3'UTR was cloned between the NdeI and NotI sites of W.T.P-2, modified as above, to create pP{tRe-Nipp1Dm}.

*Drosophila* Culture

Flies were reared on standard yeast/cornmeal/agar food with a yeast concentration of 45-50 gl$^{-1}$. Tc-containing food was made to the same recipe with the addition of tetracycline hydrochloride (Sigma-Aldrich) solution to the appropriate final concentration.

Histochemistry

Embryonic progeny from bnk-tTA/tRe-lacZ crosses were collected at 12 h intervals and then stained for β-galactosidase as described in Ashburner, (1989), Cold Spring Harbor, N.Y.: Cold Spring Harbor Laboratory Press.

Results

Maternal Transmission of Tetracycline

A mass-reared insect strain homozygous for a dominant lethal gene or genetic system will have no progeny when mated to wild insects. In this respect the time of action of the lethal gene is irrelevant. However, for the mass-reared insects to be useful as a control agent we consider that the time of action of the dominant lethal may be highly important. A lethal phase in adulthood may kill or at least reduce the fitness of the released adults prior to mating. This would clearly be counter-productive. Many agricultural pests damage crops through the feeding of their larval stages. It would therefore be desirable to kill the progeny as early as possible, preferably as embryos. However, embryos do not feed and so will not take up a dietary repressor (tetracycline) of the lethal genetic system. Insect embryos are also impermeable to most macromolecules, so exogenous tetracycline will not penetrate. In view of the advantages of an embryonic lethal phase, we tested whether tetracycline ingested by a female *Drosophila* could pass into her eggs and hence her progeny at sufficient concentration to suppress the phenotype of a Tc-repressible gene.

We used a strain of *Drosophila* in which females, but not males, require Tc for viability. Female-specific lethality is due to the expression of a toxic gene (Ras64B$^{V12}$, (Matsuo et al., (1997), Development 124, 2671-80) in the fat body of female larvae and adults (Thomas et al., (2000), Science 287, 2474-2476). Growing this strain on food supplemented with 0.1 μg/ml Tc is sufficient to suppress expression of the toxic gene, allowing both males and females to survive. We reasoned that if Tc ingested by a female *Drosophila* could pass into her eggs and hence her progeny, it might be possible to load the eggs with a high enough concentration to allow survival of the progeny even on media lacking Tc. We found that allowing parents to feed on food supplemented with Tc at 500 μg/ml or higher led to the survival of a small proportion of female progeny (Table 1). We tested several other lines and other promoter-killer gene combinations with similar results (data not shown). We concluded that it is possible by feeding a female Tc to introduce enough Tc into her progeny to repress tTa-dependent gene expression.

Embryo-Specific Expression of tTa

Of the many genes known to be expressed in *Drosophila* embryos, the huge majority are also expressed later. For example, the well-known developmental genes involved in laying down the basic body plan of the embryo are re-used later to pattern the appendages and the imaginal disks that will form adult structures. For many other embryonic genes the possibility of later expression has not been rigorously investigated. bottleneck (bnk) is one of a relatively small number of genes reportedly expressed exclusively in embryos. bnk is required for actin filament reorganisation during the cellularisation of the Drosophila embryo between nuclear cycles 13 and 14 (Schejter and Wieschaus, (1993), Cell 75, 373-385). Its transcript is present at high levels only from nuclear cycles 11 to 14. We constructed stable transformed lines of flies carrying the tTa open reading frame under the control of a bnk promoter fragment. The ability of bnk-tTa to activate transcription in the embryo and at other developmental stages was monitored by using a tTa-responsive reporter constructs, tRe-lacZ (Bello et al., (1998), Development 125, 2193-2202). We found that tTa protein was expressed in the embryo and that it could direct expression of the reporter construct.

tTa-dependent transcriptional activation is repressed by Tc. tTa binds to a specific DNA sequence, the tetracycline responsive element (tRe). Tc binds to tTa and this prevents the tTa protein binding to DNA. We therefore attempted to repress reporter gene expression either by supplementing the parents' food with Tc or by seeding the embryos onto media supplemented with Tc. Effective repression of the reporter genes was achieved by placing the parents on media containing 1 μg/ml Tc for at least two days prior to embryo collection. Seeding embryos onto media containing Tc did not appear to affect reporter gene expression. These data suggest that Tc can enter the egg through the mother during oogenesis and can affect tTa-mediated transcription at early stages of development, but Tc cannot diffuse into embryos from the substrate onto which they are laid.

A "Killer Gene" Active in Embryos

In order to construct a maternal Tc-dependent dominant lethal genetic system, we crossed flies carrying stable insertions of bnk-tTa to flies carrying insertions of tRe-Ras64B$^{V12}$. Our previous studies had shown that tRe-Ras64B$^{V12}$ is toxic at later stages in combination with a range of female-specific and non-sex-specific tTa lines (Thomas et al., (2000), Science 287, 2474-2476). To our surprise, embryos carrying bnk-tTa and tRe-Ras64B$^{V12}$ survived to adulthood irrespective of parental or zygotic exposure to Tc (Table 2 and data not shown). In view of the embryonic reporter gene expression above we concluded that expression of Ras64B$^{V12}$ is not toxic, or not sufficiently toxic, during the period when bnk-tTa is active to cause embryonic lethality.

As ectopic Ras64B$^{V12}$ apparently lacks embryonic toxicity under the conditions we are using, we placed a different toxic gene under the control of tRe. We chose to use Nipp1Dm, a Drosophila homolog of mammalian NIPP-1, a nuclear inhibitor of protein phosphatase type 1 (Beullens et al., (1992), J. Biol. Chem. 267, 16538-16544; Van Eynde et al., (1995), J Biol Chem 270, 28068-74). NIPP1 has several advantages as a "killer gene" in this system. Flies carrying homozygous insertions of bnk-tTa or tRe-Nipp1 were crossed to each other. Flies fed on media supplemented with Tc produced viable $F_1$ progeny; those on media not supplemented with Tc did not (Table 2). Furthermore, $F_1$ survival was not affected by the presence or absence of Tc in the media on which the $F_1$ were raised. We have therefore constructed an efficient dominant lethal genetic system repressible by parental dietary Tc.

TABLE 1

High doses of maternal Tc can suppress tTa in progeny.

| Tc conc. μg/ml | Day 1 ♂ | Day 1 ♀ | Day 2 ♂ | Day 2 ♀ | Day 3 ♂ | Day 3 ♀ | Day 4 ♂ | Day 4 ♀ | Day 5 ♂ | Day 5 ♀ | Day 6 ♂ | Day 6 ♀ | Day 7 ♂ | Day 7 ♀ |
|---|---|---|---|---|---|---|---|---|---|---|---|---|---|---|
| 0.1 | 93 | 0 | 119 | 0 | 112 | 0 | 141 | 0 | 100 | 0 | 126 | 0 | 89 | 0 |
| 1 | 117 | 0 | 135 | 0 | 122 | 0 | 121 | 0 | 127 | 0 | 101 | 0 | 136 | 0 |
| 5 | 112 | 0 | 116 | 0 | 128 | 0 | 111 | 0 | 136 | 0 | 113 | 0 | 130 | 0 |
| 20 | 89 | 0 | 107 | 0 | 107 | 0 | 98 | 0 | 88 | 0 | 102 | 0 | 107 | 0 |
| 100 | 129 | 0 | 136 | 0 | 128 | 0 | 127 | 0 | 135 | 0 | 144 | 0 | 107 | 0 |
| 500 | 136 | 2 | 88 | 0 | 113 | 0 | 113 | 0 | 87 | 0 | 94 | 0 | 109 | 0 |
| 1000 | 107 | 13 | 140 | 5 | 110 | 0 | 141 | 0 | 98 | 0 | 129 | 0 | 88 | 0 |
| 2000 | 119 | 32 | 102 | 15 | 107 | 12 | 109 | 9 | 109 | 8 | 140 | 2 | 127 | 0 |

| Tc conc. μg/ml | Day 8 ♂ | Day 8 ♀ | Day 9 ♂ | Day 9 ♀ | Day 10 ♂ | Day 10 ♀ | Day 11 ♂ | Day 11 ♀ | Day 12 ♂ | Day 12 ♀ | Total ♂ | Total ♀ |
|---|---|---|---|---|---|---|---|---|---|---|---|---|
| 0.1 | 105 | 0 | 133 | 0 | 93 | 0 | 131 | 0 | 121 | 0 | 1363 | 0 |
| 1 | 90 | 0 | 119 | 0 | 94 | 0 | 98 | 0 | 100 | 0 | 1360 | 0 |
| 5 | 119 | 0 | 96 | 0 | 88 | 0 | 144 | 0 | 91 | 0 | 1384 | 0 |
| 20 | 135 | 0 | 126 | 0 | 143 | 0 | 123 | 0 | 141 | 0 | 1366 | 0 |
| 100 | 96 | 0 | 92 | 0 | 104 | 0 | 94 | 0 | 115 | 0 | 1407 | 0 |
| 500 | 141 | 0 | 144 | 0 | 123 | 0 | 104 | 0 | 124 | 0 | 1376 | 2 |
| 1000 | 138 | 0 | 105 | 0 | 124 | 0 | 115 | 0 | 114 | 0 | 1409 | 18 |
| 2000 | 114 | 0 | 123 | 0 | 132 | 0 | 115 | 0 | 107 | 0 | 1404 | 78 |

A strain homozygous for second chromosome insertions of both Yp3-tTA and tRe-Ras64B$^{V12}$ was tested for the effect of parental dietary Tc. 40-45 young females and 20-25 young males raised at 25° C. upon food with the indicated tetracycline supplement were allowed to mate, then transferred to normal (tetracycline-free) food after 3-4 days. These flies were transferred to fresh vials of normal food every day for 12 days, and then removed on the 13th day. All the vials were incubated at 25° C. while the progeny developed. The total numbers of male and female progeny emerging as adults were recorded. Survival of female progeny clearly depends on the Tc concentration on which their parents were raised, and on the length of time between removal of the parents from Tc media and egg laying.

TABLE 2

Tc-repressible lethality using an embryo-specific promoter.

| | Tc (µg/ml) | Males | Females |
|---|---|---|---|
| bnk-tTa x tRe-Nipp1Dm | 0 | 0 | 0 |
| | 0.1 | 60 | 58 |
| | 1.0 | 78 | 82 |

Males homozygous for bnk-tTa were mated with females homozygous for either tRe-Ras64B$^{V12}$ or tRe-Nipp1Dm. These flies were raised on media lacking Tc, but before mating were placed on food containing various concentrations of Tc. They were allowed to lay embryos on this food for 9 days, and then the parents were removed. Their adult progeny of each sex were counted. In combination with bnk-tTa, tRe-Nipp1Dm gives Tc-repressible lethality of both sexes, but tRe-Ras64B$^{V12}$ does not.

Example 7

Modular Transformation Vector

This example details the construction of a vector suitable for transformation to produce an organism containing the lethal genetic system of the invention.

The purpose of this modular vector is to allow the rapid creation of a transformation construct suitable for a given species. In this example, the intention is to create a dominant repressible lethal. This is achieved by inserting a suitable promoter into this construct, then using it to transform the target species. The promoter is typically derived from the target species itself, which is probably the most direct and safest way to ensure that the promoter has the desired specificity (e.g. female-specific) in the target species. This is not, however, necessary and indeed in the example below we have used a modified actin gene promoter from the silk moth Bombyx mori, with the intention of using it in pink bollworm, a pest of cotton.

PiggyBac as been used successfully to transform a wide range of insects, including Diptera, Coleoptera and Lepidoptera, but it is not necessarily optimal, nor will Act5C-EGFP be the optimum transformation marker in every case. The plasmid has been constructed such that the core elements of the system (tTa, tRe-Nipp1 and insulators) are flanked by unique sites for rare-cutting restriction enzymes (NotI and the SbfI-PmeI-AscI multiple cloning site) to facilitate subcloning these elements into a new transformation vector. Similarly, alternative insulators could be used or an additional insulator inserted 5' of the new promoter, to protect against position effects from flanking chromatin.

The general arrangement of the vector is shown in FIG. 1, and elements are as follows:

tTa comprises: tTa open reading frame and SV40 polyA signal, both from pUHD15-1neo (Gossen and Bujard, 1992) as EcoRI-BamHI. pUHD15-1 was digested with XhoI and EcoRI and a oligo pair inserted which destroyed both these sites and created an AscI site. This plasmid (pUHD15Asc) was digested with HpaI and BamHI and another oligo pair inserted:

```
tTa 3'linker+
                                            (SEQ ID NO: 11)
5'-gcggccgc ac gggccc a ctcgag cac aagctt c ggtacc ac gaattc-3' tTa 3'linker-
                                            (SEQ ID NO: 12)
5'-agct gaattc gt ggtacc g aagctt gtg ctcgag a gggccc gt gcggccgc-3'
to create pUHD15Asc3'linker#42.
``` tRe-Nipp1Dm comprises: tRe vector W.T.P-2 from Bruno Bello (Bello et al., (1998), Development 125, 2193-2202) modified by insertion of oligo pair "Kozak Spe+/–" between EcoRI and NotI site to give pWTP-KozakSpe. This provides consensus translation start sequence.

```
Kozak Spe+/-:
                                            (SEQ ID NO: 13)
5'-aattgccaccatggaattcactagtgc-3'

(SEQ ID NO: 14)
3'-cggtggtaccttaagtgatcacgccgg-5'
```

Nipp1Dm cDNA in pNB40 (Brown and Kafatos, (1988), J. Mol. Biol. 203, 425-437) modified to have EcoRI site at start codon, then subcloned as EcoRI-{endfilled NotI} into pWTP-KozakSpe cut with EcoRI and StuI. tRe-Nipp1Dm-hsp70 polyA fragment excised as partial XhoI-HindIII and subcloned into pUHD15Asc3' linker#43 cut with XhoI and HindIII to give ptTatReNipp1#77. The complete predicted sequence of this fragment is appended. Nipp1Dm DNA may be readily prepared by RT-PCR or PCR from genomic DNA using this sequence.

piggyBac and plasmid vector are derived from p3E1.2-white (Handler et al., (1998), Proc Natl Acad Sci USA 95, 7520-5) from Al Handler. The medfly white gene, originally inserted as a NotI fragment into the HpaI site of piggyBac, using linkers, was removed by digestion with NotI and recircularising. A set of extraneous restriction sites vector sequences (outside piggyBac) was removed by digesting with EcoRI and SalI, end-filling and recircularising, giving p3E1ΔRI-Sal. This plasmid was then digested with BagleyI and NotI and an oligo pair inserted to add useful restriction sites:

piggy linker 2+/-:

(SEQ ID NO: 15)
5'-ggcc ctcgag aga aggcct gcggccgc tgt ggcgcgcc aga gtttaaac agt cctgcagg-3'

(SEQ ID NO: 16)
3'-gagctc tct tccgga cgccggcg aca ccgcgcgg tct caaatttg tca ggacgtcc ctag-5' the resulting plasmid is pPB-linker2#93.

The Act5C-EGFP transformation marker was added by subcloning as a 4.2 kb XhoI-EcoRV fragment from Act5C-EGFP in pP{CaSpeR} (Jean-Marc Reichhart) into XhoI-StuI cut pPB-linker2 to give pPB-Act5CEGFP#181.

The HS4 insulator was added by cutting pJC13-1 (Chung et al., (1993), Cell 74, 505-14) from Gary Felsenfeld with BamHI and recircularising, to remove the neo reporter, then excising an HS4 dimer (2×1.2 kb=2.4 kb total) as {endfilled SalI}-KpnI and subcloning into ptTatReNipp1#77 incubated sequentially with HindIII, Klenow DNA polymerase and KpnI (i.e. KpnI cohesive end—endfilled HindIII) to give ptTatReNipp1HS4#101.

The apoB insulator was added by changing the SpeI site of apoB3'MAR (Namciu et al., (1998), Mol Cell Biol 18, 2382-91) from Stephanie Namciu to ApaI using the oligo SpeI-ApaI:

SpeI-ApaI:
(SEQ ID NO: 17)
CTAGAAGGGCCCTT

The apoB insulator was then subcloned as a 0.8 kb ApaI-NotI fragment into ApaI-NotI digested ptTatReNipp1HS4#101.

An AscI-NotI fragment from ptTatReNipp1HS4#101 was subcloned into pPB-Act5CEGFP#181 to give pRIDL#204

Examples of Inserting a Promoter:

1) A BmA³ promoter fragment of approximately 190 bp was amplified by PCR from pJP88 (John Peloquin) (Peloquin et al., (2000), Insect Mol Biol 9, 323-33) using Platinum Pfx polymerase (Life Technologies) and the oligos:

BmA3 5':
(SEQ ID NO: 18)
5'-aaacAATTCTGATAGCGTGCGCGTTAC-3'

BmA3 3'Asc-2:
(SEQ ID NO: 19)
5'-ggtaggcgcgcc TGGCGACCGGTGGATCCGAATG-3'

Tzhis PCR product was digested with AscI and subcloned into AscI-PmeI digested pRIDL#204 to give pRIDL-BmA³

2) An *Aedes aegypti* Vg1 promoter fragment, previously used by us to give female-specific expression in the yellow fever mosquito *Aedes aegypti*, using Platinum Pfx polymerase (Life Technologies) and the oligos:

*Aedes* vg5'
aaac gaattcaccaccaggcagtg (SEQ ID NO:20)

*Aedes* vg3'AscI
ggaggcgcgcc tcaagtatccggcagctgttc (SEQ ID NO:21)

This PCR product was digested with AscI and subcloned into AscI-PmeI digested pRIDL#204 to give pRIDL-A.a.Vg1

For use in plants, the minimal promoter used in combination with the tetO repeats would be a suitable plant minimal promoter. For long-term stability of expression this would preferably be a minimal promoter not subject to gene silencing. The promoter driving tTa expression would suitably be a plant promoter, e.g. the A9 promoter for tapetum-specific expression in a system designed to eliminate pollen production in the absence of the repressor.

The Predicted Sequence of tRe-Nipp1. (XhoI-HindIII)

nt 1-543 derived from W.T.P.-2 (Bello et al., (1988), Development 125:2193), of which 1-309 contains 7 repeats of the tet operator sequence (tetO), followed by 98 nt of P element transposase core promoter, from Carnegie 4, −52/+51 relative to transcription start, linked by a SmaI-PstI linker (synthetic oligonucleotide, GGGCTGCAG) to the leader sequence of hsp70 from CaSpeR-hs (Thummel and Pirrotta, (1991), Dros. Inf. News. 2) up to the EcoRI site of its polylinker. The next section is derived from a synthetic oligonucleotide and provides a consensus translation start and some restriction sites, followed by the coding region of *Drosophila* Nipp1 and 3' UTR to polyA sequence from an unpublished cDNA in pNB40 (Brown and Kafatos, (1988), J. Mol. Biol. 203:425) up to the NotI site, which has been end-filled and cloned into an StuI site. The StuI site and subsequent sequence is from W.T.P-2 and is derived from CaSpeR-hs, it is principally trailer (3' UTR) sequence from hsp70 flanked by some restriction sites.

(SEQ ID NO: 22)
CTCGAGTTTACCACTCCCTATCAGTGATAGAGAAAAGTGAAAGTCGAGTTTACCACTCCCTATC
AGTGATAGAGAAAAGTGAAAGTCGAGTTTACCACTCCCTATCAGTGATAGAGAAAAGTGAAAGT
CGAGTTTACCACTCCCTATCAGTGATAGAGAAAAGTGAAAGTCGAGTTTAGGAGTCCCTATCAG
TGATAGAGAAAAGTGAAAGTCGAGTTTACCACTCCCTATCAGTGATAGAGAAAAGTGAAAGTCG
AGTTTACCACTCCCTATCAGTGATAGAGAAAAGTGAAAGTCGAGCTCGGTACGCTTACCGAAGT
ATACACTTAAATTCAGTGCACGTTTGCTTGTTGAGAGGAAAGGTTGTGTGCGGACGAATTTTTT
TTTGAAAACATTAACCCTTACGGGCTGCAGTAAAGTGCAAGTTAAAGTGAATCAATTAAAAGTA
ACCAGCAACCAAGTAAATCAACTGCAACTACTGAAATCTGCCAAGAAGTAATTATTGAATACAA
GAAGAGAACTCTGAATAGGGAATTGGGAATTGCCACCATGGCTCATATGGAATTCATGGCTAAC
AGCTACGACATACCCAGTTGGGCTGGAAAACCGCCCACTGGCTTACATCTGGATGTGCTAAAGG
ACGACAAACTAGTACAAAAACTGATGGTGGATGAAAAAAGATGCTATCTATTTGGTCGCAACAG
TCAAATGAACGACTTCTGCATAGACCATGCCTCTTGTTCGCGGGTCCACTCGGCGTTTGTCTAC
CACAAGCACCTCAACATAGCCTACCTCGTGGATCTGGGGTCCACTCATGGCACCTTTATTGGAA
CACTCAGATTGGAAGCGCACAAGCCCACACAGCTGCAGATTAATAGCACCTTCCACTTTGGGGC
TTCTACCCGGAACTACATACTCAGGGAACGACCCTCTGGCCACCACAGCAACATCATGGAAGAC
CTGCCGCTCAGTGAAACCAGCGATGGCGCTCTCCTGGGCCTGCCCGAAAGCCAAACGGAGCTTG
ATAATCTTACAGAATACAACACGGCCCACAATCGGCGCATCTCAATGCTGGGCATCGATGATGA
TACCAATATGCGAAAGCAAAACGCCTTGAAACAGGGACGGCGCACTCGAAATGTCACATTTAAC
GATGAGGAGATTGTCATCAATCCTGAGGATGTGGATCCTAATGTGGGACGCTTCAGGAACTTGG
TACAAACCACTGTGGTGCCCGCCAAGAGGGCTCGCTGCGACGTCAACCATATGGGCATCCATTC
GGGCAACAGCAGTTTGTCCAGTGCCAATGCCGCACATGTACACCAAATGTTCCAGCAGAGCCTA
GTTGACATGAAGCAGCAGCATAGGGAAATGCCTCCGCCCAATGCGGTGCTCCACTCGCCTACTA
ATTCCCTATATCAAGGTCTACCGGCCGAAATGCATGGCAAGGGTGACCTAGAGCCCATCTCCCC
GCTGAGCATTGGTTCCAAGTTGGGCCTATTGCTCCCGAATCCTGCGCCTGAAGTGTCGCCAGTC
TATGACGAAGCTGTGGAGACCTCGACATTGGCTCAAAAGTTGGCCGTCGCTAATGCAAACGTTC
GTCGCTTCGGTGAGGATCCGCATGACTCGAGTGGCGAGGGCGATTCGCTGTGCCCACAGAAAAA
GAAATACGCCAAGGAAGCATGGCCAGGTCGCAAGCCCATGTTGGGGCAGCTGTAATTGCGTATT
AACAAAATAATTAAGATTCCACCTACGATTTTCTCAAGCATATGATTGACAACACACTCTGGAG
TAATATTTGTTTATTAGACTTTTAACGTAAAACAAAAAAAAAAAAAAAAAAAAAAAAAAAAAAA
AAAAACGAATGCTGCGGCCCCTAATTCCAGCTGAGCGCCGGTCGCTACCATTACCAGTTGGTCT
GGTGTCGGGATCCGTCGACTAAGGCCAAAGAGTCTAATTTTTGTTCATCAATGGGTTATAACA
TATGGGTTATATTATAAGTTTGTTTTAAGTTTTTGAGACTGATAAGAATGTTTCGATCGAATAT
TCCATAGAACAACAATAGTATTACCTAATTACCAAGTCTTAATTTAGCAAAAATGTTATTGCTT
ATAGAAAAATAAATTATTTATTTGAAATTTAAAGTCAACTTGTCATTTAATGTCTTGTAGACT
TTTGAAAGTCTTACGATACATTAGTATCTATATACATGGTTCATTCTACATTCTATATTAGTGA
TGATTTCTTTAGCTAGTAATACATTTTAATTATATTCGGCTTTGATGATTTTCTGATTTTTTCC
GAACGGATTTTCGTAGACCCTTTCGATCTCATAATGGCTCATTTTATTGCGATGGACGGTCAGG
AGAGCTCGAATTAACGGGGATCCGTCGACCTGCAGCCCAAGCTT

Example 8

Models of Insect Control

Methods

Thomas et al. (Science 287, 2474-2476, 2000) presented a simple mathematical model for the effectiveness of insect control programs including SIT and various forms of 'RIDL' (='release of insects carrying a dominant lethal'—used here to indicate the organism and method of the present invention), and mentioned that enhanced systems could also be considered, including released males being homozygous for dominant female lethals (DFLs) at multiple unlinked loci and linking of the DFL to a meiotic drive/segregation distortion system (Thomas et al., 2000, Science 287, 2474-2476). We consider here the impact of these and other system enhancements on the effectiveness of insect control.

In general, we assume that all control programs release a constant number of males per pest generation (see below). This number ("input") is given relative to the initial male pest population. The model considers discrete generations.

Females are assumed to select mates proportionately to their abundance and fitness such that a female will choose a mate of type i with probability $p_i$, such that:

$$p_i = n_i r_i / (S_j n_j r_j)$$

where $n_i$ is the number of male insects of type i and $r_i$ is the fitness of type i relative to wild type males taken to have a fitness of 1. The type of insect may depend on its genotype as well as its generation—in particular, we will consider scenarios in which released flies have reduced fitness but their male progeny, regardless of genotype, have the same fitness as wild type males.

We consider two scenarios for fertility. In the density-dependent case, we assume that each female mating with a fertile male produces $R_0$ female offspring—of which the proportion $s_i$ survive to adulthood where $s_i$ is given by:

$$s_i = 1/(1+(ao_i)^b)$$

where $o_i$ is the number of offspring surviving to the point at which density dependence acts (Maynard Smith and Slatkin, 1973 Ecology 54, 384-391), and a and b are parameters. Rogers and Randolph (1984 Insect Sci. Applic. 5, 419-23) consider such a density-dependent system with an SIT program and show that the effectiveness of the SIT program is largely determined by the natural resilience of the target insect population, characterized by the parameter b (Rogers and Randolph, 1984 Insect Sci. Applic. 5, 419-23). An important consideration is the timing of the density dependent mortality, in particular, whether the released males are released before or after the density dependent mechanism acts and whether the RIDL-induced mortality is achieved before or after the density-dependent mechanism acts. In the absence of control, such a population will remain constant if at its carrying capacity ($s_i = 1/R_0$) and will tend to return to that level if perturbed. This would be an appropriate model for an established population. This does not necessarily mean that no control has been attempted—control methods such as breeding site elimination will reduce the stable level of the population, rather than the size of the population relative to the stable level.

In the density-independent case, we assume that each female mating with a fertile male produces $R_0$ female offspring all of which survive to adulthood in the next generation. This is essentially the limit of the density dependent case—in which the population is so small that there is essentially no density-dependent mortality and $s_i \approx 1$. Thus, in the absence of control, if $R_0$ is greater than 1, the population will expand exponentially. This would be an appropriate model for a new introduction or outbreak of a pest species, or a population recovering from a severe depletion, e.g. due to a short intensive control programme designed to reduce the numbers of the target species prior to a RID L or SIT programme.

For example, for a very simple system with no density dependence, $R_0$ equal to 2 and an input of 1.5 sterile males at each generation, the model would work in the following manner:

(i) The initial population consists equally of wild type males and wild type females. All numbers are counted relative to the initial female population, so this is 1.0 by definition and the initial wild type male population is here also 1.0. Since we are only considering populations which normally have equal numbers of males and females, the initial population of males is always 1.0 in these examples.

(ii) An input of 1.5 sterile males is made, which is to say 1.5 times as many males as there are females in the initial population (iii) 60% of females mate with sterile males (since of the 2.5 males, 60% are sterile) and produce no offspring. 40% of females mate with wild type males to produce 0.8 female offspring ($0.8 = R_0*(0.4*1)$ females mating with wild type males). They also produce 0.8 male offspring.

(iv) Thus the second generation consists equally of wild type males and females (0.8 of each).

(v) An input of 1.5 sterile males is made.

(vi) 65% of females mate with sterile males (since of the 2.3 males, 65% are sterile) and produce no offspring. 35% of females mate with wild type males to produce 0.56 female offspring ($0.56 = R_0*(0.35*0.8)$ females mating with wild type males). They also produce 0.56 male offspring.

and so on until the population is eliminated.

SIT

In each case we compare the effectiveness of various versions of the RIDL system with that of SIT. For SIT we consider an optimal case with perfect sex-separation, and 100% sterility. Such SIT is itself a highly effective control method, and we also consider the level which the population would have achieved in the absence of any control, but we show that various versions of RIDL are much more effective, and there are many situations in which RIDL can control a pest population where SIT cannot. These models do not take into account some additional advantages of RIDL, for example the greater ease of transporting the system to a new species (see vector of Example 7)

Input

In general we assume that all control programs release a constant number of males per pest generation. This number ("input") is given relative to the initial male pest population. One potential RIDL strategy involves the release of a mixed-sex population, in the knowledge that one sex will be killed by the lethal effect of a sex-specific lethal genetic system at some later point in its life cycle, e.g. prior to sexual maturity. In the instance where these individuals can induce density-dependent mortality in their conspecifics, (FIGS. 6a and 7a) we assume that an equal number of females are released in addition to the males.

The ability to release at any life cycle stage allows another strategy in which individuals are stored in a dormant state then released simultaneously, allowing a larger release than would otherwise be the case. For example, embryos of many mosquito species can be stored for months in relatively dry conditions with little loss of viability, then hatching and larval development induced simply by placing them in an aqueous environment. One major advantage of this approach is that a mass-rearing facility could continue to operate during the winter, while the target insects are in diapause and hence insensitive to a sterile release. In the spring, a much larger release could then be used, employing the stored embryos from several generations. Here, we model the consequences of storing two generations-worth of factory output and using this to double the size of the first two release generations (FIG. 8). Though the ability to store embryos is not specific to RIDL, an SIT programme would normally need to grow these embryos up to a later developmental stage in order to sterilize them by irradiation. Since factory rearing space, rather than the availability of embryos, is likely to be the limiting factor, the potential of a RIDL programme to release at any life cycle stage is critical to this novel strategy. In FIG. 8 we have nonetheless considered the advantage such a release strategy would confer on a conventional SIT programme. Each of the plots in FIG. 8 are based on an earlier plot with a double-sized release in the first two generations. To compare with conventional SIT without such a double-sized release, compare these plots with the earlier figures from which they are derived.

Lethal Phase and Use of a Multi-Phase Lethal System (MPLS)

If the requirement is simply to kill all progeny, or all progeny of one sex, then the lethal phase is not important. However, we consider that there are several advantages to engineering embryo-specific lethality. The lethal phase must end before the developmental stage at which the insects are released, or they may lose fitness or die once the repressor has been withdrawn, e.g. following release. Embryonic lethality ensures that no larvae emerge to damage crops or animals. This may not be important in the case of disease vectors such as mosquitoes, where only the adult stages transmit the disease, but is clearly critical in the case of many crop pests where it is the voracious larvae that cause the economic damage. Embryo-specific lethality allows the last and biggest mass-reared generation to be reared on food lacking the repressor, reducing costs and any environmental hazards associated with large quantities of Tc. Embryo-specific lethality (or other early lethality) can also be combined with later sex-specific lethality, e.g. female-specific lethality. We have demonstrated that this allows the construction of a strain in which both sex-separation and "sterilization" are automatic consequences of the withdrawal of Tc from the last generation prior to release. We call this system a multi-phase lethal system (MPLS), to indicate that there are two different lethal phases with different properties. In many rearing/distribution scenarios, the genetics of such a system appear similar to that of a single-sex release of radiation-sterilised males, in that only males are reached and they have no viable progeny when mating with wild males in the natural environment. However, there are two major advantages that are seen in the models below. Firstly of course the MPLS males have not been irradiated, and so do not suffer the loss of fitness and longevity consequent upon irradiation. Secondly, since the requirement is only that that the two (or more) lethal phases do not overlap, not that one of them is specific to embryos, we could arrange that the first lethal phase is after a density-dependent mortality phase in the wild population. For example, in the case of mosquitoes, in order to prevent transmission of most mosquito-borne diseases (e.g. malaria, dengue fever, yellow fever) it is only necessary to prevent the females taking their second blood meal. Killing females as pupae, emerging adults or just following their first blood meal is would therefore be suitable. The earlier non-sex-specific lethal phase only has to be earlier than this, and could therefore be as late as early adulthood, for example. Alternatively, a first lethal phase of late larval/pupal development would be possible. Promoters suitable for all these stages are well-known—blood-meal inducible genes for killing post-blood meal, etc. Using a lethal phase that first acts later than a density-dependent mortality phase in the wild population means that individuals that will later die due to the lethal effect of the RIDL system nonetheless compete for resources with their wild type conspecifics and so tend to increase the mortality of these wild type conspecifics. In the graphs below, SIT and MPLS give the same outcomes, except where otherwise noted.

Linking of the DFL to a Meiotic Drive/Segregation Distortion System

The meiotic drive system acts to enhance the effectiveness of the RIDL system (FIG. 2). Meiotic drive systems of varying effectiveness are known in a wide range of species, including Drosophila and mosquitoes. In normal Mendelian inheritance, each of the two homologues of a given chromosome is equally likely to be inherited, i.e. each has a 50% chance of being inherited by each individual offspring. The consequence of a meiotic drive/segregation distortion system is that one chromosome is preferentially inherited. We explored the effect of this by considering systems in which the chromosome carrying the RIDL system is preferentially inherited by progeny of heterozygotes carrying this chromosome and its homologue from the wild population. Since meiotic drive/segregation distortion systems vary in effectiveness, we considered inheritance frequencies of 50% (i.e. no meiotic drive/segregation distortion), 60%, 70%, 80%, 90% and 100%. Higher inheritance frequencies always make the RIDL system more effective.

Released Males being Homozygous for DFLs on Multiple Chromosomes

Unlike SIT, the impact of a RIDL system can potentially be increased by increasing the copy number of the system within the released individuals. We have considered the consequences of releasing males homozygous for a dominant female-specific lethal at one, two or three unlinked loci. We found that released males with multiple DFL chromosomes will more effectively control the population size (FIG. 3).

Reduced Fitness

FIGS. 4 and 5 demonstrate the effects of reduced fitness on SIT and RIDL systems (with meiotic drive and multiple chromosome systems). Obviously, reduced fitness in released males decreases the effectiveness of these control systems. In FIGS. 4b and 5b we assume that RIDL males have twice the competitive mating fitness of SIT males. This is a very conservative estimate. Radiation reduces the competitive mating ability of the irradiated insects (by an estimated two-fold in the case of medfly) and also reduces their longevity (by an estimated 2-5 fold in the case of medfly). This reduces the overall competitive mating ability by an estimated 4-10 fold in the case of medfly, more in the case of the pink bollworm, less in the case of the screwworm fly. An overall two-fold advantage for the non-irradiated RIDL flies over their irradiated SIT equivalents is therefore a very conservative estimate. We found that even this advantage is extremely significant in terms of the cost and effectiveness of a control programme (FIGS. 4b and 5b).

Density Dependence Mechanism

We consider three scenarios:
(a) density dependent mortality acts before RIDL-induced mortality and acts on newly released RIDL or SIT insects,
(b) density dependent mortality acts before RIDL-induced mortality but does not act on newly released RIDL insects, and (c) density dependent mortality acts after RIDL-induced mortality but does not act on newly released RIDL insects.

Scenario (a) models an adult lethal phase and density-dependent mortality acting at the level of adults. An adult lethal phase for RIDL might be appropriate for malaria vectors, where the females need only be killed within a week or so after their first blood meal to prevent transmission of the disease. Alternatively, this scenario also models an earlier release and density-dependent stage, which is available for RIDL, where the release population can be released at any life cycle stage, but not for SIT where sex-separation (if used) and irradiation have to be performed prior to release, restricting the range of life cycle stages that can be released.

Scenario (b) is a very important and novel case. This represents a density-dependent mortality that acts before RIDL-induced mortality. In the case of mosquitoes, competition between larvae for resources is a likely stage for density-dependent effects. RIDL-induced mortality can safely be later than this, as only the adult females transmit disease. Such mortality could be achieved by using a late-acting promoter, such as that from the vitellogenin gene (for female-specific mortality) in the vector of Example 7. This strategy is also possible using a multi-phase lethal system (MPLS) in which the non-sex-specific lethal stage is later than the density-dependent mortality. No equivalent strategy is available for SIT.

Scenario (c) represents release at a late life cycle stage, e.g. adults, and early RIDL-induced lethality, e.g. as embryos. Density-dependent mortality lies between these. This might represent some crop-eating agricultural pests, where the larval stages do the damage and so it would be inappropriate to release these stages or to arrange for the RIDL-induced mortality to be so late that the larvae have already done some damage before they die. Unlike scenarios (a) and (b), RIDL has no especial life-cycle-derived advantage over SIT under this scenario.

FIGS. 6 and 7 illustrate the benefits of delaying RIDL-induced mortality until after density dependent mortality, as well as the potential further benefit of releasing insects (both males and females) prior to the density-dependent mortality. These graphs further illustrate the benefits to be gained from increased meiotic drive systems and multiple chromosome DFL systems.

FIGS. 6b, 6c, 7b and 7c reveal that SIT can actually lead to a higher stable population than would have been the case in the absence of the control programme. This effect has previously been noted by Rogers and Randolph (Rogers and Randolph, 1984 Insect Sci. Applic. 5, 419-23).

General Points

For an assumed pattern of productivity and mortality, it is easy to predict that increases in meiotic drive will improve effectiveness, increases in the number of loci with DFLs will improve effectiveness and reduced fitness in released males, relative to wild type males, will decrease the effectiveness. However, the model demonstrates the relative impact of these changes and most importantly demonstrates that reduced fitness may simply act to slow down the control of an insect population, but it can also mean that the insect population cannot be eliminated without a larger input of RIDL or SIT males. Similarly, increased meiotic drives can act to improve a given system enough to eliminate an insect population that would not have been eliminated with a meiotic drive of 50%. Furthermore, not all of the outcomes are intuitively obvious. The possibility that SIT can actually lead to a higher stable population than would have been the case in the absence of the control programme has been mentioned above. Additionally, it is clear that under some circumstances the wild population may actually rise during the early stages of the control programme and yet still be eradicated in the longer term. For example, in FIG. 2b with 70% meiotic drive, the population is higher than its initial level from generation 1 to generation 7, yet is still ultimately controlled.

Note that in several of the graphs the long dashed line shown in the key appears in the plot as a continuous or segmented lines. It is nevertheless clear from the context which line is which.

In detail, the Figures are explained as follows:

FIG. 2: Meiotic drive system. 50%, 60%, 70%, 80%, 90% and 100% for a single locus system with no decreased fitness. The bold black line is the SIT system in each case. The RIDL system is plotted with grey lines.

a $R_0$ is 1.5 and input is 0.5 (relative to the initial population). SIT maintains the population at a constant level, whereas the RIDL systems quickly reduce the populations. If the population were not subject to control, by generation 15 we would expect $(1.5)^{15}$=438 times as many insects as the initial population.

b $R_0$ is 2.25 and input is 1 (relative to the initial population). The population is not controlled by SIT or RIDL with 50% or 60% meiotic drive. By generation 15 they have 8000, 2200 and 360 times as many insects as the initial population, respectively. If the population were not subject to control, by generation 15 we would expect $(2.25)^{15}$=191751 times as many insects as the initial population. The populations are quickly brought under control with greater meiotic drive levels.

FIG. 3: Multiple unlinked loci used in RIDL system. The bold black line is the SIT system in each case. The RIDL system is plotted with grey lines.

a $R_0$ is 1.5 and input is 0.5 (relative to the initial population). SIT maintains the population at a constant level, whereas the RIDL systems quickly reduce the populations. If the population were not subject to control, by generation 15 we would expect $(1.5)^{15}$=438 times as many insects as the initial population.

b $R_0$ is 2.25 and input is 1 (relative to the initial population). The population is not controlled by SIT or RIDL with 1 or 2 loci. By generation 15 they have 8000, 2200 and 34 times as many insects as the initial population, respectively. If the population were not subject to control, by generation 15 we would expect $(2.25)^{15}$=191751 times as many insects as the initial population. The populations are quickly brought under control with a 3 locus RIDL system.

FIG. 4: Meiotic drive system. 50%, 60%, 70%, 80%, 90% and 100% for a single locus system with decreased fitness. The bold black line is the SIT system in each case. The RIDL system is plotted with grey lines.

a $R_0$ is 1.5 and input is 0.5 (relative to the initial population). The fitness of SIT and released RIDL insects is 80% of that of wild type insects. Subsequent generations are assumed to have equal fitness to wild type insects regardless of their parentage. The population is not controlled by SIT or RIDL with 50% meiotic drive. By generation 15 they have 44 and 1.5 times as many insects as the initial population, respectively. If the population were not subject to control, by generation 15 we would expect $(1.5)^{15}$=438 times as many insects as the initial population. The populations are quickly brought under control with greater meiotic drive levels, despite the reduced fitness.

b $R_0$ is 1.5 and input is 1.75 (relative to the initial population). The fitness of SIT is 25% of that of wild type insects, whereas released RIDL insects have 50% of the fitness of wild type insects. Subsequent generations are assumed to have equal fitness to wild type insects regardless of their parentage. The population is not controlled by SIT. By generation 15 it has 23 times as many insects as the initial population. If the population were not subject to control, by generation 15 we would expect $(1.5)^{15}=438$ times as many insects as the initial population. The populations are quickly brought under control with RIDL systems, despite the reduced fitness.

FIG. 5: Multiple unlinked loci used in RIDL system with decreased fitness. The bold black line is the SIT system in each case. The RIDL system is plotted with grey lines.

a $R_0$ is 1.5 and input is 0.5 (relative to the initial population). The fitness of SIT and released RIDL insects is 80% of that of wild type insects. Subsequent generations are assumed to have equal fitness to wild type insects regardless of their parentage The population is not controlled by SIT or RIDL with 50 meiotic drive. By generation 15 they have 44 and 1.5 times as many insects as the initial population, respectively. If the population were not subject to control, by generation 15 we would expect $(1.5)^{15}=438$ times as many insects as the initial population. The populations are quickly brought under control with multiple loci, despite the reduced fitness.

b $R_0$ is 1.5 and input is 1.75 (relative to the initial population). The fitness of SIT is 25% of that of wild type insects, whereas released RIDL insects have 50% of the fitness of wild type insects. Subsequent generations are assumed to have equal fitness to wild type insects regardless of their parentage. The population is not controlled by SIT. By generation 15 it has 23 times as many insects as the initial population. If the population were not subject to control, by generation 15 we would expect $(1.5)^{15}=438$ times as many insects as the initial population. The populations are quickly brought under control with RIDL systems, despite the reduced fitness.

FIG. 6: Meiotic drive system. 50%, 60%, 70%, 80%, 90% and 100% for a single locus system with no decreased fitness—in a density-dependent system. The bold black line is the SIT system in each case. The RIDL system is plotted with grey lines. In all cases a=1, b=2, $R_0$ is 4.5 and input is 1 (relative to the initial population).

a Density dependent mortality acts before RIDL-induced mortality and acts on newly released RIDL insects. SIT maintains the population at a constant level of 0.8 relative to the initial population, whereas the RIDL systems quickly reduce the populations. If the population were not subject to control, we would expect the population to remain stable at the initial size.

b Density dependent mortality acts before RIDL-induced mortality but does not act on newly released RIDL insects. The population is eliminated by SIT or RIDL with 50% or 60% meiotic drive. They stabilize the population at the levels 1.2, 0.4 and 0.3, relative to the initial population, respectively. The populations are quickly brought under control with greater meiotic drive levels. If the population were not subject to control, we would expect the population to remain stable at the initial size.

c Density dependent mortality acts after RIDL-induced mortality but does not act on newly released RIDL insects. The population is eliminated by SIT or RIDL with 50%, 60% or 70% meiotic drive. They stabilize the population at the levels 1.2, 0.75, 0.7 and 0.6, relative to the initial population, respectively. The populations are quickly brought under control with greater meiotic drive levels, despite the reduced fitness. If the population were not subject to control, we would expect the population to remain stable at the initial size.

FIG. 7: Multiple unlinked loci used in RIDL system with no decreased fitness—in a density-dependent system. The bold black line is the SIT system in each case. The RIDL system is plotted with grey lines. In all cases a=1, b=2, $R_0$ is 4.5 and input is 1 (relative to the initial population).

a Density dependent mortality acts before RIDL-induced mortality and acts on newly released RIDL insects. SIT maintains the population at a constant level of 0.8 relative to the initial population, whereas the RIDL systems reduce the populations. If the population were not subject to control, we would expect the population to remain stable at the initial size.

b Density dependent mortality acts before RIDL-induced mortality but does not act on newly released RIDL insects. The population is maintained at a constant level by SIT or RIDL with 1 locus. They stabilize the population at the levels 1.2 and 0.4, relative to the initial population, respectively. The populations are eliminated with 2 or 3 locus systems. If the population were not subject to control, we would expect the population to remain stable at the initial size.

c Density dependent mortality acts after RIDL-induced mortality but does not act on newly released RIDL insects. The population is maintained at a constant level by SIT or RIDL with 1, 2 or 3 loci. They stabilize the population at the levels 1.2, 0.75, 0.63 and 0.5, relative to the initial population, respectively. If the population were not subject to control, we would expect the population to remain stable at the initial size.

FIG. 8

The plots a-d are based on scenario of FIG. 2, with the first two releases doubled in size.

| (a) Ro = 1.5, later input = 0.5 | (b) Ro = 2.25, later input = 1 |
|---|---|
| (c) Ro = 1.5, later input = 0.5 | (d) Ro = 2.25, later input = 1 |

The plots e-g are based on scenario of FIG. 6, with the first two releases doubled in size.

(e) see FIG. 6
(f) see FIG. 6b
(g) see FIG. 6c

The plots h-j are based on scenario of FIG. 7, with the first two releases doubled in size.

(h) see FIG. 7a
(i) see FIG. 7b
(j) see FIG. 7c

The invention claimed is:

1. A recombinant insect whose genome comprises a dominant lethal genetic system with a conditional lethal effect, the system comprising:
   (i) a lethal gene under the control of a promoter, wherein the lethal gene is present in the system regardless of sex of the insect,
   (ii) a transactivator gene, which expresses a repressible transactivator protein and is under the control of sex-specific promoter; and
   (iii) a binding sequence for the repressible transactivator protein, wherein the lethal effect of the system is sex-specific, and expression of the lethal gene is activatable by the repressible transactivator protein which is repressible by a tetracycline, tetracycline analogue, or tetracycline derivative,
   wherein the lethal effect of the genetic system is repressible by the tetracycline, analogue, or derivative, and
   wherein the insect is a mosquito, medfly or pink bollworm.

2. The recombinant insect of claim 1, wherein the lethal gene is a sex-specific lethal gene.

3. The recombinant insect of claim 1, wherein a product of the lethal gene is lethal to only one sex of the recombinant insect.

4. The recombinant insect of claim 1, wherein the lethal gene is expressed in only one sex of the recombinant insect or a product of the lethal gene is produced in only one sex of the insect.

5. The recombinant insect of claim 1, wherein the lethal effect is controlled by a sex-specific promoter or enhancer or by sex-specific splicing.

6. The recombinant insect of claim 1, wherein the sex-specificity of the genetic system is mediated by sex-specific splicing.

7. The recombinant insect of claim 1, wherein the lethal system is homozygous at more than one locus.

8. The recombinant insect of claim 1, wherein the lethal system is located on the X chromosome.

9. The recombinant insect of claim 1, wherein the conditional lethal effect of the genetic system is specific for an embryonic or larval life cycle stage.

10. The recombinant insect of claim 1, wherein the conditional lethal effect is specific to females or female tissue for at least one life cycle stage.

11. The recombinant insect of claim 1, wherein the lethal gene comprises an inhibitor sequence selected from the group consisting of: antisense RNA, sense RNA, and double stranded RNA.

12. A method for breeding a stock of recombinant insects, comprising the steps of:
   (i) obtaining a stock of recombinant insects of the same species of claim 1; and
   (ii) breeding the stock of recombinant insects from step (i) under permissive conditions.

13. The method of claim 12, wherein both males and females are distributed in step (iii).

14. The method of claim 12, wherein a single sex is distributed in step (iii).

15. The method of claim 12, wherein the method further comprises sex-separation prior to step (iii).

16. The method of claim 12, wherein the method results in killing of greater than 90% of the target class of the progeny resulting from the breeding of stock insects with wild-type insects.

17. The method of claim 12, further comprising distributing the stock of recombinant insects from step (ii) into an environment lacking tetracycline, tetracycline analog or tetracycline derivative, whereby individual recombinant stock insects breed with the same species in the wild-type population to produce offspring expressing the lethal gene.

* * * * *